United States Patent [19]

Bergström et al.

[11] Patent Number: 5,739,407
[45] Date of Patent: Apr. 14, 1998

[54] HUMAN β-CASEIN, PROCESS FOR PRODUCING IT AND USE THEREOF

[75] Inventors: Sven Bergström; Olle Hernell, both of Umea, Sweden; Bo Lönnerdal, Davis, Calif.; Karin Hjalmarsson, Umea, Sweden; Lennart Hanson, Umea, Sweden; Jan Törnell, Göteborg, Sweden; Mats Strömqvigt, Umea, Sweden

[73] Assignee: Symbicom aktiebolag, Umea, Sweden

[21] Appl. No.: 78,090

[22] Filed: Jun. 18, 1993

Related U.S. Application Data

[63] Continuation-in-part of PCT/DK92/00246, Aug. 19, 1992 which is a continuation-in-part of PCT/DK91/00233, Aug. 19, 1991.

[51] Int. Cl.$^6$ .............................. C12N 5/00; C12N 15/00
[52] U.S. Cl. .............................. 800/2; 426/580; 426/590; 426/648; 426/657; 426/801; 435/172.1; 435/172.3; 435/320.1; 530/361; 536/23.5; 536/24.1; 800/DIG. 1; 935/60
[58] Field of Search .............................. 800/2, DIG. 1; 435/172.1, 172.3, 320.1; 536/23.1, 23.5, 24.1; 530/360, 361; 935/9, 59, 64; 426/580, 590, 648, 657, 801

[56] References Cited

FOREIGN PATENT DOCUMENTS

| | | |
|---|---|---|
| 0247494 | 12/1987 | European Pat. Off. . |
| 0264166 | 4/1988 | European Pat. Off. . |
| 0279582 | 8/1988 | European Pat. Off. . |
| 8204443 | 12/1982 | WIPO . |
| 8800239 | 1/1988 | WIPO . |
| 8801648 | 3/1988 | WIPO . |
| 9103551 | 3/1991 | WIPO . |
| 9108216 | 6/1991 | WIPO . |
| 9108675 | 6/1991 | WIPO . |
| 9203917 | 3/1992 | WIPO . |

OTHER PUBLICATIONS

J Van Brunt (1988) Bio/Technology 6:1149–1154.
MR Capecchi (1989) Science 244:1288–1292.
TA Brown (1990) Gene Cloning. pp. 153–177.
K-F Lee et al (1989) Mol Cell Biol 9:560–565.
American Academy of Pediatrics, Committe on Nutrition: "Commentary on Breast–Feeding and Infant Formulas, including Proposed Standards for Formulas"; Pediatrics 57, 278–285 (1976).
American Academy of Pediatrics, Committee on Nutrition: "Soy–Protein: Recommendations for Use in Infant Feeding"; Pediatrics, vol. 72, No. 3, pp. 359–363 (1983).
J. Bonsing et al, "Complete Nucleotide Sequence of the Bovine Beta–Casein Gene"; Aust. J. Biol. Sci., vol. 41, pp. 527–537 (1988).

(List continued on next page.)

*Primary Examiner*—Bruce R. Campell
*Attorney, Agent, or Firm*—Iver P. Cooper

[57] ABSTRACT

The present invention relates to a DNA sequence encoding the human milk protein β-casein or an analogue or variant thereof which has either the calcium binding activity of human β-casein, or opioid activity, or angiotensin converting enzyme (ACE) inhibitory activity, or a combination of any two or three of these activities. The DNA sequence may optionally contain one or more intron sequences and permissive RNA splice signals. The DNA sequence is used in the production of recombinant human β-casein, advantageously by means of production in transgenic non-human mammals such as bovine species. In one embodiment, the DNA sequence is inserted into a milk protein gene of a mammal such as a whey acidic protein (WAP) gene. The main use of the recombinant human β-casein is as a constituent of infant formulae. It is contemplated that the recombinant human β-casein provides a substantial improvement of the nutritional and biological value of the formulae in that a closer similarity to human milk is obtained.

7 Claims, 26 Drawing Sheets

OTHER PUBLICATIONS

R. J. Bollag et al, "Homologous Recombination in Mammalian Cells"; Annu. Rev. Genet, vol. 23, pp. 199–225, (1989).

T. A. Bongso, "Prenatal Diagnosis of Sex in Cattle by Amniocentesis"; The Veterinary Record, vol. 96, pp. 124–127 (1975).

V. Brantl, "Novel Opioid Peptides Derived From Human Beta–Casein: Human Beta–Casomorphins", European Journal of Pharmacology; vol. 106, pp. 213–214 (1985).

R. L. Brinster et al, "Introns Increase Transcriptional Efficiency in Transgenic Mice", Proc. Natl. Sci. U.S.A., vol. 85, pp. 836–840 (1988).

S. M. Campbell et al, "Comparison of the Whey Acidic Protein Genes of the Rat and Mouse", Nucleic Acids Research; vol. 12, No. 22, pp. 8685–8697 (1984).

A. J. Clark et al, "Pharmaceuticals from Transgenic Livestock"; TibTech, vol. 5, pp. 20–24 (1987).

S. E. Donahue, "A Technique for Bisection of Embryos to Produce Identical Twins", Genetic Engineering of Animals, pp. 163–173 (1986).

W. H. Eyestone et al, "Co–culture of Early Cattle Embryos to the Blastocyst Stage with Oviducal Tissue or in Conditioned Medium"; J. Reprod. Fert., vol. 85, pp. 715–720 (1989).

F. Gandolfi et al, "Stimulation of Early Embryonic Development in the Sheep by Co–culture with Oviduct Epithelial cells", J. Reprod. Fert., vol. 81, pp. 23–28 (1987).

R. Greenberg et al, "Human β–Casein, Amino Acid Sequence and Identification of Phosphorylation Sites", J. Biol. Chem., vol. 259; pp. 5132–5138 (1984).

R. E. Hammer et al, "Production of Transgenic Rabbits, Sheep and Pigs by Microinjection"; Nature, vol. 315, pp. 680–683 (1985).

Y. Heyman et al, "In Vitro Cleavage of Bovine and Ovine Early Embryos: Improved Development Using Coculture with Trophoblastic Vesicles"; Theriogenology, vol. 27, No. 1, pp. 59–69 (1987).

W. Jones et al, "The Rat Casein Multigene Family: Fine Structure and Evolution of the Beta–Casein Gene"; J. Biol. Chem., vol. 260, No. 11, pp. 7042–7050 (1985).

D. King et al, Identification of Specific Gene Sequences in Preimplantation Embryos by Genomic Amplification: Detection of a Transgene; Molecular Reproduction and Development, 1:57–62 (1988).

M. Kohmura et al, Inhibition of Angiotensin–converting Enzyme by Synthetic Peptides of Human β–Casein; Agric. Biol. Chem. vol. 53, pp. 2107–2114 (1989).

S. Maruyama et al, "Angiotensin I–Converting Enzyme Inhibitor Derived from an Enzymatic Hydrolysate of Casein . . . "; Agric. Biol. Chem., vol. 49, pp. 1405–1410.

R.S. Menon et al, Human β–Casein: Partial cDNA Sequence and Apparent Polymorphism; Nucleic Acids Res., vol. 17, 2869 (1989).

D. Migliore–Samour et al, "Casein, a Phormone with an Immunomodulating Role for the Newborn?"; Experientia 44 (1988) pp. 188–193 (1988).

M. Miller et al; "Casein: A Milk Protein with Diverse Biologic Consequences"; Proc. Soc. Exp. Biol. Med. vol. 195, pp. 143–159 (1990).

J. J. Parrish et al, Bovine In Vitro Fertilization with Frozen–Thawed Semen; Theriogenology, vol. 24, No. 4, pp. 591–600 (1986).

J. J. Parrish et al, "Capacitation of Bovine by Heparin"; Biol. Reprod., vol. 38, pp. 1171–1180 (1988).

R. S. Prather et al, "Nuclear Transplantation in the Bovine Embryo: Assessment of Donor Nuclei and Recipient Oocyte", Biol. Reprod., vol. 37, pp. 859–866 (1987).

C. E. Rexroad et al, "Co–Culture of Ovine Ova with Oviductal Cells in Medium 199"; J. Anim. Sci., vol. 66: pp. 947–953 (1988).

J. M. Robl et al, "Nuclear Transplantation in Bovine Embryos"; J. Anim. Sci. vol. 64; pp. 642–697 (1987).

M. A. Sirard et al, "The Culture of Bovine Oocytes to Obtain Developmentally Component Embryos"; Biol. Reprod., vol. 39, pp. 546–522 (1988).

R. J. Wall et al, "Development of Porcine Ova that were Centrifuged to Permit Visualization of Pronuclei and Nuclei", Biol. Reprod., vol. 32, pp. 645–651 (1985).

T. J. Williams et al, "Pregnancy Rates with Bisected Bovine Embryos"; Theriogenology; vol. 22, No. 5, pp. 521–531 (1984).

Yoshimura et al, "Isolation and Structural Analysis of the Mouse β–casein Gene"; Gene, vol. 78, pp. 267–275 (1990).

P. Martin et al, "Exon–skipping is Responsible for the 9–amino acid Residue Deletion Occurring Near the N–terminal of Human Beta–Casein", Biochem. Biophys. Res. Commun., vol. 183, No. 2, pp. 750–757 (1992).

R. S. Menon et al, "Exon Skipping in Human β–casein"; Genomics, vol. 12, pp. 13–17 (1992).

D. Thepot et al, "Structure of the Gene Encoding Rabbit Beta–Casein"; Gene, vol. 97, pp. 301–306 (1991).

B. Loennerdal et al, "Cloning and Sequencing of cDNA Encoding Human Milk Beta–Casein"; FEBS, vol. 269, No. 1, pp. 153–156 (1990).

B. Loennerdal et al, "Cloning and Sequencing of a cDNA Encoding Human Milk Beta–Casein"; FASEB Journal, vol. 4, No. 3, p. A671, Abstract No. 2348 (1990).

C.W. Pittius, et al, "A Milk Protein Gene Promotor Directs the Expression of Human Tissue Plasminogen Activator cDNA to the Mammary Gland in Transgenic Mice", Proc. Natl. Acad. Sci. USA, vol. 85, pp. 5874–5878 (1988).

R.D. Bremel et al, "Alteration of Milk Composition Molecular Genetics", J. Dairy Sci., vol. 72, pp. 2826–2833 (1988).

F.W. Studier et al, "Use of T7 RNA Polymerase to Direct Expression of Cloned Genes", Methods in Enzymology, vol. 185, pp. 60–89 (1990).

L. Henninghausen, "The Mammary Gland as a Bioreactor: Production of Foreign Proteins in Milk", Protein Expression and Purification, vol. 1, pp. 3–8 (1990).

```
                -15                                       -1 +1
         M  K  V  L  I  L  A  C  L  V  A  L  A  L  A  R  E  T  I
      cggatgaaggtcctcatcctcgcctgcctggtggctcttgctcttgcaagggagaccata
      1                                                          60

10                            20
       E  S  L  S  S  S  E  E  S  I  T  E  Y  K  K  V  E  K  V  K
      gaaagcctttcaagcagtgaggaatctattacagaatacaagaaagttgagaaggttaaa
                                                                120

30                             40
       H  E  D  Q  Q  Q  G  E  D  E  H  Q  D  K  I  Y  P  S  F  Q
      catgaggaccagcagcaaggagaggatgaacaccaggataaaatctacccctcttttccag
      121                                                        180

50                             60
       P  Q  P  L  I  Y  P  F  V  E  P  I  P  Y  G  F  L  P  Q  N
      ccacagcctctgatctatccattcgttgaacctatcccctatggttttcttccacaaaac
      181                                                        240

70                             80
       I  L  P  L  A  Q  P  A  V  V  L  P  V  P  Q  P  E  I  M  E
      attctgcctcttgctcagcctgctgtggtgctgcctgtccctcagcctgaaataatggaa
      241-------------------->                                   300
              <--------------------

90                            100
       V  P  K  A  K  D  T  V  Y  T  K  G  R  V  M  P  V  L  K  S
      gtccctaaagctaaagacactgtctacactaagggcagagtgatgcctgtccttaaatct
      301                                                        360

110                            120
       P  T  I  P  F  F  D  P  Q  I  P  K  L  T  D  L  E  N  L  H
      ccaacgataccctttttttgaccctcaaatcccaaaactcactgatcttgaaaatctgcat
      361                                     _____

130                            140
       L  P  L  P  L  L  Q  P  L  M  Q  Q  V  P  Q  P  I  P  Q  T
      cttcctctgcctctgctccagcccttgatgcagcaggtccctcagcctattcctcagact
      _____                                     480
```

Fig. 1A

```
                    150                              160
      L   A   L   P   P   Q   P   L   W   S   V   P   Q   P   K   V   L   P   I   P
      cttgcacttcccccctcagcccctgtggtctgttcctcagcccaaagtcctgcctatcccc
      481                                                          --------
                              <----------------------
                    170                              180
      Q   Q   V   V   P   Y   P   Q   R   A   V   P   V   Q   A   L   L   N   Q
      cagcaagtggtgccctaccctcagagagctgtgcctgttcaagcccttctgctcaaccaa
      ------------>                                                        600

190                              200
      E   L   L   N   P   T   H   Q   I   Y   P   V   T   Q   P   L   A   P   V
      gaacttctacttaaccccacccaccagatctaccctgtgactcagccacttgccccagtt
      601                                                                  660

210
      H   N   P   I   S   V   *
      cataaccccattagtgtctaagaagatttcaaagttaattttccctccttattttgaat
      661                                                                  720 tgactgagactggaaatatgatgccttttccgtctttgtatcacgttaccccaaattaag
      721                                                                  780 tatgtttgaatgagtttatatggaaaaaatgaactttgtccctttatttattttatatat
      781                                                                  840 tatgtcattcatttaatttgaaatttgactcatgaactatttacattttccaaatcttaa
      841               <----------------------                            900 ttcaactagtaccacagaagttcaatactcatttggaaatgctacaaacatatcaaacat
      901                                                                  960 atgtatacaaattgtttctggaattgtgcttattttattcttaagaatctatttcct
      961                                                                  1020 ttccagtcatttcaataaattattcttaagcataaaaaaaaaaaa
      1021                                          1065
```

Fig. 1B

```
          10           20           30 ·         40           50           60
           *            *            *            *            *            *
GGTAC CCTAA AGGAC TTGAC AGCCA TGAAG GTCCT CATCC TCGCC TGCCT GGTGG CTCTT
CCATG GGATT TCCTG AACTG TCGGT ACTTC CAGGA GTAGG AGCGG ACGGA CCACC GAGAA 70           80           90          100          110          120
           *            *            *            *            *            *
GCTCT TGCAA GGGAG ACCAT AGAAA GCCTT TCAAG CAGTG AGGAA TCTAT TACAG AATAC
CGAGA ACGTT CCCTC TGGTA TCTTT CGGAA AGTTC GTCAC TCCTT AGATA ATGTC TTATG 130          140          150          160          170          180
           *            *            *            *            *            *
AAGAA AGTTG AGAAG GTTAA ACATG AGGAC CAGCA GCAAG GAGAG GATGA ACACC AGGAT
TTCTT TCAAC TCTTC CAATT TGTAC TCCTG GTCGT CGTTC CTCTC CTACT TGTGG TCCTA 190          200          ·210         220          230          240
           *            *            *            *            *            *
AAAAT CTACC CCTCT TTCCA GCCAC AGCCT CTGAT CTATC CATTC GTTGA ACCTA TCCCC
TTTTA GATGG GGAGA AAGGT CGGTG TCGGA GACTA GATAG GTAAG CAACT TGGAT AGGGG 250          260          270          280          290          300
           *            *            *            *            *            *
TATGG TTTTC TTCCA CAAAA CATTC TGCCT CTTGC TCAGC CTGCT GTGGT GCTGC CTGTC
ATACC AAAAG AAGGT GTTTT GTAAG ACGGA GAACG AGTCG GACGA CACCA CGACG GACAG 310          320          330          340          350          360
           *            *            *            *            *            *
CCTCA GCCTG AAATA ATGGA AGTCC CTAAA GCTAA AGACA CTGTC TACAC TAAGG GCAGA
GGAGT CGGAC TTTAT TACCT TCAGG GATTT CGATT TCTGT GACAG ATGTG ATTCC CGTCT 370          380          390          400          410          420
           *            *            *            *            *            *
GTGAT GCCTG TCCTT AAATC TCCAA CGATA CCCTT TTTTG ACCCT CAAAT CCCAA AACTC
CACTA CGGAC AGGAA TTTAG AGGTT GCTAT GGGAA AAAAC TGGGA GTTTA GGGTT TTGAG 430          440          450          460          470          480
           *            *            *            *            *            *
ACTGA TCTTG AAAAT CTGCA TCTTC CTCTG CCTCT GCTCC AGCCC TTGAT GCAGC AGGTC
TGACT AGAAC TTTTA GACGT AGAAG GAGAC GGAGA CGAGG TCGGG AACTA CGTCG TCCAG 490          500          510          520          530          540
           *            *            *            *            *            *
CCTCA GCCTA TTCCT CAGAC TCTTG CACTT CCCCC TCAGC CCCTG TGGTC TGTTC CTCAG
GGAGT CGGAT AAGGA GTCTG AGAAC GTGAA GGGGG AGTCG GGGAC ACCAG ACAAG GAGTC 550          560          570          580          590          600
           *            *            *            *            *            *
CCCAA AGTCC TGCCT ATCCC CCAGC AAGTG GTGCC CTACC CTCAG AGAGC TGTGC CTGTT
GGGTT TCAGG ACGGA TAGGG GGTCG TTCAC CACGG GATGG GAGTC TCTCG ACACG GACAA 610          620          630          640          650          660
           *            *            *            *            *            *
CAAGC CCTTC TGCTC AACCA GAAAC TTCTA CTTAA CCCCA CCCAC CAGAT CTACC CTGTG
GTTCG GGAAG ACGAG TTGGT TCTTG AAGAT GAATT GGGGT GGGTG GTCTA GATGG GACAC 670          680          690          700
           *            *            *            *
ACTCA GCCAC TTGCC CCAGT TCATA ACCCC ATTAG TGTCT AAGTC GAC
TGAGT CGGTG AACGG GGTCA AGTAT TGGGG TAATC ACAGA TTCAG CTG
```

Fig. 9

| Primer | Sequence (5'-3') |
|---|---|
| 5'-primer | CTGTGTGGCAAGAAGGAAGTGTTGT |
| 3'-primer | AGGCAGGACTTTGGGCTGAGG |

Fig. 16B

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 1065 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: sig_peptide
( B ) LOCATION: 4..48

( i x ) FEATURE:
( A ) NAME/KEY: CDS
( B ) LOCATION: 49..681

( x i ) SEQUENCE DESCRIPTION: SEQ ID NO:1:

```
CGGATGAAGG TCCTCATCCT CGCCTGCCTG GTGGCTCTTG CTCTTGCA AGG GAG ACC              57
                                                     Arg Glu Thr
                                                         1

ATA GAA AGC CTT TCA AGC AGT GAG GAA TCT ATT ACA GAA TAC AAG AAA             105
Ile Glu Ser Leu Ser Ser Ser Glu Glu Ser Ile Thr Glu Tyr Lys Lys
        5                   10                  15

GTT GAG AAG GTT AAA CAT GAG GAC CAG CAG CAA GGA GAG GAT GAA CAC             153
Val Glu Lys Val Lys His Glu Asp Gln Gln Gln Gly Glu Asp Glu His
 20                  25                  30                  35

CAG GAT AAA ATC TAC CCC TCT TTC CAG CCA CAG CCT CTG ATC TAT CCA             201
Gln Asp Lys Ile Tyr Pro Ser Phe Gln Pro Gln Pro Leu Ile Tyr Pro
                 40                  45                  50

TTC GTT GAA CCT ATC CCC TAT GGT TTT CTT CCA CAA AAC ATT CTG CCT             249
Phe Val Glu Pro Ile Pro Tyr Gly Phe Leu Pro Gln Asn Ile Leu Pro
             55                  60                  65

CTT GCT CAG CCT GCT GTG GTG CTG CCT GTC CCT CAG CCT GAA ATA ATG             297
Leu Ala Gln Pro Ala Val Val Leu Pro Val Pro Gln Pro Glu Ile Met
         70                  75                  80

GAA GTC CCT AAA GCT AAA GAC ACT GTC TAC ACT AAG GGC AGA GTG ATG             345
Glu Val Pro Lys Ala Lys Asp Thr Val Tyr Thr Lys Gly Arg Val Met
     85                  90                  95

CCT GTC CTT AAA TCT CCA ACG ATA CCC TTT TTT GAC CCT CAA ATC CCA             393
Pro Val Leu Lys Ser Pro Thr Ile Pro Phe Phe Asp Pro Gln Ile Pro
100                 105                 110                 115

AAA CTC ACT GAT CTT GAA AAT CTG CAT CTT CCT CTG CCT CTG CTC CAG             441
Lys Leu Thr Asp Leu Glu Asn Leu His Leu Pro Leu Pro Leu Leu Gln
                120                 125                 130

CCC TTG ATG CAG CAG GTC CCT CAG CCT ATT CCT CAG ACT CTT GCA CTT             489
Pro Leu Met Gln Gln Val Pro Gln Pro Ile Pro Gln Thr Leu Ala Leu
            135                 140                 145

CCC CCT CAG CCC CTG TGG TCT GTT CCT CAG CCC AAA GTC CTG CCT ATC             537
Pro Pro Gln Pro Leu Trp Ser Val Pro Gln Pro Lys Val Leu Pro Ile
        150                 155                 160

CCC CAG CAA GTG GTG CCC TAC CCT CAG AGA GCT GTG CCT GTT CAA GCC             585
Pro Gln Gln Val Val Pro Tyr Pro Gln Arg Ala Val Pro Val Gln Ala
    165                 170                 175

CTT CTG CTC AAC CAA GAA CTT CTA CTT AAC CCC ACC CAC CAG ATC TAC             633
Leu Leu Leu Asn Gln Glu Leu Leu Leu Asn Pro Thr His Gln Ile Tyr
180                 185                 190                 195
```

-continued

```
CCT GTG ACT CAG CCA CTT GCC CCA GTT CAT AAC CCC ATT AGT GTCTAAGAAGATT 688
Pro Val Thr Gln Pro Leu Ala Pro Val His Asn Pro Ile Ser Val
            200                 205                 210

TCAAAGTTAA TTTTCCCTCC TTATTTTTGA ATTGACTGAG ACTGGAAATA TGATGCCTTT       748

TCCGTCTTTG TATCACGTTA CCCCAAATTA AGTATGTTTG AATGAGTTTA TATGGAAAAA       808

ATGAACTTTG TCCCTTTATT TATTTTATAT ATTATGTCAT TCATTTAATT TGAAATTTGA       868

CTCATGAACT ATTTACATTT TCCAAATCTT AATTCAACTA GTACCACAGA AGTTCAATAC       928

TCATTTGGAA ATGCTACAAA CATATCAAAC ATATGTATAC AAATTGTTTC TGGAATTGTG       988

CTTATTTTTA TTTCTTTAAG AATCTATTTC CTTTCCAGTC ATTTCAATAA ATTATTCTTA      1048

AGCATAAAAA AAAAAAA                                                    1065
```

( 2 ) INFORMATION FOR SEQ ID NO:2:

( i ) SEQUENCE CHARACTERISTICS:
       ( A ) LENGTH: 210 amino acids
       ( B ) TYPE: amino acid
       ( D ) TOPOLOGY: linear ( i i ) MOLECULE TYPE: protein ( x i ) SEQUENCE DESCRIPTION: SEQ ID NO:2:

```
Arg Glu Thr Ile Glu Ser Leu Ser Ser Ser Glu Glu Ser Ile Thr Glu
 1               5                  10                  15

Tyr Lys Lys Val Glu Lys Val Lys His Glu Asp Gln Gln Gln Gly Glu
                20                  25                  30

Asp Glu His Gln Asp Lys Ile Tyr Pro Ser Phe Gln Pro Gln Pro Leu
            35                  40                  45

Ile Tyr Pro Phe Val Glu Pro Ile Pro Tyr Gly Phe Leu Pro Gln Asn
    50                  55                  60

Ile Leu Pro Leu Ala Gln Pro Ala Val Val Leu Pro Val Pro Gln Pro
 65                  70                  75                  80

Glu Ile Met Glu Val Pro Lys Ala Lys Asp Thr Val Tyr Thr Lys Gly
                85                  90                  95

Arg Val Met Pro Val Leu Lys Ser Pro Thr Ile Pro Phe Phe Asp Pro
            100                 105                 110

Gln Ile Pro Lys Leu Thr Asp Leu Glu Asn Leu His Leu Pro Leu Pro
    115                 120                 125

Leu Leu Gln Pro Leu Met Gln Gln Val Pro Gln Pro Ile Pro Gln Thr
130                 135                 140

Leu Ala Leu Pro Pro Gln Pro Leu Trp Ser Val Pro Gln Pro Lys Val
145                 150                 155                 160

Leu Pro Ile Pro Gln Gln Val Val Pro Tyr Pro Gln Arg Ala Val Pro
                165                 170                 175

Val Gln Ala Leu Leu Leu Asn Gln Glu Leu Leu Leu Asn Pro Thr His
            180                 185                 190

Gln Ile Tyr Pro Val Thr Gln Pro Leu Ala Pro Val His Asn Pro Ile
    195                 200                 205

Ser Val
210
```

( 2 ) INFORMATION FOR SEQ ID NO:3:

( i ) SEQUENCE CHARACTERISTICS:
       ( A ) LENGTH: 10607 base pairs
       ( B ) TYPE: nucleic acid
       ( C ) STRANDEDNESS: single
       ( D ) TOPOLOGY: linear ( i i ) MOLECULE TYPE: DNA (genomic)

( i x ) FEATURE:
    ( A ) NAME/KEY: CDS
    ( B ) LOCATION: join(4804..4854, 5720..5746, 6726..6746, 6845
    . . 6886, 7991..8521, 9440..9445)

( x i ) SEQUENCE DESCRIPTION: SEQ ID NO:3:

| | | | | | |
|---|---|---|---|---|---|
| GATCTTATTT | CAAATCACAA | AATTAGTGTG | TCATTAAATA | TAGTATATAA | ACAGTCACAG | 60 |
| AAGCTGATGG | ACCATCATCC | ATCCAGCACT | ACCTTCACTT | CTCTTCAATC | TTGGAAAAAC | 120 |
| GGTAAGAATT | TTAGATACAA | ATTTGTTGTA | TCTTCTCCTA | ACCATGTATT | TCAAAGTAGC | 180 |
| TTGAGCTATA | GAAGGAACGT | AGTTACTTAA | AATATAGTGT | TTGAAATAAA | AGTATTTAAG | 240 |
| GTAGTACTGA | GATTATTTTT | AACACTTAGG | CTAAAAAGA | TAGAAGTGCC | CAGAAGAATT | 300 |
| TGGTAAAAAA | AATTGCAATG | ACATATAGCC | TTCATGAGTT | TAAGAAAATA | TAATAGCTAA | 360 |
| TTTTATGCAT | ATATATATAT | ATATATATAT | ATAGTATGAG | GCTAGTTCAT | AGTTAATATT | 420 |
| AAAAGGAGAT | TCATTTTTTT | AATTAATCTT | CCAATTTGAT | TTAGCATATC | ACAGTTATAA | 480 |
| AAAGAATTAT | ACTTCAATTA | TAGTATGGGT | AGATAAATAA | TTACTGGAAA | AGCTTTGTCC | 540 |
| AGCAGGTAGT | TTACAGCAGT | AGCATACTGA | GTTGAGAAAT | GGAGGGAATG | GTATGGGGC | 600 |
| ATTTACTACT | TTAAATGTTT | ATAAACAATG | TTTTAGAAG | AGTTTACTCA | TCAAACTTGT | 660 |
| CTAGAGCCTC | AAACTTCCCA | GTTTATTATC | TAGTTTGTAA | TATTTCAAAA | CAATATTAAA | 720 |
| ATGAGACAGA | AATACAGAAT | TAAGTAAAAA | AGAAACAATG | TGGTTTACTT | TGTAAGAAAA | 780 |
| TTCTTAATGG | GGTAGAAAAG | ACTTGGAAAC | CATAAACAAA | GATAATAGAT | GATATAAAAG | 840 |
| AAAAAGTAGC | TTAGAGTGTA | CCAGTTGATA | ATGAAGCTCT | GGCTTAAAAA | TTAGTATATA | 900 |
| AAAGTATACT | AGTATGTAGT | ATATTTATAG | TATAGAAATG | AGTATAAAAA | CTAGTATAAT | 960 |
| TAGTATTAGT | ATATATTAGT | ATATTAGTAT | ATAAATTAGC | ATTGTAATTA | TACATTCGTA | 1020 |
| TATAAAATTA | TTATATATAT | TAGTAGATTA | GTAATAAAAC | TAGTAAAGTT | TATATTACTT | 1080 |
| ATAAATATA | GAAATGCTG | TGGGATCTTC | CCTATGTGTA | ATTATATATA | ATAGAGTGTT | 1140 |
| ATATTCTGTT | TCTGAACCCT | GACATAAAAA | TTTGGGAACT | TATAGTGGTC | TTAGGCAAAG | 1200 |
| TAAAATTAAT | AAAAACTTAA | TTAACATTCA | TAAAAAATCT | AGAAAAAATA | TTTGTTTTCT | 1260 |
| GTAATAGAAT | TATGTTCAAC | CTTCAAATAT | TGAAAAGAAC | ATCTCTCAAA | TAAATTAAAG | 1320 |
| ACTTTTTTGA | TGAAGTATTT | TAGTTCAAAA | ATTTAGTTCA | AAAATTGAGT | TTCAATATCT | 1380 |
| GAGAATGAAG | ATTTGAGTGG | CGAGTAATAT | TGTGGCACAA | ACATTATTTT | GAAATAAATT | 1440 |
| ACAAAAAAAT | GTAAGAACAC | ATAACAAGGA | GATGATTTAG | TATATTTTGG | TCAAAAATAT | 1500 |
| TAACATATAT | TTCACAAGAA | GAGGTAGTCC | CAAGCTTAGC | AGTGGGCAAG | AGGCTCTGAC | 1560 |
| CCCTTGGCGG | ATCATCAAGA | GAATCGTGTG | TACATTTCAA | TAAAGAGAAG | AGAAGAAGCC | 1620 |
| TAGTGTACAA | TATCTAAAGT | CATGTGGCAT | AAAGGAGAAC | AGACATTATT | AGCTATGTGG | 1680 |
| GGAAGATGAA | TATAAACGGA | GAAGAAACAA | ACTCAATAGT | CCAATAAAGT | CTCTGGATAG | 1740 |
| TGACACAAAT | AAGGAAAGTG | TTAAAATGAA | AACCTCAGTC | TTATTGGAAA | TGAGGAGAAA | 1800 |
| TAAACTAAAA | TAGTCATGGT | AACCGTTTAG | TGAAAAGAAA | AAAGGTAAAA | ATAAAATGTG | 1860 |
| ACTTTTTTGT | ACACATTTTC | TTGATCAGTC | TCTTCCAGTA | GAACTGAGGC | TCCATGAGGG | 1920 |
| AGTAATATCA | GGACTGTAAT | ATTTGTTCA | TTGCTGCGGT | CCTGGTCCCT | AGACAGTGTC | 1980 |
| TGGCAAGAAC | AGATTCTAAA | GAAATATTTT | TAAGTTAATG | AATAAATCTT | TTTTAAATT | 2040 |
| TTATTTGTCT | TTTTAAATTA | TTATTATTAT | ACTTTAAGTT | TTAGGGTACA | TGTGCACAAA | 2100 |

| | | | | | | |
|---|---|---|---|---|---|---|
| GTGCAGGTTT | GTTACATATG | TATACATGTG | CCATGTTGGT | GTGCTGCACC | CATTAACACG | 2160 |
| TCATTTAACA | TTAGGTATAT | CTCCTAATGC | TATCCCTCCC | CACTCCCCCC | ACCCCACAAC | 2220 |
| AGCCCCGGTG | TGTGATGTTC | CCCTTCCTGT | GTCCGTGTGT | TCCCATTGTT | CAATTCCCAC | 2280 |
| CTATGAGTGA | GAACATGTGG | TGTTTGGTTT | TTTTGTCCTT | GCGATAGTTT | GCTGAGAATG | 2340 |
| ATGGTTTCCA | GCTTCATCCA | TGTCCCTACA | AAGGACATGA | ACTCATCATT | TTTTATGGCT | 2400 |
| GCATAGTATT | CCATGGTGTA | TATGTGCCAC | ATTTTCTTAA | TCCAGTCTAT | CATTGTTGGA | 2460 |
| CATTTGGGTT | GGTTCCAAGT | CTTTGCTATT | GTGAATAGTG | CCGCAATAAA | CATACATGTG | 2520 |
| TATGTGTCTT | TATAGCAGCA | TGATTTATAA | TCCTTTGGGT | ATATACCCAG | TAATGGATGG | 2580 |
| CTAGGTCAAA | TGGTATCCTA | GCTCTAGATC | CCTGAGGAAT | CGCCACACTG | ACTTCCACAA | 2640 |
| TGGTTGAACT | AGTTACAGT | CCCACCAACA | GTGTAAAAGT | GTTCCTATTT | CTCCACATCC | 2700 |
| TCTCCAGCAC | CTGTTGTTTC | CTGACTTTTT | AATGATCGCC | ATTCTAACTG | GTGTGAGATG | 2760 |
| GTATCTCATT | GTGGTTTTGA | TTTGCATTTC | TCTGATGGCC | AGTGATGATG | AGCATTTTTT | 2820 |
| CATGTGATTT | TTGGCTGTAT | AAATGTCTTC | TTTTGAGAAG | TGTTTGTTCA | TATCCTTTGC | 2880 |
| CCACTTTTTG | ATGGGGTTGT | TTGTTTTTTC | TTGTAAATTT | GTTTGAGTTC | ATTGTAGATT | 2940 |
| CTGGATATTA | GCCCTTTGTC | AGATGAGTAG | ATTGCAAAAA | TTTTCTCTCA | TTCTGCAGGT | 3000 |
| TGCCTGTTCA | CTCTGATGGT | AGTTTCTTTT | GCTGTGCAGA | AGTTCTTTAG | TTTAATTAGA | 3060 |
| TCCCATTTGT | CAATTTTGGC | TTTTGTTGCC | ATTGCTTTTG | GTCTTTTACA | CATGAAGTCC | 3120 |
| TTGCCCATGC | CTATGTCCTG | AATGGTATTG | CCTAGGTTTT | CTTCTAGGGT | TTTTATGGTT | 3180 |
| TTAGGTCTGA | CATGTAAGTC | TTTAATCCAC | CTTGAATTAA | TTTTTGTATA | AGGTGTAAGG | 3240 |
| AAGGGACCCG | GTTCAGCTT | TCTACATATG | GCTAGCCAGT | TTTCCCAGCA | CCATTTATTA | 3300 |
| AATAGGGAAT | CCTTTCCCCA | TTGCTTGTTT | TTGTCAGCTT | TGTCAAAGAT | CAGATAGTTG | 3360 |
| TAGACATGCG | GCATTATTTC | TGAGGGCTCT | TTCCTGTTCC | ATTGGTCTTG | GTATCAGTTT | 3420 |
| TGGTACCAAG | TACCATGCTG | TTTTGGTTAC | TGTAGCCTTG | TAGTATAGTT | TGAAGTCAGG | 3480 |
| TAGCATGATG | CCTCCAGCTT | TGTTCTTTTG | GCTTAGGATT | TACTTGGCAA | TGTGGCCTCT | 3540 |
| TTTTTGGTTC | CATATGAACT | TTAAAGTAGT | TTTTTTCAAT | TCTGTGAAGA | AAGTCATTGG | 3600 |
| TAGCTTAATG | GGGATGGCAT | TGAATCTATA | AATTACCTTG | GGCAGTATGG | CCATTTTCAT | 3660 |
| GATATTGATT | CTTCCTACCC | ATGAGCATGG | AATGTTCTTC | CATTTGTTTG | TATCCTCTTT | 3720 |
| TATTTCATTG | AGCAGTGGTT | TGTAGTTCTC | CTTGGAGAGG | TCCTTCTCAT | CCCTTGTAAG | 3780 |
| TTGGATTCCT | AGGGATTTTA | TTCTCTTTGA | AGCAATTTTG | AATGGGAGTT | CACTCATGAT | 3840 |
| TTGGCTCTCT | GTTTGTCTGT | TATTGGTGTA | TATGAATGCT | TGTGATTTTT | GCACATTGAT | 3900 |
| TTTGTATCCT | GAGACTTTGC | TGAAGTTGCT | TATCAGCTTA | AGGAGACTTT | GGGCTGAGAC | 3960 |
| GATGGGGTTT | TCTAGATACA | CAGTCATGTC | ATCTGCAAAC | AGGGACAATT | TGACTTCCTC | 4020 |
| TTTTCCTAAT | TGAATGACCT | TTATTTCCTT | CTCCTGCCTA | ATTGCCCTGG | CCAGAACTTC | 4080 |
| CAACACTATG | TTGAATAGGA | GTGGTGAGAG | AGGGCATCCC | TGTCTTGTGC | CAATTTTTAA | 4140 |
| CGGGAATGCT | TCCAGTTTTT | GTCCATTCAG | TATGATATTG | GCTGTGGGTT | TGTCATAGAT | 4200 |
| AGCTCTTATT | ATTTGAGAT | ATGTCCCATC | AATACCTAAA | TTATTGAGAG | TTTTTAGCAT | 4260 |
| GAAGTGTTGT | TGAATTTTGT | CAAAGGCCTT | TTCTGCATCT | ATTGAGATAA | TCATGTGGTT | 4320 |
| TTTGTCTTTG | GTTTGTTTA | TATGCTGGAT | TACGTTTATT | GATTTTCGTA | TGTTGAACCA | 4380 |
| GCCTTGCATC | CCAGGGATGA | AGCCCACTTG | ATCATGGTGG | ATAAGCTTTT | TGATGTGTTG | 4440 |
| CATAAATCTT | TCCATACATA | TTTATAACTT | CTTTATGCCT | TTGAAAAAT | TCAATACTGT | 4500 |

```
AAATGGGACT TTTTTAAAAG TGGGGATAGA GTTGTTAGCT GAAAAATCTG AATAGCTGGC    4560
AATGAAGTTT GGAATTTGAA AAATGAGAAT CGCAAGCCAG AATGGATTTT GACCTCCTTC    4620
ATGTGATATA ACTTCTATTT AGTATTTATT CTATTTATTT TCTAAATGCA GATATTTTG     4680
TTATATATTA TCTCTCTTTT TTTTTGTTT TATAAAAAGT AACCTTACCT ACATAAGAAA     4740
GTATATCCAA TTGACCAATC TTCCACCATT CCATTTTTC TACATTCACA GGACTTAGTA     4800
GCC ATG AAG GTC CTC ATC CTC GCC TGC CTG GTG GCT CTT GCT CTT GCA      4848
    Met Lys Val Leu Ile Leu Ala Cys Leu Val Ala Leu Ala Leu Ala
    1               5                   10                  15
AGG GAG GTATGTGCAC AAGAAAAAAT TCCTAAACAA TCAATAAATA GTGGACTATA       4904
Arg Glu
TGCTTATTTG TAGAGAATAA CATCACCAAC ATTTTTACT GTATAAATAA TGAAGAATTT     4964
CATGAGAATT CTCTTGGCTT CTATCAAAAT CATTATATT TACCCACTGT CTCAACAGTT     5024
TCCTATAGTG CCCCAAATGC TTCCTGCACC AATGTGCTGC TAGTCACTAA AGAAAGAGCA    5084
AACAAATCAA TAAGTAATAA AAAATCATAA AAATGGCAAC GAAATATAAT ATTGCATAAA    5144
TACAACTCCA AAGATTCTCA AGCTAGATAA ATATATCTTA TTCCAGTGAT AAAATGTATA    5204
TATACCTTAC AGCCTAGGGC ACTGGGTCAA ATCCTGTGTC TGTCTGTACA AAGACATCCA    5264
TGGGATGAAG TACAGAGACA ATCATAATCA TGATCATAAA TATATTAATA ATAATATAAT    5324
AAAAATATTT AATACAAATT AAAGTGACTC TTCTTTTACC CATAAAAAAC TCTGTCTTTA    5384
ATAAATGTAA GATAAAAATA TATTAATAGA TTACTAAATA TAAAGACAT  TAAAGTAATT    5444
ACCTTTTAAA CCTCAAAAGT CATATAACAT TTTTTATTTC TCAAATTTGT GAAAGAGATA    5504
GCTCTGCATA AGTGATGTAA AAATTAAGTA GGATGCATGT TTAACAATGA GTTAGCTATA    5564
GAAGTTGAAT TTTTAAACAC CTTTTCAGAA GGAACAATCC AATGCATCCT CTGAGGTGAG    5624
ATTATTTTTT TAGAGAAAAT TTATGAACCA TAAAATAGTA AAATTCTCTA ATGATCTAGA    5684
AGATTTAGCT GGTTGTCAAT TTTTTTTTCC CACAG ACC ATA GAA AGC CTT TCA      5737
                                       Thr Ile Glu Ser Leu Ser
                                                        20
AGC AGT GAG GTAAGTTAAC ATTCTACCCA ATTTAGAAC AGTAAAATCC               5786
Ser Ser Glu
        25
TGTGCTATTT TTCTATGGTG TTACATCATG GCAGTTAAGC TAATGCAGCT ATGTTAATGA    5846
CATATAAGTT CTAGTACATA TTTCTTTTAT GTGTGTTTAA GGACAATAAG TATCTGGATA    5906
ATACAACATT CTAGAACTTT GTAAATTGGC TTGCTACTTG AAATTGTGTT ATTTTGCTTC    5966
TTTTTTTTT AATGAACCAT ATTGTCCTGT TTTCTGCCTT GAACTCTCTT TACTCTGAAC    6026
TTATTCACCT TAAGCATATA CTGACGGCCT TCTATGGGTC AGACATTGAC TAGGAGCTGT    6086
GGTACAAACT GAAAAGTTAG AGATGCCAGT GATAGTTAAG AGCTTGCTAA GTAGTAGGTA    6146
GGCAGACGTG CAAAAAGGAC ACATTTATA ATTACAATAG CCACTTTAGT AAATAAGCGA     6206
GATTAGTGT AGTCCTAAAT TTACCTGAGA GAGTCAGGTA GATATTTATT CTTACACCAC     6266
TCTTCTTGGG TGTGTGATCA CTTGATAAGT AAATGGTACA TCAATAGATT CTGTCTCTTC    6326
AGAAAGGTTA TATGATCCTT AAGGGAAGTG TTTAACTCTT ATGATTCATT TGAAGTGATC    6386
ATAATGTATC AATTGTTATT AGAATATATT TTCAATGAGT ATTTCTTTTT TTAAAAATCA    6446
GATGGGGTTT TAGATATCAT TTGTTGTCAG GGAATGAGCA TGGTGGTAGA GAGAAAATTA    6506
GCATCTATTA ATTGCTTTTT TTTGTACCAT GTCCTTCTTG ACTGCATTCA TCTGACTTTC    6566
TTTTACATAA CCAGCTCATA TAGAACAGTT TAATACATAA GTTTAATGAT TATACAAAGT    6626
TATTGATGAT ATTATCAAAG AATTAATGCC TTTATTTCCT GATTTATATT GCAAAGTAAG    6686
```

| | |
|---|---|
| AATTGTTAAA ACTAAACCTA ATTTTATATT TTTCTGTAG GAA TCT ATT ACA GAA<br>                                                                                Glu Ser Ile Thr Glu<br>                                                                                     30 | 6740 |
| TAC AAG GTAAATTTTC ACATTTAAAA TGTACACATT TTCAAAATTT CCTCCTTTTA<br>Tyr Lys | 6796 |
| ATCTTTACAG ATGGTAACAT ATCTTTATAT ATGATATATC TTTAGCAG AAA GTT GAG<br>                                                                                           Lys Val Glu<br>                                                                                              35 | 6853 |
| AAG GTT AAA CAT GAG GAC CAG CAG CAA GGA GAG GTAATTTGTT AATGATAAGT<br>Lys Val Lys His Glu Asp Gln Gln Gln Gly Glu<br>             40                           45 | 6906 |
| ATATGTTAA AATTATTATA AAGTATAATA CATACAAAAA TATTTATAAT GTGTATGTTG | 6966 |
| ATTCTAAAGA ATGATAATAA AATAAATGCC ATATACCCAC CAACCACTTT AAAAATTAAA | 7026 |
| CATTGATAAA GTCAATATAT TTTCTAGGAT ATGCATGCAT TTTTAAACTC ATAATTAATT | 7086 |
| TCTAGAATAC AGACTAAATA CATAATGATA TTACTAATGG TATATCTGTT TTCAACAAGT | 7146 |
| ACACATTGGT GGGAACATTT CCAGGTTGGG AACTATGATC CTCTTATTTC CAAGGTGGAT | 7206 |
| ATGGTAATGA AAAGGTGTAT ACGGCTGGTA AAAAACCTA TGTAAAATTT GTCCCATATT | 7266 |
| GCCTTTATTC CCATATGGAC AACACAAAAT CCTGTATTTC ATTAAATTAC ATTTATGGTG | 7326 |
| ATATGTTTAC CCAATTATAA TTTTCAATTG CTTTGTGTAC CAATGAATTG TTTGGAGTCA | 7386 |
| CATAAAATAT TTCTAAAATC AAATTTAAAC AAAAAAATTG ATGTCTCTTG AAAGACTGAA | 7446 |
| GAGACTATCT TCTCCAAGGG AAGGAATGTA AGAATTTGGC CGGTGTTAAA TTACTTCCTG | 7506 |
| AGATTAGCCA CAAATTAAGA CTGATTTTCT TTTTCATCAA ACCAAACAA AACAAAAATA | 7566 |
| AACCTTGGAA TTGTCCCTCT AAGTCTTTTT AAACTGAGTC TCTTTTCACT GTATGAAAAC | 7626 |
| AATTTGGTCT ACTATTGGCA CAACTGTGTT GAAAGTAAA TTCTCTCTGA AGACCAAAGT | 7686 |
| GTACAGCTAC AGCTATCCAG GCAATTCAGG AAAATGTTAA AAAAAGTGTT TCTGAAATAT | 7746 |
| CCAAACATTG ATTTCACTTT GGCCTGTGGA GTTACCCATG AAGTGAGTGG ATTAAAATTT | 7806 |
| TTCAACAAAC AGTTTACTCA TTTTTCTTCG CATGACTCAA GATACTTTCT TAACCAAAAT | 7866 |
| AAGTGAAATA TTTTCTCCTC TCTTTTACT CATTTATCAT TGTCTAAAAG AGAGAAATGA | 7926 |
| ATTCATTATG AATGGCAATT ATAGCTTAAT CAAGGACTCA AAGATTCTTT TTCCTTCTTT | 7986 |
| CCAG GAT GAA CAC CAG GAT AAA ATC TAC CCC TCT TTC CAG CCA CAG CCT<br>     Asp Glu His Gln Asp Lys Ile Tyr Pro Ser Phe Gln Pro Gln Pro<br>            50                         55                         60 | 8035 |
| CTG ATC TAT CCA TTC GTT GAA CCT ATC CCC TAT GGT TTT CTT CCA CAA<br>Leu Ile Tyr Pro Phe Val Glu Pro Ile Pro Tyr Gly Phe Leu Pro Gln<br>        65                             70                            75 | 8083 |
| AAC ATT CTG CCT CTT GCT CAG CCT GCT GTG GTG CTG CCT GTC CCT CAG<br>Asn Ile Leu Pro Leu Ala Gln Pro Ala Val Val Leu Pro Val Pro Gln<br>     80                           85                            90 | 8131 |
| CCT GAA ATA ATG GAA GTC CCT AAA GCT AAA GAC ACT GTC TAC ACT AAG<br>Pro Glu Ile Met Glu Val Pro Lys Ala Lys Asp Thr Val Tyr Thr Lys<br>95                        100                        105              110 | 8179 |
| GGC AGA GTG ATG CCT GTC CTT AAA TCT CCA ACG ATA CCC TTT TTT GAC<br>Gly Arg Val Met Pro Val Leu Lys Ser Pro Thr Ile Pro Phe Phe Asp<br>           115                        120                        125 | 8227 |
| CCT CAA ATC CCA AAA CTC ACT GAT CTT GAA AAT CTG CAT CTT CCT CTG<br>Pro Gln Ile Pro Lys Leu Thr Asp Leu Glu Asn Leu His Leu Pro Leu<br>            130                         135                        140 | 8275 |
| CCT CTG CTC CAG CCC TTG ATG CAG CAG GTC CCT CAG CCT ATT CCT CAG<br>Pro Leu Leu Gln Pro Leu Met Gln Gln Val Pro Gln Pro Ile Pro Gln<br>            145                         150                        155 | 8323 |
| ACT CTT GCA CTT CCC CCT CAG CCC CTG TGG TCT GTT CCT CAG CCC AAA | 8371 |

```
         Thr Leu Ala Leu Pro Pro Gln Pro Leu Trp Ser Val Pro Gln Pro Lys
             160             165             170
GTC CTG CCT ATC CCC CAG CAA GTG GTG CCC TAC CCT CAG AGA GCT GTG       8419
Val Leu Pro Ile Pro Gln Gln Val Val Pro Tyr Pro Gln Arg Ala Val
175             180             185                         190
CCT GTT CAA GCC CTT CTG CTC AAC CAA GAA CTT CTA CTT AAC CCC ACC       8467
Pro Val Gln Ala Leu Leu Leu Asn Gln Glu Leu Leu Leu Asn Pro Thr
                195             200             205
CAC CAG ATC TAC CCT GTG ACT CAG CCA CTT GCC CCA GTT CAT AAC CCC       8515
His Gln Ile Tyr Pro Val Thr Gln Pro Leu Ala Pro Val His Asn Pro
            210             215             220
ATT AGT GTAAGTCCAA ATTACTGGC TTTGCTGTTT CATTCAAGAT GTGTATGTGA         8571
Ile Ser
TGGTAGAATA AAAGAATAAA TGTAGAGTAA ATGAATTAAA AAAACAGTTT AGATAAGTGA     8631
TTCTTTTATT ATTATACTTT AAGTTTTAGG GTACATGTGC ACAACATGCA GGTTAGTTAC     8691
ATATGTATAC ATGTGCCATG TTGGTGTGCT GCACCCATTA ACTCGTCATT TAACATTCGG     8751
TATATCTCCT AATGCTATCC CATCCCCCAT CCCCCACCCC ACGACAGGTC CAGGTGTGTG     8811
ATGTTCCCCT TCCTGTGTCC ATGTGTTCTC ATAGATAAGT GATTCTTAAT GCTTACCTAT     8871
ACAATAGAAT CACCTGGAGA ACTTTTCCCC ACAAATCCCA ATGCCTAAGC TTACCCAGAG     8931
ATTCTGATAT AATTGTTCTA GTTTTTGTG TAGAGGAAAC TGAGTGTTGA GAAAAAAACT      8991
ATTGCATGAA TTCTGGTTTA ATTAGTCTGT TGAGAATTCT GATTAGATA AAGTAATTAA      9051
GGCTTACAAA AGCCGGAATT AAATTTAATA ATATGATTGA ATTTGGAAAA AAAAGCTAAA     9111
AAATGTTCTG TCATTTTCCT TGTGCACATC TCTTTTACAC AAGCCTTACT TCACATCTTG     9171
TTTTTGCTAT AAGTATATAT GAAGGCAAAA GACTGAGATG CTTATTTCAC TACTTACAAC     9231
ATTCTTAAGG CAAGTTTTCT TACTAAGAGG TTATTTATTT ATTATTTAT TTATTTATTT      9291
TACACAAGCC TTACTTCACA TCTGGTTTTT GCTGTAAATA TATATGAAGG CAAAAGACGG     9351
AGATGCTTAT TTCACTACTT ACAACATTCT TAAGGCAAGT TTCTTACTA AGAGGTTATT      9411
TATTTATTTG TATCTGTTTA TTTTTAAG GTC TAAGAAGATT TCAAAGTTAA              9462
                                Val
                                225
TTTTCCCTCC TTATTTTTGG TAAGTTTTGG GAGTTTGGAG ATTTAATTGA TCATTTTTAT     9522
ACATGATGTC TTTTTACATT TAATTCTCCT AGAGAAGTCC AATACAGTGA AAATTTCATA     9582
CATACAAGAA CTTTTTTTAT TAATTATCAA TTAATGGTT GACTATCATT TACTGACCTG      9642
AAACTATCTA TCTTTTGCAT TTCAAATAAC TTAATTTTA TTTATGTACT ATTGACAGAT      9702
TTGACTGGCT TGCTTTCAAG GGCCTATATA CTTACATTTG ATTATCACTA TTTTTAGGAA     9762
AGACAGAATA TATACTTATT TTACTTTTAT GGAAATATAT TTGAGCTTTT GTCAAAAGCC     9822
TATTTGCATT TTTATTTCTA ACCTAGCCTT CATAAAATTT GTATTACTT TACTTAAAAT      9882
TATCTTTTAA TTCATGAGTT AAAATTACTC CAAGTGTAAA GGTTAAAAAG AGGAGAGAAC     9942
AGCATTGCAA TTCTAAGATA TAAAGCCTTT TGGGATTATG AAATACCAGA CATTTCACTG     10002
AAACAATTTC AAGTTCACTA ATATTTGATG AACTTGGTG AAGTTTGGTG AACAAACTTT      10062
ACATGCCTCC AAACCGCAAC AGAATGCATT TGCAATACAA TTTCTTTTGT GAATTAGTCA     10122
CACCAAAGTT AAAAGTGAAG AGAGTTGAAT AGTTACGTGT TATAACATAA CTAATTATAT     10182
ATTTGCTCTC TATTCCACAG AATTGACTGA GACTGGAAAT ATGATGCCTT TTCCGTCTTT     10242
GTATCACGTT ACCCCAAATT AAGTATGTTT GAATGAGTTT ATATGGAAAA AATGAACTTT     10302
GTCCCTTTAT TTATTTTATA TATTATGTCA TTCATTTAAT TTGAAATTTG ACTCATGAAC     10362
```

```
TATTTACATT TTCCAAATCT TAATTCAACT AGTACCACAG AAGTTCAATA CTCATTTGGA    10422

AATGCTACAA ACATATCAAA CATATGTATA CAAATTGTTT CTGGAATTGT GCTTATTTTT    10482

ATTTCCTTAA GAATCTATTT CCTTTCCAGT CATTTCAATA AATTATTCTT AAGCATATTT    10542

CAGTTCTTCT GTCTTTTTTT CAAACCTAAT CGGCCTCTTT AATGTTAACT TGGTTTATTA    10602

TTAGG                                                                10607
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ser Thr Thr Glx Ala Asx His
1                5
```

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Val Pro Tyr Pro Gln Arg Ala
1                5
```

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:6:

```
GAGCAAGGGA AGAGGCAAAT GAAGATTTTC AAGATCAGTC AA                         42
```

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:7:

```
GTTGGGTAAC GCCAGGGTTT TC                                              22
```

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

```
CAGGAAACAG CTATGAC                                                    17
```

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTCCGGCTCG TATGTTGTGT GG                                    22

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CTCGAGCGAA GAATCGATCA CCGAA                                 25

( 2 ) INFORMATION FOR SEQ ID NO:11:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GAATTCATAT GCGTGAAACC ATCGAATCCC TGAG                       34

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TACAAAAAAG TTGAAAAAGT TAAACACGAG GACCAG                     36

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CTTTTTTGTA TTCGGTGATC GATTCTTCGC TCGAGCTCAG GGATT           45

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GATCCTGGTC CTCGTGTTTA ACTTTTTCAA                            30

-continued ( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CGATGGTTTC ACGCATATGA ATTCTGCA 28

( 2 ) INFORMATION FOR SEQ ID NO:16:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CCAGTTCATA ACCCCATTAG TGTCTAATAA GGATCCG 37

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GATCTACCCT GTGACTCAGC CACTTGCC 28

( 2 ) INFORMATION FOR SEQ ID NO:18:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AATTCGGATC CTTATTAGAC ACTAATGG 28

( 2 ) INFORMATION FOR SEQ ID NO:19:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGTTATGAAC TGGGGCAAGT GGCTGAGTCA CAGGGTA 37

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

TATGCACGTG AAACCATCGA ATCCCTGAGC 30

( 2 ) INFORMATION FOR SEQ ID NO:21:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (xi) SEQUENCE DESCRIPTION: SEQ ID NO:21:

TCGAGCTCAG GGATTCGATG GTTTCACGTG CA     32

(2) INFORMATION FOR SEQ ID NO:22:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO:22:

CGGGTACCCT AAAGGACTTG ACAGCCATGA AGGTCCTCAT CCTCGCCTGC CTGG     54

(2) INFORMATION FOR SEQ ID NO:23:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (xi) SEQUENCE DESCRIPTION: SEQ ID NO:23:

CGGTCGACTT AGACACTAAT GGGGTTATGA ACTG     34

(2) INFORMATION FOR SEQ ID NO:24:

(i) SEQUENCE CHARACTERISTICS:
    (A) LENGTH: 708 base pairs
    (B) TYPE: nucleic acid
    (C) STRANDEDNESS: single
    (D) TOPOLOGY: linear (xi) SEQUENCE DESCRIPTION: SEQ ID NO:24:

GGTACCCTAA AGGACTTGAC AGCCATGAAG GTCCTCATCC TCGCCTGCCT GGTGGCTCTT     60
GCTCTTGCAA GGGAGACCAT AGAAAGCCTT TCAAGCAGTG AGGAATCTAT TACAGAATAC    120
AAGAAAGTTG AGAAGGTTAA ACATGAGGAC CAGCAGCAAG GAGAGGATGA ACACCAGGAT    180
AAAATCTACC CCTCTTTCCA GCCACAGCCT CTGATCTATC CATTCGTTGA ACCTATCCCC    240
TATGGTTTTC TTCCACAAAA CATTCTGCCT CTTGCTCAGC CTGCTGTGGT GCTGCCTGTC    300
CCTCAGCCTG AAATAATGGA AGTCCCTAAA GCTAAAGACA CTGTCTACAC TAAGGGCAGA    360
GTGATGCCTG TCCTTAAATC TCCAACGATA CCCTTTTTTG ACCCTCAAAT CCCAAAACTC    420
ACTGATCTTG AAAATCTGCA TCTTCCTCTG CCTCTGCTCC AGCCCTTGAT GCAGCAGGTC    480
CCTCAGCCTA TTCCTCAGAC TCTTGCACTT CCCCCTCAGC CCTGTGGTC TGTTCCTCAG    540
CCCAAAGTCC TGCCTATCCC CCAGCAAGTG GTGCCCTACC CTCAGAGAGC TGTGCCTGTT    600
CAAGCCCTTC TGCTCAACCA AGAACTTCTA CTTAACCCCA CCACCAGAT CTACCCTGTG    660
ACTCAGCCAC TTGCCCCAGT TCATAACCCC ATTAGTGTCT AAGTCGAC              708

HUMAN β-CASEIN, PROCESS FOR PRODUCING IT AND USE THEREOF

This application is a continuation-in-part of both PCT/DK92/00026, filed on Aug. 19, 1992, and PCT/DK91/00233, filed on Aug. 19, 1991, both now pending, hereby incorporated by reference.

The present invention relates to a DNA sequence encoding the human milk protein β-casein. More specifically, the DNA sequence encodes a polypeptide having the amino acid sequence shown in SEQ ID NO: 2. The DNA sequence is advantageously used in the production of recombinant human β-casein, either by means of a prokaryotic or an eukaryotic production system, or more advantageously by means of production in transgenic non-human mammals such as bovine species. The main use of the recombinant human β-casein is as a constituent of infant formulae used for feeding infants as a substitute for human milk. When used as a constituent of infant formulae, it is contemplated that the recombinant human β-casein provides a substantial improvement of the nutritional and biological value of the formulae in that a closer similarity to human milk is obtained.

BACKGROUND OF THE INVENTION

It is well known that human milk-feeding is considered superior to formula-feeding for infants. Not only does human milk provide a well-balanced supply of nutrients, but it is also easily digested by the infant. Thus, several biologically active components which are known to have physiological functions in the infant are either a constituent of human milk or produced during the digestion thereof, including components involved in the defense against infection and components facilitating the uptake of nutrients from human milk.

In spite of the great efforts which have been invested in preparing infant formulae, it has not been possible to produce a formula which to any substantial extent has the advantageous properties of human milk. Thus, infant formula, often prepared on the basis of cow milk, is generally incompletely digested by the infant and is lacking substances known to have effect on the physiological functions of the infant. In order to obtain an infant formula with a nutritional value similar to human milk, a number of additives including protein fragments, vitamins, minerals etc., which are normally formed or taken up during the infant's digestion of human milk, are included in the formula with the consequent risk of posing an increased strain on and possible long-term damage of important organs such as liver and kidney. Another disadvantage associated with the use of cow milk-based formulae is the increased risk for inducing allergy in the infant against bovine proteins.

As an alternative to cow milk-based infant formulae, human milk obtainable from so-called milk banks has been used. However, feeding newborn infants with human milk from milk banks has in the recent years to an increasing extent been avoided, because of the fear for the presence of infective agents such as HIV and CMV in human milk. In order to destroy the infective agents in human milk it has become necessary to pasteurize the milk before use. However, by pasteurization the nutritional value and the biological effects of the milk components are decreased and human milk is used to a still lesser extent.

Presently, commercially available human infant formula used to replace mother's milk is based primarily upon the protein constituents of cow's milk. These infant formula compositions have led to difficulties in terms of nutrient balance, bioavailability of nutrients and sensitivity of human infants to non-human/animal protein. Specifically, allergic reactions to the non-human animal protein used with these infant formulas caused a change in the protein component of the commercially available formula to soy-protein based formulas, although many infants that are allergic to cow's milk are also allergic to soy-based milks (Am. Acad. of Pediatrics Comm. on Nutrition, *Pediatrics* 72, 359–363 (1983)).

Additionally, many of the problems with the use of cow's milk protein are associated with difficulties in digestibility because of bovine casein content and structure (L. Hambraeus, E. Forsum and B. Lonnerdal. In: "Food and Immunology", pp. 116–124 (Eds. L. Hambraeus, L. A. Hanson and H. McFarlane) Almquist and Wiksell (1977)).

This has led to the production of infant formulas which contain a greater proportion of whey protein, since it is more readily digested by human infants (M. J. Newport and M. J. Henschel, *Pediatric Res.* 18, 658–662 (1984)), and little or no bovine casein. However, the major protein in whey of cow's milk is β-lactoglobulin. This protein is essentially absent from human milk and has been determined to be one of the main causes of cow's milk allergy in infants (I. Axelsson, I. Jakobsson, T. Lindberg and B. Benediktsson, *Acta Pediatrica Scand.* 75, 702–707 (1986)). The extent of the problems with allergies to formulas based on cow's milk may be appreciated from the fact that soy-based formulas now comprise a large portion of the human infant formula market in the United States.

Soy-protein formulas, although different in carbohydrate and protein source, are similar in composition to cow's milk protein formulas following the American Academy of Pediatrics, Committee on Nutrition recommendations for nutrient levels in infant formulas. Differences include a slightly higher protein level and slightly lower carbohydrate content. The protein source is generally soy-protein; the fat is a blend of vegetable oils; and the source of carbohydrate is usually sucrose, corn syrup solids, or a mixture of both. However, the use of soy formulas tends to raise serum alkaline phosphatase and blood urea levels in infants in addition to causing the allergic and digestibility problems encountered with the use of bovine-based protein infant formulas.

Human milk differs markedly from that of other mammalian species, including cows, in that it contains a lower over-all protein content and lower ratio of casein/whey as well as a different protein composition. For instance, the casein subclasses of human milk comprise only β-casein and κ-casein, whereas the bovine casein subclasses are α-casein, β-casein, and κ-casein (Miller et al.). Also the amino acid sequences of human milk protein differ from that of other mammalian milk proteins.

β-Casein is a phosphorylated protein which is present in milk of several species, including humans in which it is the major casein subunit. This protein—or its digested fragments—is believed to enhance calcium absorption by chelating calcium to its phosphorylated residues and thereby keeping it in an absorbable form. Human β-casein is easily digested by newborn infants and the digestive products have been found to play an important role in the calcium uptake, and thus in the mineralization of the skeleton. A digestion product (β-casomorphin) of human β-casein has been found to have opioid activity and may be involved in the sleeping patterns of breast-fed infants.

It would be desirable to be able to prepare an infant formula with a composition closer to that of human milk and thus avoid the above disadvantages associated with bovine milk-based infant formula, e.g. a formula comprising human milk proteins. However, this would require that human milk proteins are obtainable in large quantities. Although human milk proteins may be purified directly from human milk, this is not a realistic and sufficiently economical way to obtain the large quantities needed for large scale formula production, and other methods must be developed before an infant formula comprising human milk proteins may be prepared.

So far, little detailed characterization of human milk proteins, e.g. in terms of amino acid sequences, has been made. Greenberg et al. reported the isolation and purification of native human β-casein and the amino acid sequence thereof. The total composition of the native human β-casein was stated to be 212 amino acids and various phosphorylation sites were identified in the sequence.

Several milk protein genes, primarily from rodents or dairy animals, have been cloned and sequenced (cf. Bonsing and Mackinlay; Hall et al.; Blackburn and Rosen; Jones et al.; Yoshimura et al.; Yoshimura and Oka; Menon and Ham; Stewart et al.; Prorot et al.; Devinoy et al.; Schaefer et al.), but knowledge of the genes encoding human milk proteins is still sparse. Recently, Menon and Ham disclosed the isolation and sequencing of a partial cDNA clone encoding human β-casein. The clone included the coding sequence corresponding to amino acid residues 146–212 of the mature protein and the entire 3' non-coding region. The deduced partial amino acid sequence was compared with the sequence of the native protein reported by Greenberg et al. and several amino acid differences were found between the two amino acid sequences. Menon and Ham have not, however, succeeded in isolating the entire cDNA encoding human β-casein, nor in providing a DNA sequence useful for the production of a polypeptide comprising a substantial part (of more than 67 amino acid residues) of the human β-casein sequence. This is accomplished and described for the first time by the present inventors (Lönnerdal et al., published on 20 Aug., 1990, which is hereby incorporated by reference).

SUMMARY OF THE INVENTION

It is an object of the present invention to provide a means for producing recombinant human β-casein in a high yield and at a realistic price.

Accordingly, in one aspect the present invention relates to a DNA sequence encoding a polypeptide comprising the amino acid sequence shown in SEQ ID NO: 2 or an analogue of said DNA sequence which 1) hybridizes with the DNA sequence shown in SEQ ID NO: 1 or a specific part thereof under the stringent hybridization conditions or 2) encodes a polypeptide, the amino acid sequence of which is at least 85% homologous with the amino acid sequence shown in SEQ ID NO: 2, or 3) constitutes an effective subsequence of said DNA sequence, which encodes a polypeptide having the calcium binding activity of human β-casein, or having opioid activity, or having angiotensin converting enzyme (ACE) inhibitory activity, or a polypeptide having a combination of any of these activities.

One DNA sequence of the invention was determined on the basis of a cDNA clone isolated from a human mammary gland cDNA library using hybridization with a specific 42-mer oligonucleotide probe prepared on the basis of amino acid residues 117–130 of the human β-casein sequence as disclosed by Greenberg et al. The procedure used for isolating the human β-casein cDNA sequence is outlined in Example 1 below.

The stringent hybridization conditions referred to above are to be understood in their conventional meaning, i.e. that hybridization is carried out at 67° C. in 2×SSC and final washing at 67° C. in 1×SSC using the method specified in the "Definition" part of the Examples below.

In one aspect the present invention relates to an expression system comprising a DNA sequence encoding a polypeptide having the amino acid sequence SEQ ID NO:2 or an analogue or variant thereof which has either the calcium binding activity of human β-casein, or opioid activity, or angiotensin converting enzyme (ACE) inhibitory activity, or a combination of any two or three of these activities, the system comprising a 5'-flanking sequence capable of mediating expression of said DNA sequence.

A transgenic cell or animal contains one or more transgenes within its genome. A transgene is a DNA sequence integrated at a locus of a genome, wherein the transgenic DNA sequence is not otherwise normally found at that locus in that genome. Transgenes may be made up of heterologous DNA sequences (sequences normally found in the genome of other species) or homologous DNA sequences (sequences derived from the genome of the same species). Transgenic animals have been reported. For example, U.S. Pat. No. 4,736,866 discloses a transgenic mouse containing a c-myc oncogene. Other reports of transgenic animals include PCT Publication No. WO 82/04443 (rabbit β-globin gene DNA fragment injected into the pronucleus of a mouse zygote); EPO Publication No. 0 264 166 (Hepatitis B surface antigen and Tissue Plasminogen Activator genes under control of the whey acid protein promoter for mammary tissue specific expression); EPO Publication No. 0 247 494 (transgenic mice containing heterologous DNA encoding various forms of insulin); PCT Publication No. WO 88/00239 (tissue specific expression of DNA encoding factor IX under control of a whey protein promoter); PCT Publication No. WO 88/01648 (transgenic mammal having mammary secretory cells incorporating a recombinant expression system comprising a mammary lactogen-inducible regulatory region and a structural region encoding a heterologous protein); EPO Publication No. 0 279 582 (tissue specific expression of chloramphenicol acetyltransferase under control of rat β-casein promoter in transgenic mice); and WO 91/08216 (production of recombinant polypeptides by bovine species and transgenic methods).

As used herein, a "recombinant polypeptide" (or the recombinant DNA sequence encoding the same) is a "heterologous polypeptide". Heterologous polypeptides are polypeptides which are not normally produced by the transgenic animal. Examples of heterologous polypeptides include human milk proteins such as human β-casein.

Each of the heterologous or homologous polypeptides are characterized by specific amino acid and nucleic acid sequences. It is to be understood, however, the such sequences include naturally occurring allelic variations thereof and variants produced by recombinant methods wherein such nucleic acid and polypeptide sequences have been modified by the substitution, insertion and/or deletion of one or more nucleotides in such nucleic acids to cause the substitution, insertion or deletion of one or more amino acid residues in the recombinant polypeptide.

The term "homologous" is used here to illustrate the degree of identity between the amino acid sequence of a given polypeptide and the amino acid sequence shown in SEQ ID NO: 2. The amino acid sequence to be compared with the amino acid sequence shown in SEQ ID NO: 2 may be deduced from a DNA sequence, e.g. obtained by hybridization as defined above, or may be obtained by conventional amino acid sequencing methods. The degree of homology is preferably determined on the amino acid sequence of a mature polypeptide, i.e. without taking any leader sequence into consideration. It is preferred that the degree of homology is at least 85%, such as at least 90%, preferably at least 95% or even 98% with the amino acid sequence shown in SEQ ID NO: 2.

The term "effective subsequence" as used above refers to a subsequence which encodes a peptide being at least partially functional with respect to the activities of human β-casein as defined above. The subsequence may be the result of a truncation at either end of the DNA sequence or of the removal of one or more nucleotides or nucleotide sequences within DNA sequence. Preferably, when encoding a peptide having the opioid or the ACE-inhibitory activity of human β-casein, the effective subsequence comprises at least 15 nucleotides such as at least 20 nucleotides.

The term "calcium-binding activity" denotes the capability of the polypeptide of the invention to bind calcium and may be determined by equilibrium dialysis or a similar technique. The term is to be understood in the sense that the polypeptide in question is capable of binding calcium by the same or substantially the same mechanism as human β-casein; however, the term does not necessarily indicate that the binding is quantitatively the same, considering, inter alia, that the calcium binding capability is dependent on the degree of phosphorylation, which, on its side, may differ considerably dependent on the species in which the recombinant polypeptide is produced. The term "opioid activity" denotes the peptide's opiate-like effects and capability of the peptide to bind to opiate receptors (opiate receptor affinity). The "opioid activity" is determined as disclosed by Brantl, 1984 and Migliori-Samour et al. The term "ACE-inhibitory activity" denotes the capability of the peptide to inhibit the angiotensin converting enzyme (ACE) and has important indications for the treatment of heart disorders. The ACE-inhibitory effect is determined by use of a method as disclosed by Maruyama et al. and Kohmura et al.

In this connection, it should be noted that the terms "calcium-binding activity", "opioid activity" and "ACE-inhibitory activity" and related terms should be understood to be qualitative and/or quantitative that is, relating first of all to the nature of the activity, such as the nature of the calcium binding activity, and/or to the level of activity of the polypeptide as determined with reference to human β-casein. Concerning the ACE-inhibitory effect or the opioid effect, these are also of the same qualitative nature as ascribed in the literature to digestive fragments of human β-casein having ACE-inhibitory activity or opioid activity, respectively.

In this connection the term "digestive fragment" refers to the peptide fragment(s) which, in nature, are generated during the digestion of human β-casein by the infant fed on human milk. Such fragments may be prepared, e.g. by cleavage of recombinant human β-casein, by expression from DNA sequences encoding such fragments, or by use of conventional peptide synthesis.

In another aspect the present invention relates to a polypeptide produced by the DNA sequence of the invention, preferably a recombinant human β-casein protein having the amino acid sequence shown in SEQ ID NO: 2 or an analogue or a variant thereof having the calcium-binding activity of human β-casein or a subsequence of the amino acid sequence shown in SEQ ID NO: 2 or an analogue or variant having ACE-inhibitory activity or opioid activity of a digestive fragment of human β-casein. The variant and the subsequence is further defined below.

In further aspects, the present invention relates to a DNA sequence encoding a polypeptide as defined herein, a replicable expression vector which carries and is capable of expressing such DNA sequence, a cell harbouring such a vector, a method for producing the polypeptide, a method for producing a transgenic non-human animal capable of expressing the polypeptide, such a transgenic animal per se, milk from such a transgenic animal, an infant formula comprising a polypeptide as defined herein, a method of isolating a polypeptide as defined herein, and the polypeptide proper.

In yet another aspect the present invention provides a mammalian expression system comprising a DNA sequence encoding human β-casein inserted into a gene encoding a milk protein of a non-human mammal so as to form a hybrid gene which is expressible in the mammary gland of an adult female of a mammal harbouring said hybrid gene so that human β-casein is produced when the hybrid gene is expressed.

In yet a further aspect, the present invention relates to a method of producing a transgenic non-human mammal capable of expressing human β-casein, comprising injecting a mammalian expression system as defined above into a fertilized egg or a cell of an embryo of a mammal so as to incorporate the expression system into the germline of the mammal and developing the resulting injected fertilized egg or embryo into an adult female mammal.

DETAILED DESCRIPTION OF THE PRESENT INVENTION

An interesting DNA sequence translatable into a human β-casein polypeptide is a sequence comprising a human β-casein gene. Accordingly, in a further aspect, the present invention relates to a DNA sequence comprising a human β-casein gene or an effective subsequence thereof containing elements capable of expressing a polypeptide having the activity of human β-casein or a digestive fragment thereof, or an analogue of said DNA sequence which 1) hybridizes with the DNA sequence shown in SEQ ID NO: 1 or a specific part thereof under stringent hybridization conditions or 2) encodes a polypeptide, the amino acid sequence of which is at least 85% homologous with the amino acid sequence shown in SEQ ID NO: 2, or 3) constitutes an effective subsequence of said DNA sequence, which encodes a polypeptide having the calcium binding activity of human β-casein, or opioid activity, or angiotensin converting enzyme (ACE) inhibitory activity or a combination of any two or three of these activities.

The expression system according to the invention may be an expression system comprising a 5'-flanking sequence from a milk protein gene of a mammal and a DNA sequence encoding a polypeptide having the amino acid sequence SEQ ID NO: 2 or an analogue or variant thereof which has either the calcium binding activity of human β-casein, or opioid activity, or angiotensin converting enzyme (ACE) inhibitory activity, or a combination of any two or three of these activities, the 5'-flanking sequence being capable of mediating expression of the polypeptide.

As discussed in detail in the following, the expression system according to the invention is, for many purposes, preferably an expression system in which the DNA sequence contains at least one intron sequence, and, preferably, contains at least one permissive RNA splice signal.

In a preferred embodiment, the expression system according to the invention is one in which the DNA sequence is inserted into a milk protein gene of a non-human mammal so as to form a hybrid gene which is expressible in the mammary gland of an adult female of a non-human mammal harbouring said hybrid gene so that the polypeptide encoded by the DNA sequence is produced when the hybrid gene is expressed. As an example, the milk protein gene may be one selected from whey acidic protein (WAP) genes.

As mentioned above, the expression system is preferably wherein the analogue or variant of the polypeptide encoded is at least 85% homologous with the amino acid sequence SEQ ID NO: 2. Another way of expressing the close structural relationship with the DNA sequence SEQ ID NO: 1 or with the DNA sequence SEQ ID NO: 3 is to refer to hybridization: The expression system is preferably such that the DNA sequence encoding the polypeptide is one which hybridizes with the DNA sequence SEQ ID NO: 1 or with the DNA sequence SEQ ID NO: 3 or with a part thereof under stringent hybridization conditions.

A particularly interesting expression system according to the invention is one which encodes a polypeptide comprising, or substantially being, amino acid sequence 1–210 shown in FIG. 1 corresponding to amino acid sequence 1–210 of SEQ ID NO: 2.

The cDNA sequence shown in FIG. 1 (and in SEQ ID NO: 1) has an overall length of 1065 bp, including the poly(A) tail. The open reading frame begins from the first nucleotide "A" at the 5'-end and codes for a signal peptide of 15 amino acids and the mature casein consisting of 210 amino acid residues. The coding cDNA of human β-casein is flanked by one 390 bp non-coding region at the 3'-terminal end and one of 48 bp at the 5'-terminus. The size of the human β-casein cDNA shown in FIG. 1 is similar to that of ovine β-casein (Prorot et al.).

The amino acid sequence deduced from the nucleotide sequence shown in FIG. 1, which is listed as SEQ ID NO: 2, shows some discrepancies compared to that reported by Greenberg et al. Thus, the deduced amino acid sequence is constituted by 210 amino acid residues and no codons for the amino acids at positions 19 and 207 of the 212 amino acid sequence reported by Greenberg et al. are found. Other discrepancies are found at positions 15 (Thr instead of Pro), 32 (Gly vs. Thr), 34 (Glu vs. Gln), 104 (Ser vs. Gln), 133 (Leu vs. Ser), 158 (Gln vs. Glu), 167 (Gln vs. Glu), 169 (Val vs. Leu), 173 (Gln vs. Val), 192 (Thr vs. Pro), 198 (Thr vs. Pro), 199 (Gln vs. Glu), and 201–206 (Leu-Ala-Pro-Val-His-Asn) (SEQ ID NO: 2; residues 216–221) vs. Ser-Thr-Thr-Glx-Ala-Asz-His (SEQ ID NO: 4).

A relatively large degree of homology, 45–62%, is found between human β-casein and the corresponding proteins from other species. Furthermore, the 15 residues signal peptide of human β-casein is identical to those of bovine, ovine and rabbit β-caseins and, except for 1 residue, identical to those of rat and mouse β-caseins. By comparison between the DNA sequences encoding β-casein of different origins, single base substitutions between species, which usually occur at the wobble position and thus code for the same amino acid, have been found.

A consensus polyadenylation recognition signal AAUAAA is located 16 nucleotides upstream from the poly(A) tail. An 11 nucleotides long motif (bp 823–833; TTTATTTATTT) (SEQ ID NO: 3, nucleotides 9265–9275 and 9277–9287) which might be involved in the stabilization of the mRNA, is also found and corresponds to a sequence found in connection with β-casein genes of other origins (Prorot et al.).

An interesting DNA sequence translatable into a human β-casein polypeptide is a sequence comprising a human β-casein gene. Accordingly, in a further aspect, the present invention relates to a DNA sequence comprising a human β-casein gene or an effective subsequence thereof.

This aspect of the invention relates, inter alia, to a DNA sequence encoding a polypeptide having the amino acid sequence SEQ ID NO:2 or an analogue or variant thereof which has either the calcium binding activity of human β-casein, or opioid activity, or angiotensin converting enzyme (ACE) inhibitory activity, or a combination of any two or three of these activities, the DNA sequence comprising at least one intron sequence; the DNA sequence preferably contains at least one permissive RNA splice signal.

In a preferred embodiment, the DNA sequence comprises substantially the DNA sequence shown in SEQ ID NO:1. Alternatively, the DNA sequence may comprise one or several parts of the DNA sequence shown in SEQ ID NO:3, i.e. include at least a part of one or several intron regions. A DNA sequence of the invention may also be a modified DNA sequence which differs from a DNA sequence as defined above in that at least one nucleotide has been deleted, substituted or modified or at least one additional nucleotide has been inserted so as to result in a DNA sequence which encodes a polypeptide having a calcium-binding which is similar to, increased or decreased as compared to the calcium-binding activity of human β-casein, or a polypeptide having ACE-inhibitory activity, or a polypeptide having opioid activity.

In the present context, the term "gene" is used to indicate a DNA sequence which is involved in producing a polypeptide chain and which includes regions preceding and following the coding region (5'-upstream and 3'-downstream sequences) as well as intervening sequences, introns, which are placed between individual coding segments, exons, or in the 5'-upstream or 3'-downstream region. The 5'-upstream region comprises a regulatory sequence which controls the expression of the gene, typically a promoter. The 3'-downstream region comprises sequences which are involved in termination of transcription of the gene and optionally sequences responsible for polyadenylation of the transcript and the 3' untranslated region.

The above mentioned regulatory or expression regulation sequences in addition to controlling transcription also contribute to RNA stability and processing, at least to the extent they are also transcribed.

Such expression regulation sequences are chosen to produce tissue-specific or cell type-specific expression of the recombinant DNA. Once a tissue or cell type is chosen for expression, 5' and optional 3' expression regulation sequences are chosen. Generally, such expression regulation sequences are derived from genes that are expressed primarily in the tissue or cell type chosen. Preferably, the genes from which these expression regulation sequences are obtained are expressed substantially only in the tissue or cell type chosen, although secondary expression in other tissue and/or cell types is acceptable if expression of the recombinant DNA in the transgene in such tissue or cell type is not detrimental to the transgenic animal. Particularly preferred expression regulation sequences are those endogenous to the species of animal to be manipulated. However, expression regulation sequences from other species such as those from human genes may also be used. In some instances, the expression regulation sequences and the structural DNA sequences (either genomic or cDNA) are from the same species, e.g. each from bovine species or from a human source. In such cases, the expression regulation sequence and the DNA sequence are homologous to each other. Alternatively, the expression regulation sequences and DNA sequences (either cDNA or genomic) are obtained from different species, e.g. an expression regulation sequence from bovine species and a DNA sequence from a human source. In such cases, the expression regulation and DNA sequence are heterologous to each other. The following defines expression regulation sequences from endogenous genes. Such definitions are also applicable to expression regulation sequences from non-endogenous, heterologous genes.

In general, the 5' expression regulation sequence includes the transcribed portion of the endogenous gene upstream from the translation initiation sequence (the 5' untranslated region or 5' UTR) and those flanking sequences upstream therefrom which comprise a functional promoter. As used herein, a "functional promoter" includes those necessary untranscribed DNA sequences which direct the binding of RNA polymerase to the endogenous gene to promote transcription. Such sequences typically comprise a TATA sequence or box located generally about 25 to 30 nucleotides from the transcription initiation site. The TATA box is also sometimes referred to as the proximal signal. In many instances, the promoter further comprises one or more distal signals located upstream from the proximal signal (TATA box) which are necessary to initiate transcription. Such promoter sequences are generally contained within the first 100 to 200 nucleotides located upstream from the transcription initiation site, but may extend up to 500 to 600 nucleotides or more from the transcription initiation site. Such sequences are either readily apparent to those skilled in the art or readily identifiable by standard methods. Such promoter sequences alone or in combination with the 5' untranslated region are referred to herein as "proximal 5' expression regulation sequences".

In addition to such proximal 5' expression regulation sequences, it is preferred that additional 5' flanking sequences (referred to herein as "distal 5' expression regulation sequences") also be included in the transgene. Such distal 5' expression regulation sequences are believed to contain one or more enhancer and/or other sequences which facilitate expression of the endogenous gene and as a consequence facilitate the expression of the structural DNA sequence operably linked to the distal and proximal 5' expression regulation sequences. These 5' expression regulation sequences regulate the spatial and temporal distribution of gene expression. The amount of distal 5' expression regulation sequences depends upon the endogenous gene from which the expression regulation sequences are derived. In general, however, such sequences comprise 5' flanking regions of approximately 1 kb, more preferably 16 kb and most preferably about 30 kb of 5' flanking sequence. The determination of the optimal amount of distal 5' expression regulation sequences used from any particular endogenous gene is readily determined by varying the amount of distal 5' expression regulation sequence to obtain maximal expression. In general, the distal 5' expression regulation sequence will not be so large as to extend into an adjacent gene and will not include DNA sequences which adversely effect the level of transgene expression.

In addition, it is preferred that 3' expression regulation sequences also be included to supplement tissue or cell-type specific expression. Such 3' expression regulation sequences include 3' proximal and 3' distal expression regulation sequences from an appropriate endogenous gene. The 3' proximal expression regulation sequences include transcribed but untranslated DNA positioned downstream from the translation stop signal in the recombinant DNA sequence (also referred to as the 3' untranslated region or 3' UTR). Such sequences generally terminate at a polyadenylation sequence (either from the endogenous gene or from other sources such as SV40) and sequences that may affect RNA stability. Generally, 3' UTR's comprise about 100 to 1000 nucleotides or more downstream from the translation stop signal in the gene from which the 3' regulation sequence is derived. Distal 3' expression regulation sequences include flanking DNA sequences downstream from the proximal 3' expression regulation sequence. Some of these distal sequences are transcribed, but do not form part of the mRNA while other sequences in this 3' distal expression regulation sequence are not transcribed at all. Such distal 3' expression regulation sequences are believed to contain enhancer and/or other sequences which enhance expression. Such sequences are believed to be necessary for efficient polyadenylation and contain transcription termination sequences. Preferably, such sequences comprise about 2 kb, more preferably 8 kb and most preferably about 15 kb of 3' flanking sequence.

Although the use of both 5' and 3' expression regulation sequences are preferred, in some embodiments of the invention, endogenous 3' regulation sequences are not used. In such cases, the 3' proximal expression regulation sequences normally associated with the genomic DNA encoded by the recombinant DNA sequence are used to direct polyadenylation. In addition, distal 3' regulation sequences from the genomic DNA encoding the recombinant polypeptide may also be employed preferably in the same amounts as set forth for endogenous 3' expression regulation sequences. In such cases, it is to be understood that the recombinant polypeptide encoded by the transgene may comprise either genomic DNA or a double stranded DNA derived from cDNA. As with the 5' expression regulation sequences, the optimal amount of 3' expression regulation sequence may be readily determined by varying the amount of 3' flanking sequence to obtain maximal expression of the recombinant polypeptide. In general, the distal 3' regulation sequence, be it from an endogenous gene or a heterologous gene, will not extend into the adjacent gene from which it is derived and will exclude any sequences which adversely effect the level of transgene expression. In addition to the 5' and 3' expression regulation sequences and the recombinant DNA (either genomic or derived from cDNA) the transgenes of the invention preferably also comprise an intron sequence which interrupts the transcribed region of the transgene. Recombinant intervening sequences may, however, also comprise a "hybrid intervening sequence". Such hybrid intervening sequences comprise a 5' RNA splice signal and 3' RNA splice signal from intervening sequences from different sources.

Such hybrid intervening sequences containing permissive RNA splice signals are preferably used when the recombinant DNA corresponds to a cDNA sequence.

However, such hybrid intervening sequences are not limited to transgenes utilizing cDNA sequence. Rather, hybrid intervening sequences are also useful when the recombinant polypeptide is encoded by a genomic sequence. Based on the results obtained with the cDNA recombinant DNA and the general expectation that genomic DNA sequences express at higher levels than sequences derived from cDNA, it is expected that such hybrid intervening sequences used in conjunction with genomic recombinant DNA will further enhance expression levels above that which would otherwise be obtained with genomic sequence alone.

Based on the foregoing, it is apparent that preferred transgenes include large amounts of 5' and 3' expression regulation sequences. Further, the recombinant DNA is preferably derived from genomic clones which may be tens to hundreds of kilobases in length. Based on the present technology for cloning and manipulating DNA, the construction and microinjection of transgenes is practically limited to linearized DNA having a length not greater than about 50 kb. However, the transgenes of the invention, especially those having a length greater than about 50 kb, may be readily generated by introducing two or more overlapping fragments of the desired transgene into an embryonal target cell. When so introduced, the overlapping fragments undergo homologous recombination which results in integration of the fully reconstituted transgene in the genome of the target cell. In general, it is preferred that such overlapping transgene fragments have 100% homology in those regions which overlap. However, lower sequence homology may be tolerated provided efficient homologous recombination occurs. If non-homology does exist between the homologous sequence portions, it is preferred that the non-homology not be spread throughout the homologous sequence portion but rather be located in discrete areas. Although as few as 14 base pairs at 100% homology are sufficient for homologous recombination in mammalian cells (Rubnitz, J. and Subramani, S. (1984) *Mol. Cell. Biol.* 4, 2253–2258), longer homologous sequence portions are preferred, e.g. 500 bp, more preferably 1000 bp, next most preferably 2000 bp and most preferably greater than 2000 bp for each homologous sequence portion.

When the ultimate object is to secrete a recombinant polypeptide, a "secretory DNA sequence" encoding a functional secretion signal peptide is also operably linked within the transgene to direct secretion of the recombinant polypeptide from one or more cell types within the transgenic animal. Secretory DNA sequences in general are derived from genes encoding secreted proteins of the same species of the transgenic animal.

When the transgene of the invention encodes a recombinant polypeptide that is encoded by recombinant DNA derived from or corresponding to genomic DNA (or comprised substantially of such genomic sequences, e.g. greater than about 50%, more preferably greater than about 75%, most preferably greater than 90% of the codons encoding the recombinant polypeptide are from genomic sequences), the molar concentrations and protein levels in bovine transgenic milk are the same as for cDNA or higher. In general, the molar concentration of the recombinant polypeptide in such transgenic milk is preferably greater than about 50 μM, more preferably greater than about 150 μM, most preferably greater than about 500 μM. When viewed from the level of protein in the transgenic milk, the levels are preferably greater than about 1 mg/ml, more preferably greater than about 2.5 mg/ml, most preferably greater than 5 mg/ml.

The foregoing molar concentration and protein levels in bovine transgenic milk will vary depending upon the molecular weight of the particular recombinant polypeptide. A particular advantage of producing a recombinant polypeptide in bovine transgenic milk is that relatively large molecular weight polypeptides may be so produced which are otherwise difficult to produce in large quantities in other systems such as prokaryotic expression systems.

The mouse, however, normally produces between 55 to 80 milligrams of protein per ml of milk. A cow, on the other hand, normally produces between 30 to 34 milligrams of protein per ml. Since exceptionally high levels of recombinant polypeptide production may adversely affect the production of endogenous milk protein and/or have adverse effects upon the mammary secretory gland, it is preferred that the recombinant polypeptide concentration be between about 3 and 50% of the normal bovine milk protein concentration (i.e., between about 1 and 17 milligrams of recombinant polypeptide per ml of transgenic milk), more preferably between 10 to 20% (i.e., between 3 to about 7 milligrams per ml) and most preferably between 10 and 15% (i.e., between about 3 and 5 milligrams per ml) of the normal amount of protein produced in bovine milk. Such preferred ranges also provide a preferred maximum limit to the aforementioned levels of protein produced in transgenic bovine milk.

The term "effective subsequence" of the gene is to be understood in the same manner as defined above in connection with the DNA sequence.

The hybridization may be carried out as described in the "Definition" part of the Examples below, preferably on the basis of a probe comprising the coding part of the cDNA sequence shown SEQ ID NO: 1. The terms "homologous" and "effective subsequences" are used in a similar manner as that defined above.

Preferably, the polypeptide encoded by the analogue of the DNA sequence is at least 90% homologous, such as at least 95% or even 98% homologous with the amino acid sequence shown in SEQ ID NO: 2.

The β-casein gene has been isolated and sequenced using the procedure described in Example 1C below. In Example 1B, different genetic variants of the human β-casein gene are discussed.

An example of a specific analogue of the DNA sequence of the invention is a DNA sequence which comprises the DNA sequence shown in SEQ ID NO: 1 and particularly adapted for expression in *E. coli*. This DNA sequence is one which, when inserted in *E. coli* together with suitable regulatory sequences, results in the expression of a polypeptide having the amino acid sequence shown in SEQ ID NO: 2. Thus, this DNA sequence comprises specific codons recognized by *E. coli*. The preparation of this DNA sequence is described in Example 2.

As mentioned above, the DNA sequence shown in SEQ ID NO: 1 encodes a polypeptide comprising the functional domain/domains of human β-casein as well as the signal peptide naturally associated therewith. While the presence of a signal peptide in most cases is a prerequisite for allowing the polypeptide expressed from the DNA sequence to be transported out of the cell in which it is produced, the nature and origin of the particular signal peptide to be used may vary and need not be the signal peptide naturally associated with the human β-casein.

In accordance herewith, a particularly interesting DNA sequence of the invention is a DNA sequence which encodes a polypeptide comprising amino acids 1–210 shown in FIG. 1—corresponding to amino acids 1–210 in SEQ ID NO: 2 and amino acids 16–235 in SEQ ID NO.: 3—i.e. the amino acids corresponding to the mature human β-casein.

Human β-casein is highly phosphorylated at serine and threonine residues close to the N-terminal end, and this phosphorylated part of β-casein is believed to give the molecule its capacity to bind calcium and thus to participate in micelle formation. Thus, the N-terminal part of the molecule is highly important in terms of the biological activity of β-casein. In accordance herewith, an important subsequence of the DNA sequence of the invention is a DNA sequence which at least encodes the first part of the amino acid sequence shown in FIG. 1, especially the part comprising amino acids 1–12. However, also other parts of the molecule may be important in connection with the calcium-binding activity of human β-casein.

Further interesting subsequences of the nucleotide and deduced amino acid sequences shown in FIG. 1 are discussed in the following. A nucleotide sequence encoding a heptapeptide (VPYPQRA) (SEQ ID NO: 5) expected to have ACE-inhibitory activity is found at amino acid residues 167–173 of the amino acid sequence shown in FIG. 1. The expected ACE-inhibitory activity is based on the fact that a similar β-casein peptide having such activity and comprising 6 of the above listed 7 amino acid residues has been found to have ACE-inhibitory activity (Maruyama et al.). In this connection, also the pentapeptide corresponding to positions 168–172 of the amino acid sequence shown in FIG. 1 is contemplated to have ACE-inhibitory activity, which pentapeptide in nature is contemplated to be a cleavage product of the heptapeptide above. Also a peptide constituted by a part of the amino acids 39–52 of the sequence shown in FIG. 1, preferably a heptapeptide, a hexapeptide or a heptapeptide, is contemplated to have ACE-inhibitory activity. This expectation is based on the result of an analysis of the ACE-inhibitory activity of synthetic peptides having a similar amino acid sequence as peptides found in the above cited region of human β-casein (Kohmura et al.).

Peptides having opioid activity and immune stimulatory activity may be determined on the basis of the disclosure of Brantl.

In a further aspect, the present invention relates to a modified DNA sequence which differs from a DNA sequence of the invention as defined above in that at least one nucleotide has been deleted, substituted or modified or at least one additional nucleotide has been inserted so as to result in a DNA sequence which encodes a polypeptide having a calcium-binding activity which is similar to, increased or decreased as compared to the calcium-binding activity of human β-casein. Other interesting modifications result in peptides having a opioid activity or ACE-inhibitory activity.

The polypeptide encoded by the modified DNA sequence normally has an amino acid sequence which is different from the amino acid sequence of the human β-casein. It will be understood that a modified DNA sequence of the invention will be of importance in the preparation of novel polypeptides having a modified activity as compared to human β-casein or digestive fragments thereof or other similarly important activities.

When "substitution" is performed, one or more nucleotides in the full nucleotide sequence are replaced with one or more different nucleotides; when "addition" is performed, one or more nucleotides are added at either end of the full nucleotide sequence; when "insertion" is performed one or more nucleotides within the full nucleotide sequence is inserted; and when "deletion" is performed one or more nucleotides are deleted from the full nucleotide sequence whether at either end of the sequence or at any suitable point within it.

A modified DNA sequence may be obtained by well-known methods, e.g., by use of site-directed mutagenesis as described in textbooks in the field.

An example of an important modified DNA sequence of the invention is a DNA sequence in which additional codons encoding serine or threonine residues have been inserted so as to result in a modified DNA sequence encoding a polypeptide having an increased number of residues to be phosphorylated. The additional residues may be inserted either by being added at either end or within a DNA sequence of the invention or by replacing one or more non-serine or non-threonine codons present in a DNA sequence of the invention. A polypeptide encoded by such a modified DNA sequence is contemplated to have a higher degree of phosphorylation and thus an increased calcium-binding activity as compared to native human β-casein. The polypeptide produced from such a modified DNA sequence may be used as a nutrition supplement for populations which need to increase their calcium uptake, e.g. premature infants, women and old people.

Similarly, when a reduced calcium uptake is of interest, a modified DNA sequence of the invention encoding a polypeptide which has a lower number of residues to be phosphorylated than the polypeptide, the amino acid sequence of which is shown in SEQ ID NO: 2, is of interest. Here, one strategy would be to remove one or more codons for serine or threonine residues or replace one or more of such codons by non-serine or non-threonine residues.

Another example of an interesting modified DNA sequence is a DNA sequence which encodes the amino acid sequence of a naturally occurring human β-casein analogue or variant having an amino acid sequence different from the one shown in SEQ ID NO: 2 such as the variant disclosed by Greenberg et al. discussed above or other genetic variants as discussed in Example 1B. For this purpose, site-directed mutagenesis would be carried out using specific oligonucleotide probes conferring an exchange/removal of the relevant amino acid residues.

Another important use of a DNA sequence of the invention as defined above is in the preparation of a fusion protein comprising on the one hand a polypeptide comprising the amino acid sequence shown in SEQ ID NO: 2 or an analogue or subsequence thereof as defined above and on the other hand a polypeptide of another origin, e.g. a polypeptide or peptide part of another milk protein, e.g. a human milk protein such as α-lactalbumin, or a non-human milk protein such as a bovine or ovine milk protein such as bovine β-casein. The fusion protein may be prepared by fusing a DNA sequence of the invention with a DNA sequence encoding the other part of the fusion protein and the proper regulatory sequences in a manner which allows the expression of the fusion protein to occur.

The DNA sequences of the invention explained herein may comprise natural as well as synthetic DNA sequences, the natural sequence typically being derived directly from cDNA or genomic DNA, normally of mammalian origin, e.g. as described below. A synthetic sequence may be prepared by conventional methods for synthetically preparing DNA molecules, e.g. using the principles of solid or liquid phase peptide synthesis. Of course, also the DNA sequence may be of mixed cDNA and genomic, mixed cDNA and synthetic and mixed genomic and synthetic origin.

The terms "sequence", "subsequence", "analogue" and "polypeptide" as used herein with respect to sequences, subsequences, analogues and polypeptides according to the invention should of course be understood as not comprising these phenomena in their natural environment, but rather, e.g., in isolated, purified, in vitro or recombinant form. When reference is made to a DNA sequence of the invention this should be understood to include "analogues", "subsequences" and "modified sequences" as defined above. Similarly, when reference is made to "a polypeptide of the invention" this should be understood to include any of the polypeptides defined in the following.

In another important aspect, the present invention relates to a polypeptide encoded by a DNA sequence of the invention as defined above. A particularly interesting polypeptide of the invention is a recombinant human β-casein polypeptide comprising the amino acid sequence shown SEQ ID NO: 2 or a subsequence thereof having the calcium-binding activity of human β-casein. An example of an important polypeptide comprising an important subsequence of said amino acid sequence is a polypeptide comprising amino acid residues 1–210 of the amino acid sequence shown in SEQ ID NO: 2 corresponding to the mature recombinant human β-casein without a signal peptide.

As it will be apparent from the above disclosure, another interesting polypeptide of the present invention is one which differs from a polypeptide comprising the amino acid sequence shown in FIG. 1 in that at least one amino acid residue has been substituted with a different amino acid residue and/or in that at least one amino acid residue has been deleted or added so as to result in a polypeptide comprising an amino acid sequence being different from the amino acid sequence shown in FIG. 1 and having a similar, increased or decreased calcium-binding activity as compared to the calcium-binding activity of human β-casein or having ACE-inhibitory activity or opioid activity. Examples of a strategy for designing and preparing modified polypeptides of the invention are apparent from the above disclosure.

The polypeptide of the present invention is one in which at least one amino acid residue has been modified by post-translational modification and is preferably in glycosylated and/or phosphorylated form. Normally, glycosylation is achieved when the polypeptide is expressed by a cell of a higher organism such as yeast or preferably a mammal, whereas phosphorylation is achieved also in the case of expression in lower organisms such as bacteria. The amino acid residues of the polypeptide of the invention which are normally phosphorylated are mentioned above. Glycosylation is normally found in connection with amino acid residues Asn, Ser, Thr or hydroxylysine.

In a further aspect, the present invention relates to a replicable expression vector which carries and is capable of mediating the expression of a DNA sequence encoding human β-casein.

In the present context, the term "replicable" means that the vector is able to replicate in a given type of host cell into which it has been introduced. Immediately upstream of the human β-casein DNA sequence there may be provided a sequence coding for a signal peptide, the presence of which ensures secretion of the human β-casein expressed by host cells harbouring the vector. The signal sequence may be the one naturally associated with the human β-casein DNA sequence or of another origin.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated. Examples of suitable vectors are a bacterial expression vector, e.g. as exemplified in Example 2, and a yeast expression vector, e.g. as exemplified in Example 3. The vector of the invention may carry any of the DNA sequences of the invention as defined above and be used for the expression of any of the polypeptides of the invention defined above. However, when a bacterial vector is concerned it is preferred that the DNA sequence encoding human β-casein comprises the sequence shown in SEQ ID NO: 3, i.e. the sequence specifically adapted to expression in bacterial cells.

The present invention further relates to a cell harbouring a replicable expression vector as defined above. In principle, this cell may be of any type of cell, i.e. a prokaryotic cell such as a bacterium, e.g. E. coli, a unicellular eukaryotic organism, a fungus or yeast, e.g. Saccharomyces cerevisiae or a cell derived from a multicellular organism, e.g. a mammal. The mammalian cells are especially suitable for the purpose and are further discussed below.

In another important aspect, the invention relates to a method of producing recombinant human β-casein, in which a DNA sequence encoding human β-casein is inserted in a vector which is able to replicate in a specific host cell, the resulting recombinant vector is introduced into a host cell which is grown in or on an appropriate culture medium under appropriate conditions for expression of human β-casein and the human β-casein is recovered. The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA, examples of which are given in Example 2 and 3 below. The recombinant human β-casein expressed by the cells may be secreted, i.e. exported through the cell membrane, dependent on the type of cell and the composition of the vector. Examples of bacterial and yeast expression systems providing intracellular and extracellular expression, respectively, are given in Examples 2 and 3. The method outlined above is equally useful for the production of any of the polypeptides of the invention as defined above, i.e. on the basis of a DNA sequence of the invention.

If the human β-casein is produced intracellularly by the recombinant host, that is, is not secreted by the cell, it may be recovered by standard procedures comprising cell disrupture by mechanical means, e.g. sonication or homogenization, or by enzymatic or chemical means followed by purification. Such methods are further described below and examples of the recovery procedure are given in Example 5. The present invention provides a generally novel purification method for purifying casein proteins including β-casein. This method is further discussed below.

In order to be secreted, the DNA sequence encoding human β-casein should be preceded by a sequence coding for a signal peptide, the presence of which ensures secretion of human β-casein from the cells so that at least a significant proportion of the human β-casein expressed is secreted into the culture medium and recovered.

Although recombinant production of human β-casein as disclosed above using lower organisms such as bacteria and yeast as production organisms for some purposes is satisfactory, e.g. when moderate yields of human β-casein are sufficient, when a short-term production is desirable or when human β-casein of a high purity substantially free from other mammalian derived substances such as proteins, in particular milk proteins, are desirable, the presently preferred method of producing recombinant human β-casein of the invention is by use of transgenic non-human meals capable of excreting the human β-casein into their milk. The use of transgenic nonhuman mammals has the advantage that large yields of recombinant human β-casein are obtainable at reasonable costs and, especially when the non-human mammal is a bovine species such as cows, that the recombinant human β-casein is produced in milk which is the normal constituent of, e.g., infant formulae so that no extensive purification is needed when the recombinant human β-casein is to be used as a nutrient supplement in milk-based products. Furthermore, production in a higher organism such as a non-human mammal normally leads to the correct processing of the mammalian protein, e.g. with respect to post-translational processing as discussed above and proper folding. Also large quantities of substantially pure human β-casein may be obtained.

Accordingly, in a further important aspect, the present invention relates to a mammalian expression system comprising a DNA sequence encoding human β-casein inserted into a gene encoding a milk protein of a non-human mammal so as to form a hybrid gene which is expressible in the mammary gland of an adult female of a mammal harbouring said hybrid gene.

The DNA sequence encoding human β-casein is preferably a DNA sequence as defined above encoding a polypeptide comprising the amino acid sequence shown in SEQ ID NO: 2 such as the DNA sequence shown in SEQ ID NO: 3 or an analogue or effective subsequence thereof.

The mammary gland as a tissue of expression and genes encoding milk proteins are generally considered to be particularly suitable for use in the production of heterologous proteins in transgenic non-human mammals as milk proteins are naturally produced at high expression levels in the mammary gland. Also, milk is readily collected and available in large quantities. In the present connection the use of milk protein genes in the production of recombinant human β-casein has the further advantage that it is produced under conditions similar to the its natural production conditions in terms of regulation of expression and production location (the mammary gland).

In the present context the term "hybrid gene" denotes a DNA sequence comprising on the one hand a DNA sequence encoding human β-casein as defined above and on the other hand a DNA sequence of a milk protein gene which is capable of mediating the expression of the hybrid gene product. The term "a milk protein gene" denotes an entire gene as well as an effective subsequence thereof capable of mediating and targeting the expression of the hybrid gene to the tissue of interest, i.e. the mammary gland. The milk protein gene may be the gene for β-lactoglobulin, α-lactalbumin or a casein, but the whey acid protein gene is particularly preferred.

Normally, the effective subsequence is one which at least harbours one or more of a promoter region, a transcriptional start site, 3' and 5' non-coding regions and structural sequences. The DNA sequence encoding human β-casein is preferably substantially free from prokaryotic sequences, such as vector sequences, which may be associated with the DNA sequence after, e.g., cloning thereof.

The hybrid gene is preferably formed by inserting in vitro the DNA sequence encoding human β-casein into the milk protein gene by use of techniques known in the art. Alternatively, the DNA sequence encoding human β-casein can be inserted in vivo by homologous recombination.

Normally, the DNA sequence encoding human β-casein will be inserted in one of the first exons of the milk protein gene of choice or an effective subsequence thereof comprising the first exons and preferably a substantial part of the 5' flanking sequence which is believed to be of regulatory importance.

The hybrid gene preferably comprises a sequence encoding a signal peptide so as to enable the hybrid gene product to be secreted correctly into the mammary gland. The signal peptide will typically be the one normally found in the milk protein gene in question or one associated with the DNA sequence encoding human β-casein. However, also other signal sequences capable of mediating the secretion of the hybrid gene product to the mammary gland are relevant. Of course, the various elements of the hybrid gene should be fused in such a manner as to allow for correct expression and processing of the gene product. Thus, normally the DNA sequence encoding the signal peptide of choice should be precisely fused to the N-terminal part of the DNA sequence encoding human β-casein. In the hybrid gene, the DNA sequence encoding human β-casein will normally comprise its stop codon, but not its own message cleavance and polyadenylation site. Downstream of the DNA sequence encoding human β-casein, the mRNA processing sequences of the milk protein gene will normally be retained.

A number of factors are contemplated to be responsible for the actual expression level of a particular hybrid gene. The capability of the promoter as well of other regulatory sequences as mentioned above, the integration site of the expression system in the genome of the mammal, the integration site of the DNA sequence encoding human β-casein in the milk protein encoding gene, elements conferring post-transcriptional regulation and other similar factors may be of vital importance for the expression level obtained. On the basis of the knowledge of the various factors influencing the expression level of the hybrid gene, the person skilled in the art would know how to design an expression system useful for the present purpose.

A variety of different milk proteins are secreted by the mammary gland. Two main groups of milk proteins exist, namely the caseins and the whey proteins. The composition of milk from different species varies qualitatively as well as quantitatively with respect to these proteins. Most non-human mammals produces 3 different types of casein, namely α-casein, β-casein and κ-casein. The most common bovine whey proteins are α-lactalbumin and β-lactalbumin. The composition of milk of various origins are further disclosed in Clark et al., 1987.

The milk protein gene to be used may be derived from the same species as the one in which the expression system is to be inserted, or it may be derived from another species. In this connection it has been shown that the regulatory elements that target gene expression to the mammary gland are functional across species boundaries (which may be due to a possible common ancestor) (Hennighausen et al.).

Examples of suitable genes encoding a milk protein or effective subsequences thereof to be used in the construction of an expression system of the invention are normally found among whey proteins of various mammalian origins, e.g. a whey acidic protein (WAP) gene, preferably of murine origin, and a β-lactoglobulin gene, preferably of ovine origin. Also casein genes of various origins may be found to be suitable for the transgenic production of human β-casein, e.g. bovine αS1-casein and rabbit β-casein. The presently preferred gene is a murine WAP gene as this has been found to be capable of providing a high level expression of a number of foreign human proteins in milk of different transgenic animals (Hennighausen et al.).

Another sequence preferably associated with the expression system of the invention is a so-called expression stabilizing sequence capable of mediating high-level expression. Strong indications exist that such stabilizing sequences are found in the vicinity of and upstream of milk protein genes.

The DNA sequence encoding a human β-casein to be inserted in the expression system of the invention may be of cDNA, genomic or synthetic origin or any combination thereof. While some expression systems have been found to function best when cDNA encoding a desirable protein is used, others have been found to require the presence of introns and other regulatory regions in order to obtain a satisfactory expression (Hennighausen et al.). In some cases it may be advantageous to introduce genomic structures as polypeptide encoding element in vector constructs compared to cDNA elements (Brinster et al.).

Brinster et al. (*PNAS* 85, 836–840 (1988)) have demonstrated that introns increase the transcriptional efficiency of transgenes in transgenic mice. Brinster et al. show that all the exons and introns of a natural gene are important both for efficient and for reliable expression (that is to say, both the levels of the expression and the proportion of expressing animals) and is due to the presence of the natural introns in that gene. It is known that in some cases this is not attributable to the presence of tissue-specific regulatory sequences in introns, because the phenomenon is observed when the expression of a gene is redirected by a heterologous promoter to a tissue in which it is not normally expressed. Brinster et al. say that the effect is particular to transgenic animals and is not seen in cell lines.

The intron and exon structure may result in higher steady state mRNA levels than obtained when cDNA based vectors are used. When the expression system is based on the WAP gene, a cDNA sequence is preferred as it has been verified by various experiments that the WAP gene is capable of providing as good an expression of cDNA as of genomic DNA, or even a better expression (Hennighausen et al.). In Example 4, an expression system based on the murine WAP gene and a cDNA sequence of the invention encoding human β-casein is illustrated and further discussed.

In the specification, the term "intron" includes the whole of any natural intron or part thereof.

A hybrid gene and its constituents have been discussed in detail above. The hybrid gene constitutes an important intermediate in the construction of an expression system of the invention as disclosed above.

In a further aspect, the present invention relates to a hybrid gene comprising a DNA sequence encoding human β-casein inserted into a gene encoding a milk protein of a non-human mammal, the DNA sequence being inserted in the milk protein gene in such a manner that it is expressible in the mammary gland of an adult female of a mammal harbouring the hybrid gene. The hybrid gene and its constituents have been discussed in detail above. The hybrid gene constitutes an important intermediate in the construction of an expression system of the invention as disclosed above.

In a further important aspect, the present invention relates to a method of producing a transgenic non-human mammal capable of expressing human β-casein, comprising injecting an expression system of the invention as defined above into a fertilized egg or a cell of an embryo of a mammal so as to incorporate the expression system into the germline of the mammal and developing the resulting injected fertilized egg or embryo into an adult female mammal.

In another aspect, the present invention relates to a non-human mammalian cell harbouring an expression system as defined above. The mammalian cell is preferably an embryo cell or a pro-nucleus. The expression system is suitably inserted in the mammalian cell using a method as explained in the following and specifically illustrated in Examples 4 and 6–9 below.

In a further important aspect, the present invention relates to a method of producing a transgenic non-human mammal capable of expressing a polypeptide having the amino acid sequence SEQ ID NO:2 or an analogue or variant thereof which has either the calcium binding activity of human β-casein, or opioid activity, or angiotensin converting enzyme (ACE) inhibitory activity, or a combination of any two or three of these activities, said method comprising chromosomally incorporating a DNA sequence encoding the polypeptide into the genome of a non-human mammal.

The "non-human mammals" of the invention comprise all non-human mammals capable of producing a "transgenic non-human mammal" having a "desirable phenotype". Such mammals include non-human primates, murine species, bovine species, canine species, etc. Preferred non-human animals include bovine, porcine and ovine species, most preferably bovine species.

Desirable phenotypes for transgenic non-human mammals include, but are not limited to, the production of recombinant polypeptides in the milk of female transgenic non-human meals.

The transgenic non-human meals of the invention are produced by introducing a "transgene" into an embryonal target cell of the animal of choice. In one aspect of the invention, a transgene is a DNA sequence which is capable of producing a desirable phenotype when contained in the genome of cells of a transgenic non-human meal. In specific embodiments, the transgene comprises a "recombinant DNA sequence" encoding a "recombinant polypeptide" In such cases, the transgene is capable of being expressed to produce the recombinant polypeptide.

The incorporation of the expression system into the germline of the mammal may be performed using any suitable technique, e.g. as described in Hogan B., Constantini, F. and Lacy, E. Manipulating the Mouse Embryo. A Laboratory Manual. Cold Spring Harbor Laboratory Press, 1986 or in WO91/08216.

Methods of introducing transgenes or overlapping transgene fragments into embryonal target cells include microinjection of the transgene into the pronuclei of fertilized oocytes or nuclei of ES cells of the non-human animal. Such methods for murine species are well known to those skilled in the art. Alternatively, the transgene may be introduced into an animal by infection of zygotes with a retrovirus containing the transgene (Jaenisch, R. (1976), *Proc. Natl. Acad. Sci. USA,* 73, 1260–1264). The preferred method is microinjection of the fertilized oocyte. In this preferred embodiment, the fertilized oocytes are first microinjected by standard techniques. They are thereafter cultured in vitro until a "pre-implantation embryo" is obtained. Such pre-implantation embryos preferably contain approximately 16 to 150 cells. The 16 to 32 cell stage of an embryo is commonly referred to as a morula. Those pre-implantation embryos containing more than 32 cells are commonly referred to as blastocysts. They are generally characterized as demonstrating the development of a blastocoel cavity typically at the 64 cell stage. Methods for culturing fertilized oocytes to the pre-implantation stage include those described by Gordon et al. (1984), *Methods in Enzymology,* 101, 414; Hogan et al. (1986) in *Manipulating the Mouse Embryo,* Cold Spring Harbor Laboratory Press, Cold Spring Harbor, N.Y. (for the mouse embryo); and Hammer et al. (1985), *Nature,* 315, 680 (for rabbit and porcine embryos); Gandolfi et al. (1987) *J. Reprod. Fert.* 81, 23–28; Rexroad et al. (1988) *J. Anim. Sci* 66, 947–953 (for ovine embryos); and Eyestone, W. H. et al. (1989) *J. Reprod. Fert.* 85, 715–720; Camous et al. (1984) *J. Reprod. Fert.* 72, 779–785; and Heyman, Y. et al. (1987) *Theriogenology* 27, 5968 (for bovine embryos). Such pre-implantation embryos are thereafter transferred to an appropriate female by standard methods to permit the birth of a transgenic or chimeric animal depending upon the stage of development when the transgene is introduced. As is well known, mosaic animals can be bred to form true germline transgenic animals.

Since the frequency of transgene incorporation is often low, the detection of transgene integration in the pre-implantation embryo is highly desirable. In one aspect of the invention, methods are provided for identifying embryos wherein transgenesis has occurred and which permit implantation of transgenic embryos to form transgenic animals. In this method, one or more cells are removed from the pre-implantation embryo. When equal division is used, the embryo is preferably not cultivated past the morula stage (32 cells). Division of the pre-implantation embryo (reviewed by Williams et al. (1986) *Theriogenology* 22, 521–531) results in two "hemi-embryos" (hemi-morula or hemi-blastocyst) one of which is capable of subsequent development after implantation into the appropriate female to develop in utero to term. Although equal division of the pre-implantation embryo is preferred, it is to be understood that such an embryo may be unequally divided either intentionally or unintentionally into two hemi-embryos which are not necessarily of equal cell number. Essentially, all that is required is that one of the embryos which is not analyzed as hereinafter described be of sufficient cell number to develop to full term in utero. In a specific embodiment, the hemi-embryo which is not analyzed as described herein, if shown to be transgenic, is used to generate a clonal population of transgenic non-human animals.

One of each of the hemi-embryos formed by division of preimplantation embryos is analyzed to determine if the transgene has been integrated into the genome of the organism. Each of the other hemi-embryos is maintained for subsequent implantation into a recipient female of the species.

The identification of the pre-implantation embryos containing the integrated transgene is achieved by analyzing the DNA from one of each of the hemi-embryos. Such DNA is typically obtained by lysing the hemi-embryo and analyzing the thus released DNA as described in Example 8. A polymerase chain reaction is performed to amplify all or part of the transgene. When the entire transgene is amplified, two extension primers each complementary to opposite strands at opposing ends of the transgene are used for amplification. Generally, the amplified DNA from the hemi-embryo is subjected to electrophoresis followed by hybridization with labeled probe complementary to the region of the transgene between the two extension primers. This facilitates the determination of the size of the amplified DNA sequences, if any, and provides an indication of whether the transgene has been integrated into the pre-implantation embryo from which the hemi-embryo was obtained (now called a "transgenic hemi-embryo"). If it has, the remaining untreated transgenic hemi-embryo is transplanted into a recipient parent. After in utero development, the transgenic non-human animal having the desired phenotype conferred by the integrated transgene is identified by an appropriate method in utero or after birth.

The above described methods for the detection of transgenesis in pre-implantation embryos provide economical and time saving methods for generating transgenic non-human animals since they significantly decrease the number of pregnancies required to produce a transgenic animal and substantially increase the likelihood that an implanted embryo will produce a transgenic non-human animal. Such methods are especially important for those animals for which very low or non-existent frequencies of transgenesis have been obtained, e.g. bovine species.

In an alternate embodiment, the above described method for detecting transgenesis in pre-implantation embryos is combined with embryonic cloning steps to generate a clonal population of transgenic embryos which may thereafter be implanted into recipient females to produce a clonal population of transgenic non-human animals also having the same genotype. In this regard, it is to be understood that transgenic embryos and/or non-human transgenic animals having the same "genotype" means that the genomic DNA is substantially identical between the individuals of the embryo and/or transgenic animal population. It is to be understood, however, that during mitosis various somatic mutations may occur which may produce variations in the genotype of one or more cells and/or animals. Thus, a population having the same genotype may demonstrate individual or subpopulation variations.

After a hemi-embryo is identified as a transgenic hemi-embryo, it is cloned. Such embryo cloning may be performed by several different approaches. In one cloning method, the transgenic hemi-embryo is cultured in the same or in a similar medium as used to culture individual oocytes to the preimplantation stage. The "transgenic embryo" so formed (preferably a transgenic morula) is then divided into "transgenic hemi-embryos" which can then be implanted into a recipient female to form a clonal population of two transgenic non-human animals. Alternatively, the two transgenic hemi-embryos obtained may be again cultivated to the pre-implantation stage, divided, and recultivated to the transgenic embryo stage. This procedure is repeated until the desired number of clonal transgenic embryos having the same genotype are obtained. Such transgenic embryos may then be implanted into recipient females to produce a clonal population of transgenic non-human animals.

In a preferred cloning method, the transgenic embryo is cloned by nuclear transfer according to the techniques of Prather et al. (1988) *Biol. Reprod.* 37, 59–86; Roble et al. (1987) *J. Anim. Sci.* 64, 642–664. According to this method, nuclei of the transgenic embryo are transplanted into enucleated oocytes, each of which is thereafter cultured to the blastocyst stage. At this point, the transgenic embryos may be resubjected to another round of cloning by nuclear transplantation or may be transferred to a recipient parent for production of transgenic offspring having the same genotype.

In addition to the foregoing methods for detecting early transgenesis, other methods may be used to detect transgenesis. Such method include in utero and post partum analysis of tissue. In utero analysis is performed by several techniques. In one, transvaginal puncture of the amniotic cavity is performed under echoscopic guidance (Bowgso et al. (1975) *Bet. Res.* 96, 124–127; Rumsey et al. (1974) *J. Anim. Sci.* 39, 386–391). This involves recovering about 15 to 20 milliliters of amniotic fluid between about day 35 and day 100 of gestation. This volume of amniotic fluid contains about 1000 to 12,000 cells per ml originating from the urogenital tract, the skin and possibly the lungs of the developing embryo. Most of these cells are dead. Such cells, however, contain genomic DNA which is subjected to PCR analysis for the transgene as an indication of a successful transgenesis. Alternatively, fetal cells may be recovered by chorion puncture. This method may also be performed transvaginally and under echoscopic guidance. In this method, a needle is used to puncture the recipient animal's placenta, particularly the placentonal structures, which are fixed against the vaginal wall. Such sampling may be performed around day 60 of gestation in bovine species. Chorion cells, if necessary, are separated from maternal tissue and subjected to PCR analysis for the transgene as an indication of successful transgenesis.

Transgenesis may also be detected after birth. In such cases, transgene integration can be detected by taking an appropriate tissue biopsy such as from the ear or tail of the putative transgenic animal. About one to two centimeters of tail or about five to ten square millimeters of ear are obtained followed by southern blotting with a probe for the transgene according to the method of Hogan et al. (1986) *Manipulating the Mouse Embryo*, Cold Spring Harbor Laboratory.

Normally, not all of the injected eggs will develop into transgenic mammals capable of expressing human β-casein. Transgenic founder animals can be identified e.g. as described in Example 4. About half of the mammals will from a statistically point of view be males. One the basis of the identified transgenic individuals—male and female—progeny can be established and stable lines of transgenic animals established.

Once integrated in the germ line, the DNA sequence encoding human β-casein may be expressed at high levels to produce a correctly processed and functional human β-casein. Transgenic females from which recombinant polypeptide can be harvested can thus be bred in the following generations.

The mammalian β-casein expressing capability can be destroyed by introduction of mutations in the DNA sequence responsible for the expression of the β-casein. Such mutations may comprise mutations which make the DNA sequence out of frame, or introduction of a stop codon or a deletion of one or more nucleotides of the DNA sequence.

The mammalian β-casein gene or a part thereof may be replaced with an expression system as defined above or a DNA sequence encoding human β-casein by use of the well known principles of homologous recombination.

Gene targeting refers to the directed modification of a selected chromosomal locus of an endogenous chromosome of a cell by homologous recombination with an exogenous DNA sequence having homology to the selected endogenous sequence. Gene targeting has been employed to enhance, modify and disrupt expression of endogenous genes (see Bollag et al. (1989) *Ann. Rev. Genet.* 23, 199–225).

Of further interest is a method of producing a transgenic non-human mammal capable of expressing human β-casein and substantially incapable of expressing β-casein from the mammal itself, comprising 1) destroying the mammalian β-casein expressing capability of the mammal so that substantially no mammalian β-casein is expressed and inserting an expression system of the invention as defined above or a DNA sequence encoding human β-casein into the germline of the mammal in such a manner that human β-casein is expressed in the mammal and/or 2) replacing the mammalian β-casein gene or part thereof with an expression system of the invention as defined above or a DNA sequence encoding human β-casein.

The mammalian β-casein expressing capability is conveniently destroyed by introduction of mutations in the DNA sequence responsible for the expression of the β-casein. Such mutations may comprise mutations which make the DNA sequence out of frame, or introduction of a stop codon or a deletion of one or more nucleotides of the DNA sequence.

The mammalian β-casein gene or a part thereof may be replaced with an expression system as defined above or a DNA sequence encoding human β-casein by use of the well known principles of homologous recombination.

In a further aspect, the present invention relates to a transgenic non-human mammal prepared by a method as described above.

The DNA used to make transgenic cells and animals preferably comprises genomic DNA rather than cDNA. This is because the expression of transgenes is preferably limited to tissue-specific expression as well as temporal-specific expression. When the transgene is derived from genomic DNA, important cis-acting regulatory sequences such as enhancers and other regulatory elements, located either in introns or in regions distant from the structural gene, can be included. Such regulatory sequences are lost during transcription and RNA processing and accordingly are not generally available with cDNA-derived transgenes.

While the transgenic non-human mammal of the invention in its broadest aspect is not restricted to any particular type of mammal, the mammal will normally be selected from the group consisting of mice, rats, rabbits, sheep, pigs, goats and cattle. For large scale production of human β-casein the larger animals such as sheep, goats, pigs and especially cattle are normally preferred due to their high milk production. However, also mice, rabbits and rats may be interesting due to the fact that the manipulation of these animals is more simple and results in transgenic animals more quickly than when, e.g. cattle, are concerned.

Also progeny of a transgenic mammal as defined above, capable of producing human β-casein is within the scope of the present invention.

In a still further aspect, the present invention relates to a method of preparing human β-casein comprising collecting milk from a transgenic non-human mammal of the invention as defined above and recovering the human β-casein from the milk. The milk may be collected in any suitable manner normally used in connection with the collection of milk from the mammal in question.

From the above explanation it will be clear that the present invention for the first time makes it possible to produce milk from a non-human mammal comprising human β-casein, the importance and utility of which will be apparent from the present context. Thus, a further aspect of the present invention includes milk from a non-human mammal comprising recombinant human β-casein. Of particular interest is milk from a non-human mammal comprising a polypeptide of the invention as defined above comprising the amino acid sequence shown in SEQ ID NO: 2 or a polypeptide encoded by a DNA sequence as defined in SEQ ID NO: 3 or an analogue or subsequence thereof as defined above. Typically, the milk of the invention will be obtained from a transgenic mammal of the invention as defined above.

From the above explanation it will be apparent that an important use of the polypeptide of the invention is as a nutrient supplement, in particular as a substituent of an infant formula.

In a still further aspect, the present invention relates to an infant formula comprising recombinant human β-casein, in particular a polypeptide of the invention as defined above. The infant formula may be prepared by adding the recombinant human β-casein or polypeptide in a purified or partly purified form to the normal constituents of the infant formula. However, normally it is preferred that the infant formula is prepared from milk of the invention as defined above, especially when it is of bovine origin. The infant formula may be prepared using conventional procedures and contain any necessary additives such as minerals, vitamins etc.

Preparation of infant formula

Once the genetically engineered human α-lactalbumin and β-casein have been separated and purified, they are combined in a human infant formula. The formulation of infant formula based on bovine α-lactalbumin and casein has been defined (V. S. Packard, "Human Milk and Infant Formula", pp. 147–154. Academic Press (1982)). It is suggested that the whey proteins and caseins be in a ratio of 60:40 or 0.9 weight percent α-lactalbumin to 0.6 weight percent casein for a total of 1.5 g protein/100 ml of milk. However, computer optimization of this ratio for the human proteins, to obtain amounts of each amino acid corresponding to the amounts actually found in human milk requires a ratio of 40:50 or 0.67 weight percent α-lactalbumin to 0.83 weight percent β-casein (a total of 1.5 g protein/100 ml of milk) to reach known levels of all the essential amino acids. Supplementary amino acids, such as L-methionine used in soy-based formulas, are not needed.

Calcium is preferably of a chemical form that is biologically compatible and commercially available, such as from SIGMA Chemical Co., and should preferably be present to a minimum of 50 mg/100 kcal. Minimum phosphorus level is 25 mg/100 kcal. Minimum and maximum amounts of sodium, potassium, and chloride must also be observed. These levels are met within the ranges 6–17, 14–34, and 11–29 milliequivalents (mEq), respectively, in a formula providing 670 kcal/liter. One milliequivalent is equal to the atomic weight (in milligrams) of the element divided by valence. Osmolarity—in moles of solute/liter should not exceed 400 mOsm.

Caloric density of infant formulas of 670 kcal/liter appears nearly optimal for normal full-term infants. The formulation should provide a calcium-phosphorus ratio preferably of not less than 1.1:1.0 nor more than 2:1. Most preferably, the ratio is near 1.5:1, at least through most of the first year of life. By one year of age, the appropriate ratio is more nearly 1:1.

Infant formulas can vary in composition, but within fairly narrow and quite precise limits. In general, as a complete substitute for human milk, formula is preferably comprised of protein at 7–16% of calories, with a preferable ratio of α-lactalbumin to β-casein ranging from about 70:30 to about 30:70, fat at 30–54% of calories, linoleic acid at 2–3% of calories, and the remaining calories from carbohydrate sources. The fat component of the formula is preferably comprised of various vegetable fats. Because many contaminants or pollutants of food are soluble in fat, specially refined vegetable fats and oils provide better control of formula contents. To prevent conversion of cis to trans fatty acids, and loss thereby of essential fatty acids, low- (or ultrahigh) temperature treatment is preferably used throughout processing.

A representative list of ingredients follows:

Water

Lactose (corn syrup or sucrose could be used)

Human α-lactalbumin

Human β-casein

Coconut oil

Soybean oil

Modified corn starch

Mono- and diglycerides

Soy lecithin

Carrageenan

Vitamin sources

Vitamin A palmitate

Vitamin D3

α-tocopheryl acetate (vitamin E)

Phytonadione (vitamin K)

Ascorbic acid (vitamin C)

Thiamine chloride hydrochloride (vitamin B1)

Riboflavin

Cyanocobalamin (vitamin B12)

Niacinamide

Calcium pantothenate

Pyridoxine hydrochloride (vitamin B6)

Biotin

Folic acid

Choline chloride

Mineral sources

Calcium phosphate, tribasic

Cupric sulfate

Ferrous sulfate

Magnesium chloride

Potassium chloride

Potassium citrate

Potassium iodide

Zinc sulfate

The amounts of each of the ingredients listed are adjusted to keep each nutritional component within the maximum and minimum guidelines recommended by the FDA (V. S. Packard, "Human Milk and Infant Formula", pp. 147–154. Academic Press (1982)) and by the American Academy of Pediatrics (Am. Acad. of Pediatrics Comm. on Nutrition, *Pediatrics* 72, 359–363 (1983)), as disclosed below (modified from American Academy of Pediatrics, Committee on Nutrition: Commentary on Breast-Feeding and Infant Formulas, including proposed standards for formulas. *Pediatrics* 57, 278 (1976)).

Carbohydrate sources include lactose (or milk and whey products that contain lactose), sucrose, corn syrup solids (a source of glucose), and starch.

Appropriate thickening agents, emulsifiers, antioxidants, and compounds for adjusting pH may be used. In the United States, conditions of use of additives in infant formula are regulated under the *Code of Federal Regulations* (CFR), Title 21, Section 172,620 and Section 180.

Vitamin additives for use in infant formulas are approved by the Food and Agricultural Organization (FAO). Processing requirements, availability, and/or stability in the specific food system will dictate which form(s) will serve best.

The FAO also approves mineral sources for infant formula. Suitability of any given mineral additive depends on composition and moisture level of the food product. Furthermore, each food imposes its own requirements for flavour and/or textural stability. Oxidative rancidity is an ever-present problem in iron and/or copper-fortified foods containing unsaturated fats. Gelation is a potential problem in concentrated liquid infant formulas. Reduced iron or electrolytic iron, which serve well in dry foods, will settle out as a sediment in liquid formula. FAO also recognizes the need for acids and bases for making pH adjustments; however, these must be accounted for in determining total content of any given mineral.

Certain mineral compounds, for instance calcium and phosphorus, are required in fairly large amounts in infant formula. Other mineral elements are required only in trace amounts. Thus, trace minerals in ingredients of infant formula must be considered, along with those that may be added in water supplies used to reconstitute various dry ingredients. Water supplies may or may not be treated for this purpose, depending upon the overall quality. Water quality should be monitored, however, along with the trace mineral content of finished formula.

When trace minerals are added to formula, sulfate salts are commonly used. Acceptable levels of sulfate ions, however, have not been specified (Anderson et al. (1980)). Because of the potential to cause methemoglobinemia, nitrate salts are usually not added to formula. A trace amount may occur in formula made up of vegetable products. Nitrates also occur and are occasionally found at high levels in some water supplies. Copper is another potentially toxic component of water. However, any biologically acceptable salt composition is contemplated for use in the present invention.

Minerals commonly added to formulas include calcium, phosphorus, magnesium, iron, copper, iodine, zinc, potassium, sodium, manganese, and chlorine (as chloride). Conventional infant formula compositions require the addition of bovine or soy protein sources which may have a significant amount of minerals carried along with the protein component. The presence of these minerals decreases the accuracy of determining the mineral components of the manufactured infant formula. Conventional methodologies, including electrodialysis, ion exchange and ultrafiltration, are commonly used to separate the proteins from the minerals and other contaminants associated with them. Use of the recombinant DNA-derived human proteins of the present invention in human infant formula reduces the amount of protein purification necessary, thus providing a more accurate determination of mineral content and reduced expenditures for protein processing.

Formulations for premature infants

For preterm or low-weight infants (under 2500 g), formulas are usually modified, with the evaluation of protein and mineral levels. Lactose level may preferably be lowered by one-third to one-half regular amounts, with the difference made up with more readily absorbable carbohydrate source such as corn syrup solids. Fat, calcium, and phosphorus must be available in readily utilizable form.

Caloric density is preferably raised to 800–1000 kcal/liter; with approximately 11% of the calories from protein and 50% from fat. In general, corn and soy oil appear reasonably well absorbed by premature infants.

In addition to infant formulas, other food formulations may also be supplemented with recombinant polypeptides from transgenic bovine milk. For example, such recombinant polypeptides may be used to supplement common diet formulations.

Thus, the production of human β-casein in the milk of transgenic bovine species provides a source of human β-casein. Such human β-casein may be purified from the transgenic milk for formulation purposes. Alternatively, the whole transgenic milk may be used, preferably after pasteurization, in either liquid or dried form.

In a further aspect, the present invention relates to a generally novel method of isolating and/or purifying casein proteins from a mixture of components including proteins different from casein. The method comprises adding to the mixture of components from which the casein is to be isolated and/or purified ammonium sulphate in a concentration equal to or of above 0.05M to precipitate the casein proteins, separating the precipitated β-casein protein from the mixture of components, and optionally removing salt from the precipitated casein.

The purification method of the invention is based on the fact that proteins show a decreased solubility in the presence of salts. This effect is known as "salting out".

The method is believed to be generally applicable for the isolation of any kind of casein proteins from any kind of mixture, including a mixture in which the casein proteins are naturally present, e.g. milk, and a mixture in which the casein proteins have been artificially added or synthesized, e.g. from a mixture of cells or cell components in which recombinant casein has been produced. The cells may be microorganism cells, such as bacterial or yeast cells, or mammalian cells.

Conventionally, casein in milk has been separated by acid precipitation at its isoelectrical point, e.g. as described by Rowland, 1938. However, acid precipitation has certain disadvantages including the need of pH-control, which disadvantages are especially pronounced in connection with large-scale casein purification.

Thus it is surprising to find that ammonium sulphate in a concentration as low as 0.05 M in the separation of casein from the mixture of components, e.g. as described in Example 5, provided a very selective casein separation method as compared to conventional methods. The use of ammonium sulphate at the low concentration is inexpensive and may easily be used in large-scale isolation and/or purification of casein.

Although the various types of caseins, e.g. α-casein, β-casein, and κ-casein, cannot be separated from each other by use of the method disclosed above, it is believed that on the basis of the very selective casein separation method of the invention, the various types of caseins optionally present in this isolated casein precipitate can be further separated, if necessary by chromatography.

More particularly, the casein isolating method of the present invention may be used in the isolation of recombinant human β-casein from a mixture of bacterial or yeast cells in which it is produced, e.g. as disclosed above. Thus, in a further aspect, the present invention relates to a method of isolating recombinant human β-casein from bacterial or yeast cells as defined above which, in the case of intracellular expression of recombinant human β-casein in the bacterial or yeast cells, comprises separating the cells harboring the recombinant human β-casein from the culture medium, rupturing the separated cells so as to allow them to release their content of inter alia recombinant human β-casein, optionally removing cell debris from the mixture of ruptured cells and precipitating the released β-casein by addition of ammonium sulphate at a concentration equal to or above 0.05M.

The precipitate is consequently separated from the mixture in which it is present, the salt is optionally removed and the β-casein is concentrated, e.g. by freeze drying.

The separation of the bacterial or yeast cell from the culture medium, the optional removal of the cell debris, and the separation of the precipitate are conveniently carried out by centrifugation or by sedimentation or by other conventionally used separation methods. The rupturing of the bacterial or yeast cells may be accomplished by any suitable method such as by sonication, rupture by a freeze/thaw treatment, a French Press treatment or the like.

Any salt may be removed by conventional methods, e.g. by dialysis or size-exclusion chromatography. The isolated and optionally purified β-casein is preferably concentrated by ultrafiltration and/or lyophilization.

The β-casein precipitate may advantageously be subjected to one or more wash treatments before it is concentrated, or, in the event that the method comprises removal of salt, before this is done.

When the recombinant human β-casein has been produced extracellularly, it is in most cases not necessary to rupture the bacterial or yeast cells because the recombinant human β-casein has already been excreted into the medium. However, if the extra-cellular expression is not satisfactorily effective and a large part of the produced recombinant human β-casein is present in the cells, it may of course be an advantage to rupture such cells. However, normally when extra-cellular expression is concerned, the method of isolating recombinant human β-casein from bacterial or yeast cells as defined above comprises removing the bacterial or yeast cells from the culture medium, precipitating the recombinant human β-casein present in the culture medium by addition of ammonium sulphate in a concentration equal to or above 0.05M, separating the precipitated recombinant human β-casein from the medium, and optionally removing the salt and subjecting the isolated β-casein to concentration.

When recombinant human β-casein of the invention is to be separated from milk produced by a transgenic non-human mammal as described above, the ammonium sulphate is added directly to the milk and the precipitated casein comprising the recombinant human casein is recovered from the milk. The casein fraction which may comprise other types of casein than the recombinant human β-casein, e.g. bovine casein proteins, may be subjected to further purification so as to purify, e.g., the recombinant human β-casein therefrom, e.g. by chromatography or fractionated desalting. The ammonium sulphate concentration used in the purification method of the invention is preferably above 0.05M, such as equal to or above 0.06M, e.g. equal to or above 0.07M. However, also higher concentrations such as concentrations equal to or above 0.075M, 0.08M and even 0.09 and 0.1M are contemplated to be suitable for the purpose.

BRIEF DESCRIPTION OF THE DRAWINGS

The invention is further described with reference to the accompanying drawings in which FIGS. 1A–1B disclose the complete nucleotide and deduced amino acid sequences of the human β-casein cDNA fragment obtained as described in Example 1. The position of the oligonucleotide probe used for screening of the cDNA library is shown by underlining. The broken arrows show the positions of the different oligodeoxyribonucleotide primers used for sequencing of the cDNA fragment, FIG. 2 the human β-casein cDNA sequence useful for expression in E. coli and cloned as an EcoRI fragment into pUC 19 (as described in Example 2). The cDNA was modified by introduction of synthetic oligonucleotides in both the 5' and 3' termini. The modifications altered the codon usage in the 5' end, added an extra stop codon to the 3' end and introduced restriction sites which facilitate cloning into the expression vectors, FIG. 3 the expression vector pS 26 constructed as described in Example 2 and useful for intra-cellular expression of human β-casein in E. coli, FIG. 4 the expression vector pS 28 constructed as described in Example 2 and useful for extra-cellular expression of human β-casein in E. coli, FIGS. 5A–5B the result of an SDS-PAGE analysis of recombinant human β-casein expressed in E. coli BL21 (DE3) pLys S.

A) SDS-PAGE separation of soluble proteins from cytoplasmic and periplasmic preparations of IPTG induced E. coli BL21 (DE3) pLys S carrying the plasmids pS 26 and pS 28, respectively. The proteins were separated on a 10–17.5% gradient polyacrylamide gel followed by staining with Coomassie Brilliant Blue R-250.

Figure 2:
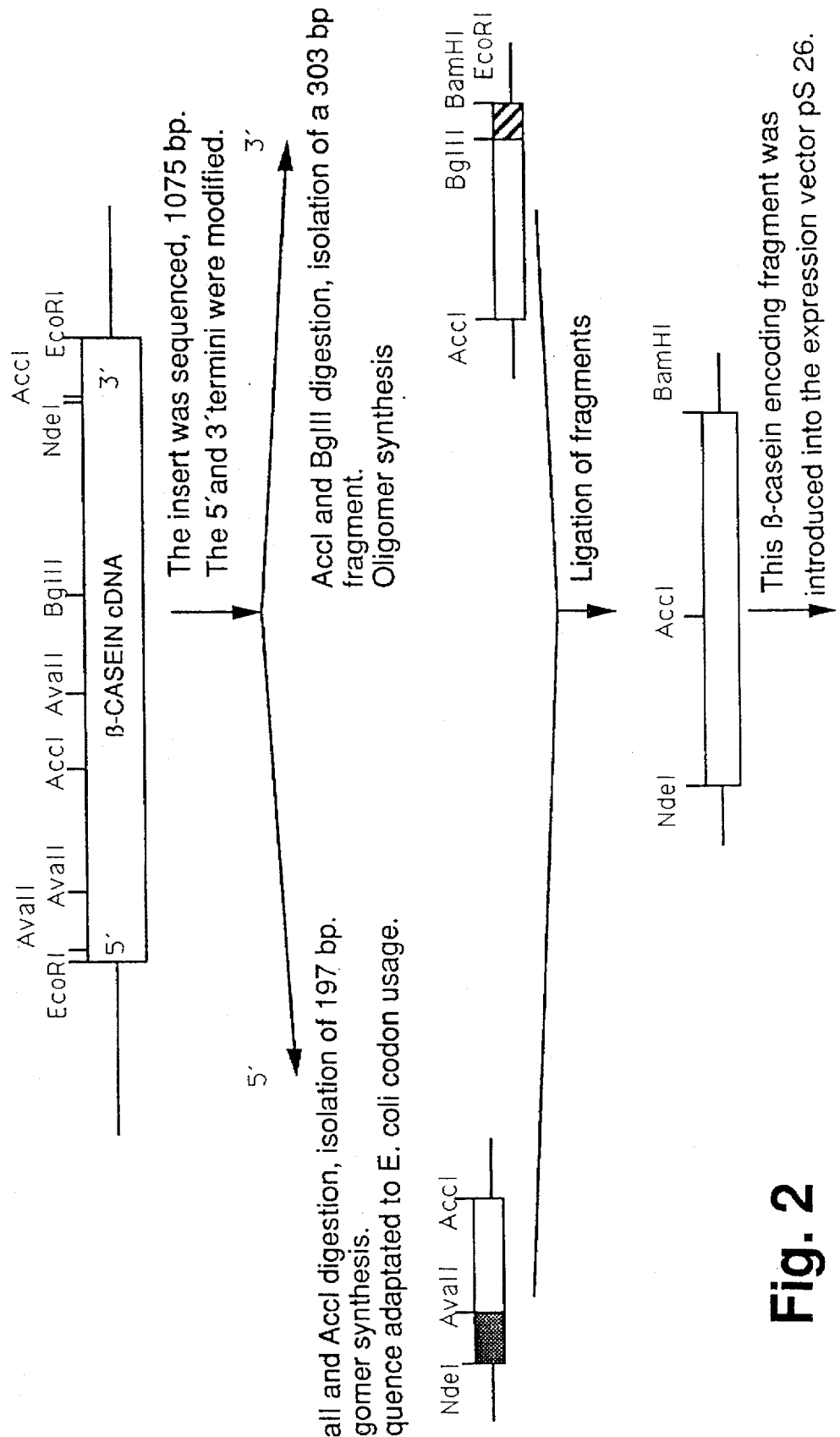

Lane 1: Molecular weight standard 94, 67, 43, 30, 20.1 and 14.4 kD (Pharmacia).

Lane 2: Cytoplasm from E. coli BL21 (DE3) pLys S carrying the plasmid pS 26 induced with IPTG.

Lane 3: As lane 2 but uninduced.

Lane 4: Periplasm from E. coli BL21 (DE3) pLys S carrying the plasmid pS 26 induced with IPTG.

Lane 5: As lane 4 but uninduced.

Lane 6: Cytoplasm from E. coli BL21 (DE3) pLys S carrying the plasmid pS 28 induced with IPTG.

Lane 7: As lane 6 but uninduced.

Lane 8: Periplasm from E. coli BL21 (DE3) pLys S carrying the plasmid pS 28 induced with IPTG.

Lane 9: As lane 8 but uninduced.

Lane 10: Native human β-casein prepared from milk.

B) Western blot analysis of recombinant human β-casein expressed in IPTG induced E. coli BL21 (DE3) pLys S carrying the plasmids pS 26 and pS 28, respectively.

The samples were separated by SDS-PAGE after one cycle of freezing/thawing in 40 mM Tris-HCl, pH 8.2, centrifugation and separation into pellet, unsoluble, and supernatant, soluble, fractions. The samples were then transferred to Immobilon (Millipore) membranes, visualized by using alkaline phosphatase labelled polyclonal rabbit antibodies produced using highly purified human β-casein.

Lane 1: Prestained molecular weight marker 106, 80, 49.5, 32.5, 27.5, and 18.5 kD (Bio-Rad).

Lane 2: Insoluble fraction from E. coli BL21 (DE3) pLys S carrying the plasmid pS 26 induced with IPTG.

Lane 3: As lane 2 but uninduced.

Lane 4: Soluble fraction from E. coli BL21 (DE3) pLys S carrying the plasmid pS 26 induced with IPTG.

Lane 5: As lane 4 but uninduced.

Lane 6: Insoluble fraction from E. coli BL21 (DE3) pLys S carrying the plasmid pS 28 induced with IPTG.

Lane 7: As lane 6 but uninduced.

Lane 8: Soluble fraction from E. coli BL21 (DE3) pLys S carrying the plasmid pS 28 induced with IPTG.

Lane 9: As lane 8 but uninduced.

Figure 6:
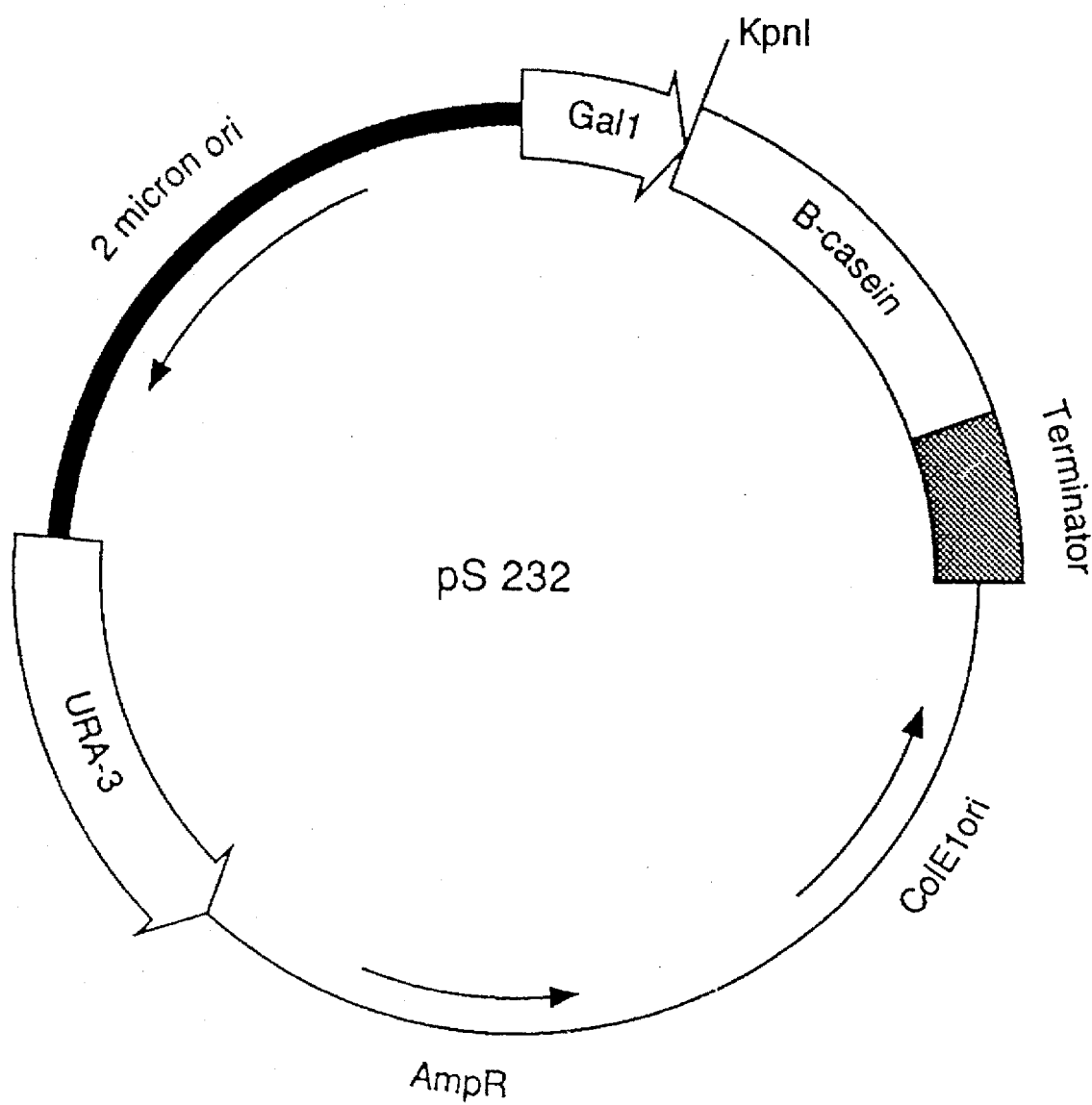
Figure 7:
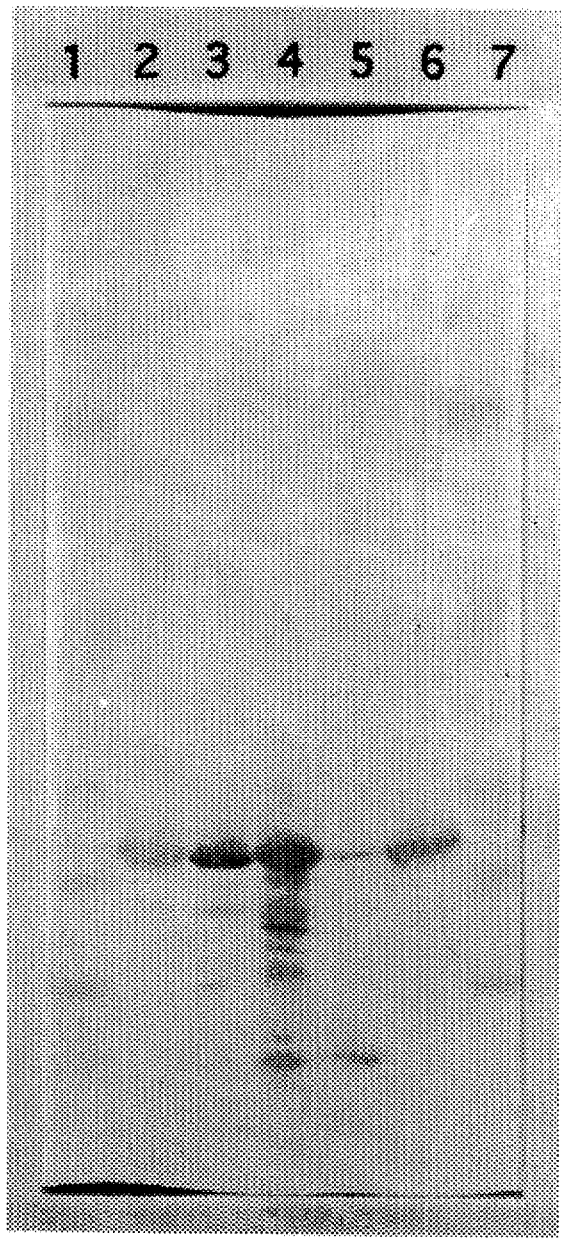

FIG. 6 the expression vector pS 232 used for extra-cellular expression of human β-casein in S. cerevisiae and further described in Example 6, FIG. 7 the result of an Western blot analysis of cell extracts from yeast cells containing the pS232 plasmid. The proteins were separated on a 10–17.5% gradient polyacrylamide gel followed by electroblotting to Immobilon (Millipore) membranes. Prior to development, the filter was blocked with 2.5% BSA. The β-caseins were visualized by using alkaline phosphatase labelled polyclonal rabbit antibodies produced using highly purified human β-casein. The filter was developed with nitro blue tetrazolium and 5-bromo-4-chloro-3-indolylphosphatase.

Lane 1: Prestained molecular weight marker 106, 80, 49.5, 32.5, 27.5, and 18.5 kD (Bio-Rad).

Lane 2: Native human β-casein prepared from milk.

Lane 3: Soluble fraction from E. coli BL21 (DE3) pLys S carrying the plasmid pS 26 induced with IPTG.

Lane 4: Soluble fraction from E. coli BL21 (DE3) pLys S carrying the plasmid pS 28 induced with IPTG.

Lane 5: Cell extract from yeast cells containing the pS232 plasmid.

Lane 6: Same as lane 2.

Lane 7: Same as lane 1.

FIGS. 8A–8B

Figure 10:
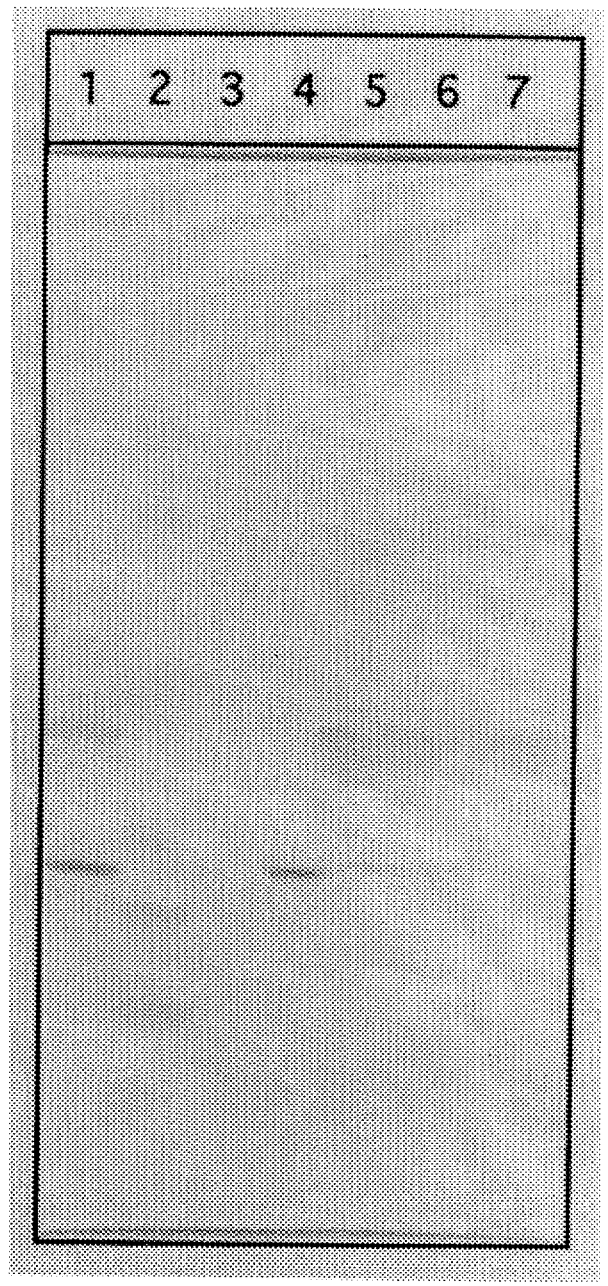

A) the organization of the human β-casein cDNA inserted into the mouse WAP gene as described in Example 4, B) the expression vector pS 133 used for expression of human β-casein in mice and constructed as described in Example 4, FIG. 9 the sequence of the KpnI and SalI fragment generated by PCR as described in Example 4, FIG. 10 the result of a Western blot analysis of milk samples derived from two mouse lines transgenic for human β-casein, carrying the pS316 derived vector fragment. The proteins are separated on SDS-PAGE transferred to Immobilon membranes (Millipore) and visualized by alkaline phosphatase labelled polyclonal rabbit antibodies produced using highly purified human β-casein. Lane 1 contains 1 µl of control milk from a non-β-casein transgenic line spiked with 500 ng of purified phosphorylated native human β-casein- Lane 2 contains molecular weight markers: 106, 80, 49.5, 32.5, 27.5, and 18.5 kD. Lane 3 contains approximately 100 ng of purified non-phosphorylated native human β-casein. Lane 4 contains 500 ng of purified phosphorylated native human β-casein, Lane 5 contains 2 µl of mouse milk derived from transgenic mouse line #93. Lane 6 contains 2 µl of mouse milk derived from transgenic mouse line #94. Lane 7 contains 2 µl of the same control non-β-casein transgenic mouse milk as in lane 1, without addition of purified human β-casein.

Figure 11A:
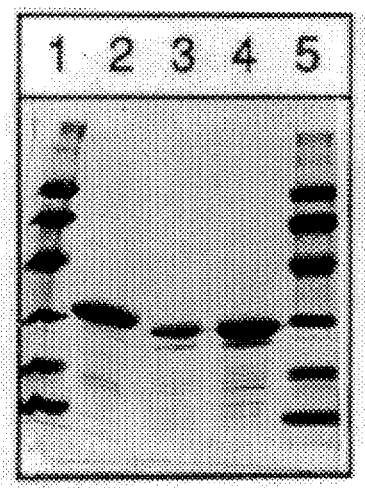
Figure 11B:
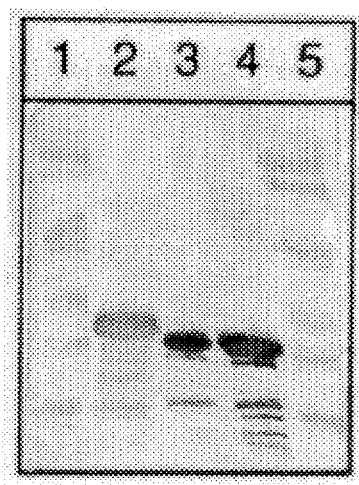

FIGS. 11A–11B the results obtained after purification of recombinant human β-casein as described in Example 5, A) SDS-PAGE analysis of purified recombinant β-casein produced in E. coli. The gel was stained with Coomassie Brilliant Blue R-250.

Lane 1: Low molecular weight standard (Pharmacia).

Lanes 2–4: Ammonium sulphate precipitated β-casein at increasing concentrations.

B) Western blot analysis of recombinant β-casein purified as in A).

Lanes 1 and 5: Prestained low molecular weight standard (BioRad).

Lane 2: Native β-casein purified from human milk.

Figure 12:
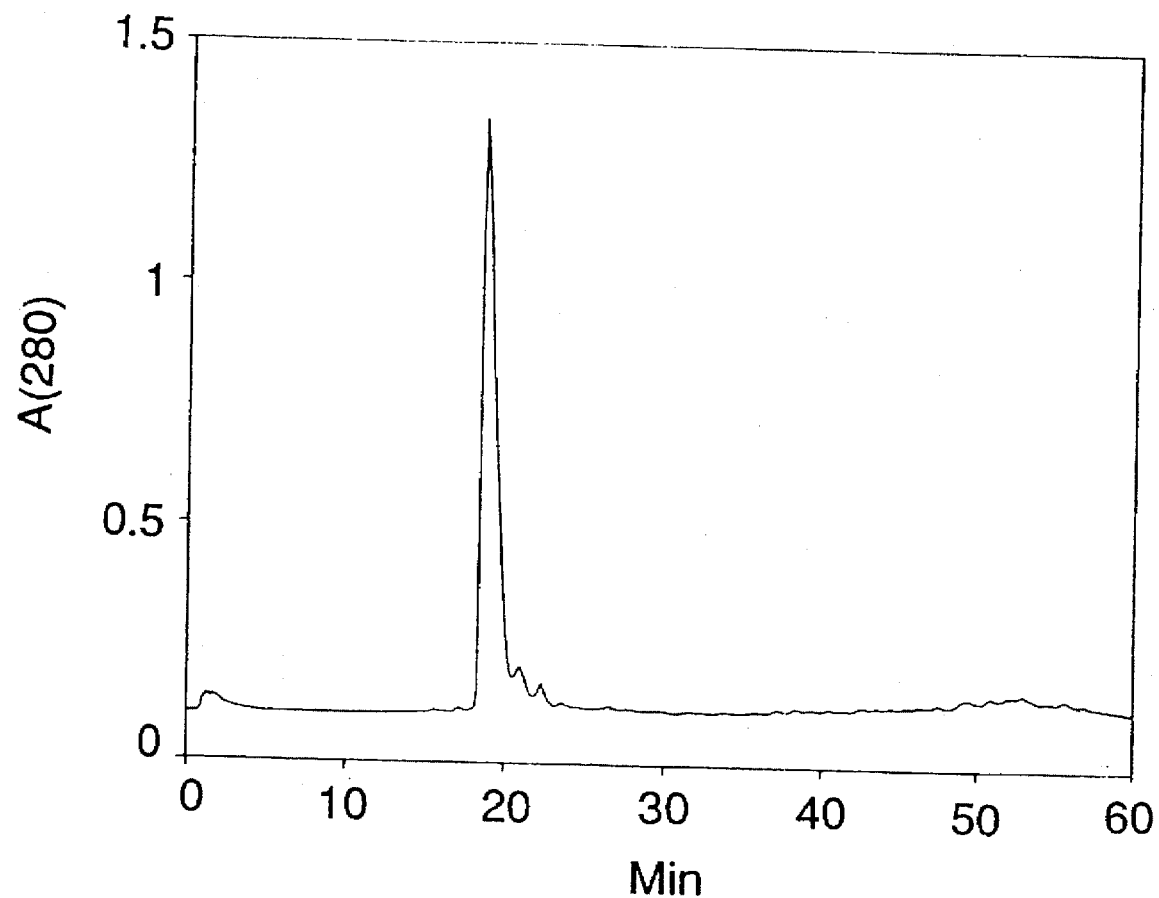

Lanes 3 and 4: Recombinant β-casein purified as in A),

FIG. 12 the purity of recombinant human β-casein purified as described in Example 5 and assayed by ion-exchange chromatography. The sample was loaded onto the column in 20 mM ethanolamine-HCl, 6M urea, pH 9.5 and eluted with a linear gradient up to 0.6M NaCl in the same buffer.

Figure 13:
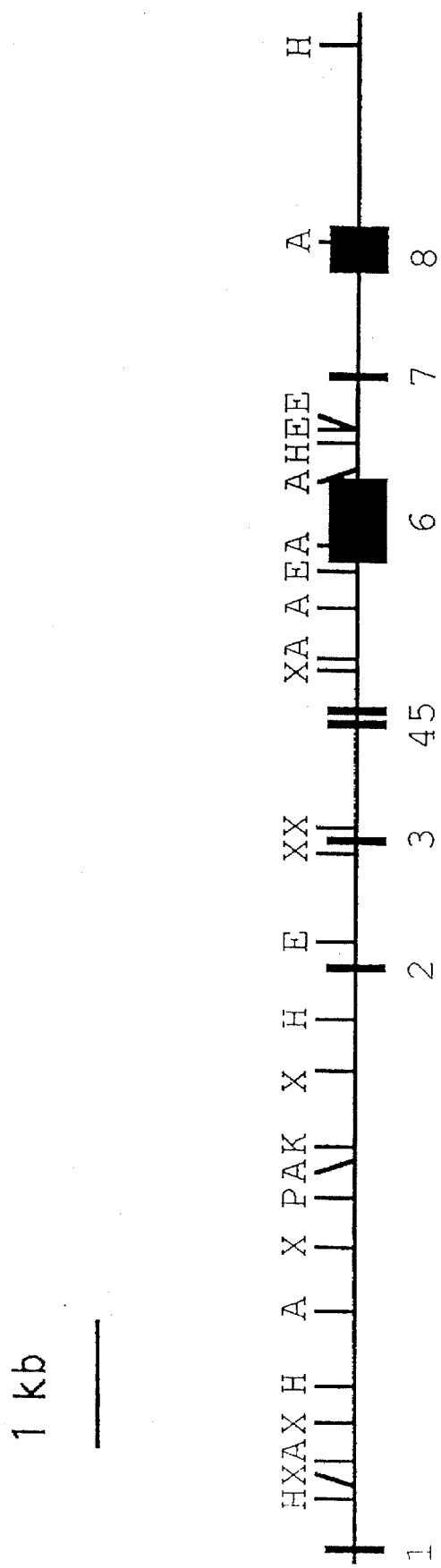
Figure 14:
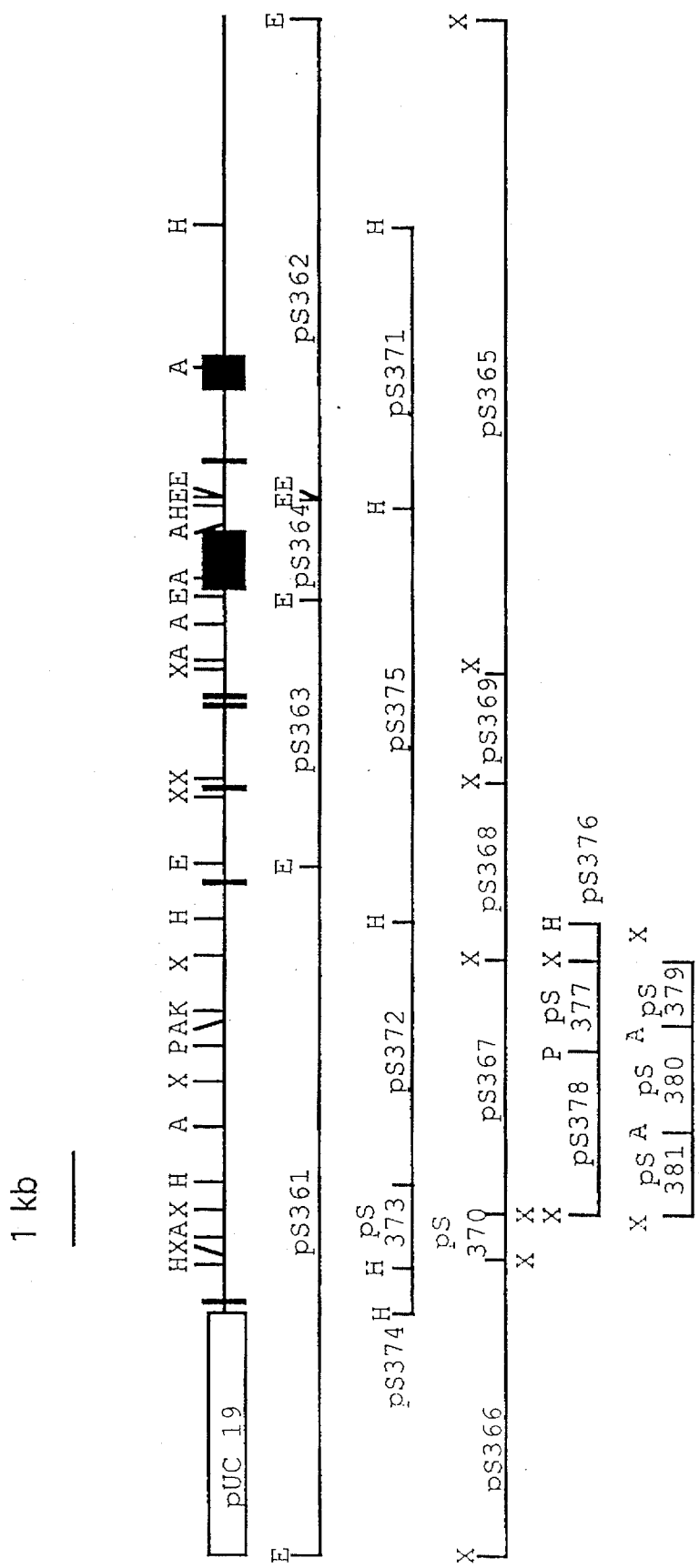

FIG. 13 the human β-casein gene locus. The exon/intron organization and used restriction enzyme sites are shown. Exons are indicated as solid boxes numbered 1–8. Enzymes used are A=AccI, E=EcoRI, H=HindIII, K=KpnI, P=PstI, X=XbaI, FIG. 14 the restriction map of the human β-casein gene and positions of the 21 different subclones, pS361–381 as indicated. Exons are shown as solid boxes.

pS361, pS362, pS363 and pS364 are different EcoRI fragments. pS365, pS366, pS367, pS368, pS369 and pS370 are different XbaI fragments.

pS371, pS372, pS373, pS374 and pS375 are different HindIII fragments.

pS376 is a XbaI/HindIII fragment, pS377 and pS378 are different PstI/XbaI fragments, pS379 and pS381 are different XbaI/AccI fragments and pS380 is an AccI fragment.

All fragments are subcloned into pUC19.

Two of the XbaI sites indicated in the restriction map are dam methylated and therefore not cleaved by XbaI treatment in the experiments.

Key: E=EcoRI, H=HindIII, X=XbaI, A=AccI, P=PstI and K=KpnI.

Figure 15:
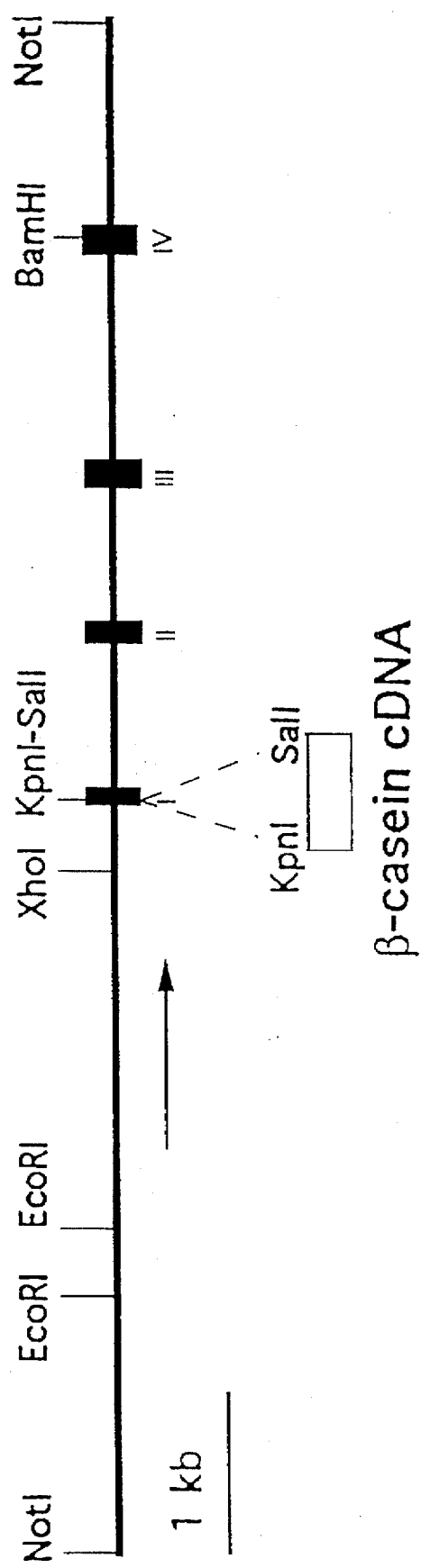

FIG. 15 organization of the WAP/β-casein recombinant gene in pS316. WAP exons are shown as solid boxes and numbered I–IV. The β-casein cDNA is shown as an open box and the restriction sites used for insertion of the cDNA, KpnI and SalI, are shown,

FIGS. 16A–16C

A) Schematic representation of the localization of the PCR primers used for identification of human β-casein transgenic animals. The 5' primer is positioned within the murine WAP sequence starting at the position −148 bp upstream of the fusion between WAP and β-casein. The 3' primer is localized in the first β-casein intron ending 546 bp downstream of the fusion point.

B) The sequences of the used PCR oligonucleotide primers.

C) Agarose gel showing a typical analysis of the PCR screening of the potential transgenic founder animals.

M: molecular weight markers, sizes in kb are indicated to the left.

Lane 1: control PCR product generated from pS316.

Lane 2: negative control, PCR analysis of DNA prepared from a non-transgenic mouse.

Lanes 3–16: PCR screening of DNA samples prepared from different potential transgenic founder animals. In lanes 5, 13 and 15 a PCR generated band is clearly visible, demonstrating DNA samples from transgenic animals in these samples. The expected size of the PCR product, 696 bp, is indicated to the right.

FIGS. 17A–17C

A) organization of the pS316 WAP/β-casein recombinant gene. The β-casein fragment indicated as an open box and the WAP exons are shown as solid boxes. The position of the labelled β-casein cDNA probe, EcoRI fragment isolated from pS21, used in the hybridization experiment is shown.

B) Ethidium-bromide stained agarose gel showing the separation of the DNA samples before transfer to filter membranes and hybridization. The amount of mouse derived DNA loaded in the various lanes is very similar.

M: molecular weight marker, sizes are indicated to the left.

Lane 1: 1 ng of XbaI/BglII digested pS316 DNA.

Lanes 2–16: 10 µg of XbaI/BglII digested DNA samples prepared from different potential β-casein transgenic founder animals.

C) DNA hybridization results, after transfer of the gel shown in B) and hybridization with the $^{32}$P-labelled probe which is the 1076 bp cDNA EcoRI fragment isolated from pS21 shown in A). The hybridization signal in lane 1 shows the expected sizes of the hybridizing XbaI/BglII fragments of the recombinant pS316 derived gene.

Figure 18:
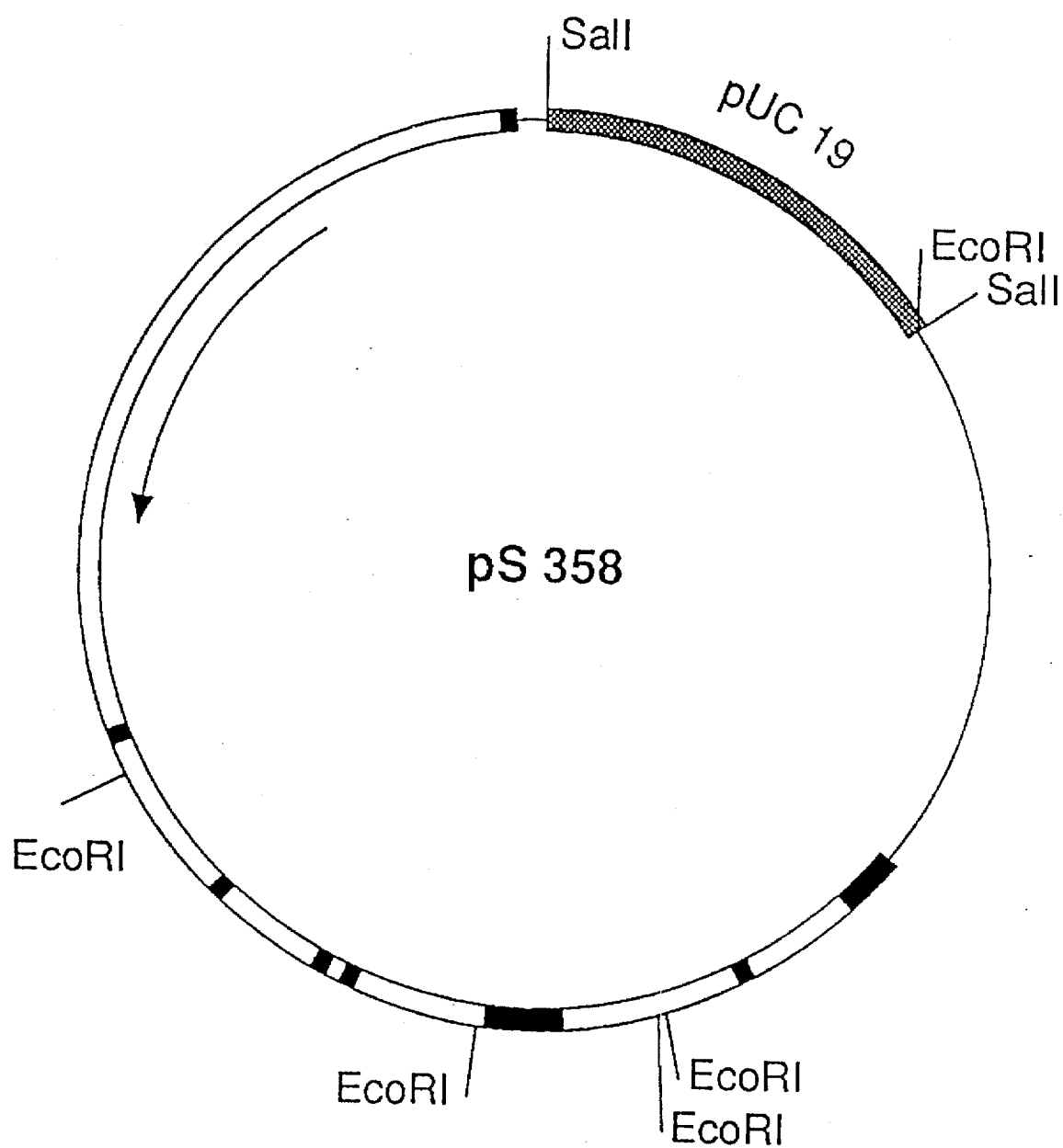

FIG. 18 a circular map of the plasmid pS358. pS358 contains the human β-casein genomic sequence derived from the purified λ phage cloned into SalI digested pUC19, as described in Example 1. EcoRI restriction sites are shown for orientation of the β-casein fragment. The arrow indicates the transcriptional direction of the β-casein gene.

Figure 19:
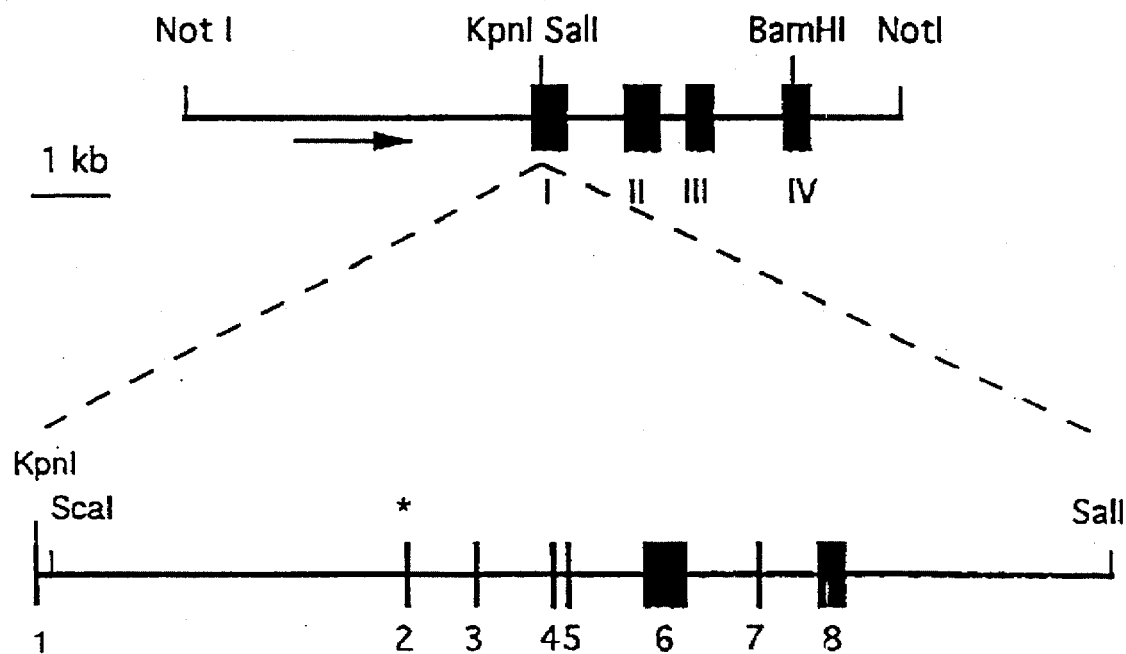

FIG. 19 a schematic map of the WAP/genomic β-casein construct containing the first β-casein exon, described in Example 4. The murine WAP gene fragment contains an approximately 4.5 kb DNA sequence upstream of the first exon. The transcriptional direction is indicated by an arrow. Some important restriction enzyme sites are indicated. The position of the KpnI and SalI sites in the first exon of the WAP sequence is used for introduction of the human β-casein genomic fragment containing all 8 exons. The position of the translation initiation site in the second exon of human β-casein is marked by an asterisk. Solid boxes represent exons and the numbers given below their order in the original genes.

Figure 20:
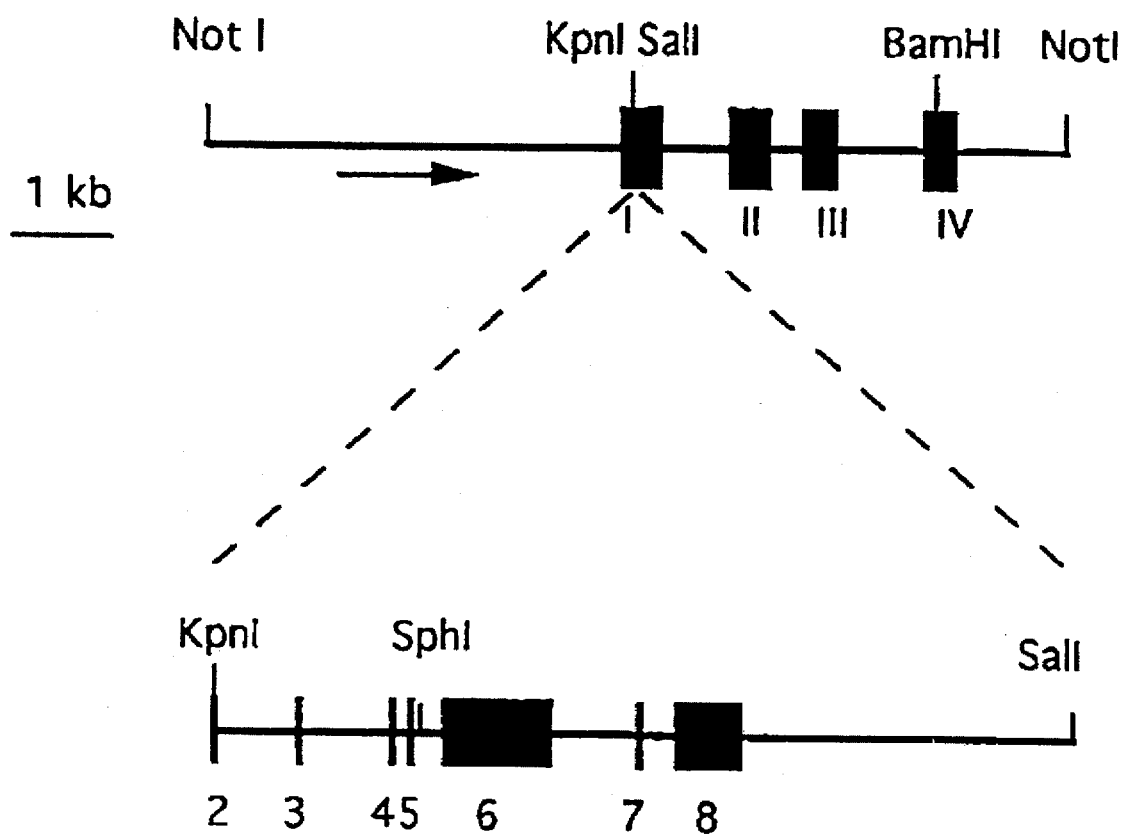

FIG. 20 schematic map of the second WAP/genomic β-casein construct in which the β-casein translational start localized in exon number 2 is inserted in the first WAP exon as described in Example 4. The exon 1 and the first intron of the human β-casein gene are thereby removed. The murine WAP gene fragment contains an approximately 4.5 kb DNA sequence upstream of the first exon. The transcriptional direction is indicated by an arrow. Some important restriction enzyme sites are indicated. The position of the KpnI and SalI sites in the first exon of the WAP sequence is used for introduction of the human β-casein 9enomic fragment containing 7 exons. Solid boxes represent exons and the numbers given below their order in the original genes.

REFERENCES

Blackburn, D. E., Hobbs, A. A. and Rosen, J. M. Rat beta casein cDNA: sequence analysis and evolutionary comparisons. Nucleic Acids Res. 10, 2295–2307, 1982.

Bonsing, J., Ring, J. M., Stewart, A. F. and Mackinlay, A. G. Complete nucleotide sequence of the bovine β-casein gene. Aust. J. Biol. Sci. 41, 527–537, 1988.

Bonsing, J. and Mackinlay, A. G. Recent studies on nucleotide sequences encoding the caseins. J. Dairy Res. 54, 447–461, 1987.

Brantl, V. Novel opioid peptides derived from human β-casein: Human β-casomorphins. Eur. J. Pharmacol. 106, 213–214, 1984.

Breatnach, R., Benoist, C., O'Hare, K., Gannon, F. and Chambon, P. Proc. Natal. Acad. Sci. USA 75, 4853–4857, 1978.

Brinster, R. L., Allen, J. M., Behringer, R. R., Gelinas, R. E. and Palmiter, R. D. Introns increase transcriptional efficiency in transgenic mice. Proc. Natl. Acad. Sci. USA 85, 836–840, 1988.

Campbell, S. M., Rosen, J. M., Hennighausen, L. G., Strech-Jurk, U. and Sippel, A. E. Comparison of the whey acidic protein Senes of the rat and mouse. Nucleic Acids Res. 12, 8685–8697, 1984.

Clarl, A. J., Simons, P., Wilmut, I. and Lathe, R. Pharmaceuticals from transgenic livestock. TIBTECH 5, 20–24, 1987.

Devinoy, E., Schaerer, E., Jolivet, G., Fontaine, M. L., Kraehenbuhl, J. P. and Houdebine, L. M. Sequence of the rabbit alpha S1-casein cDNA. Nucleic Acids Res. 16, 11813, 1988.

Gill, D. R., Hatfull, G. F. and Salmond, G. P. C. A new cell division operon in E. coli. Mol. Gen. Genet. 205, 134–145, 1986.

Greenberg, R., Groves, M. L. and Down, H. J. Human β-casein, amino acid sequence and identification of phosphorylation sites. J. Biol. Chem. 259, 5132–5138, 1984.

Hall, L., Emery, D. C., Davies, M. S., Parker, D. and Craig, R. K. Organization and sequence of the human alpha-lactalbumin gene. Biochem. J. 242, 735–42, 1987.

Hennighausen, L. G., Ruiz, L. and Wall, R. Transgenic animals—production of foreign proteins in milk. Curr. Opinions Biotechn. 1, 74–78, 1990.

Hogan, B., Constantini, F. and Lacy, E. Manipulating the Mouse Embryo. A Laboratory Manual. Cold Spring Harbor Laboratory Press, 1986.

Jiminez-Flores, R., Kang, Y. C. and Richardson, T. Biochem. Biophys. Res. Commun. 142, 617–621, 1987.

Jones, W. K., Yu-Lee, L. Y., Clift, S. M., Brown, T. L. and Rosen, J. M. The rat casein multigene family. Fine structure and evolution of the beta-casein gene. J. Biol. Chem. 260, 7042–7050, 1985.

Kohmura, M., Nio, N., Kubo, K., Minoshima, Y., Munekata, E. and Ariyoshi, Y. Inhibition of Angiotensin-converting enzyme by synthetic peptides of human β-casein. Agric. Biol. Chem. 53, 2107–2114, 1989.

Kunz, C. and Lönnerdal, B. Human milk proteins: analysis of casein and casein subunits by anion-exchange chromatography, gel electrophoresis, and specific staining methods. Am. J. Clin. Nutr. 51, 37–46, 1990.

Laemmli, U. K. Nature 227, 680, 1970.

Lönnerdal, B., Bergström, S., Andersson, Y., Hjalmarsson, K., Sundqvist, A. K. and Hernell, O. Cloning and sequencing of a cDNA encoding human milk β-casein. FEBS Lett. 269, 153–156, 1990.

Maruyama, S., Nakagomi, K., Tomizuka, N. and Suzuki, H. Angiotensin I-converting enzyme inhibitor derived from an enzymatic hydrolysate of casein. Isolation and bradykinin-potentiating activity on the uterus and the ileum of rats. Agric. Biol. Chem. 49, 1405–1410, 1985.

Menon, R. S. and Ham, R. G. Human β-casein: partial cDNA sequence and apparent polymorphism. Nucleic Acids Res. 17, 2869, 1989.

Miller, Mark J. S. et al., Proc. Soc. Exp. Biol. Med. 195, 143–159, 1990.

Mount, S. M. A catalogue of splice junction sequences. Nucleic Acid Research 10, 459–472, 1982.

Picken, R. N., Mazaitis, A. J., Maas, W. K., Rey, M. and Heyneker, H. Nucleotide sequence of the gene for heat-stable enterotoxin II of E. coli. Infect. Immun. 42, 269–275, 1983.

Provot, C., Persuy, M. A. and Mercier, J. C. Complete nucleotide sequence of ovine beta-casein cDNA: interspecies comparison. Biochimie 71, 827–32, 1989.

Rowland, S. J. J. Dairy Res. 9, 47–57, 1938.

Sambrook, J., Fritsch, E. F. and Maniatis, T. E. Molecular cloning, a laboratory manual. 2nd ed. Cold Spring Harbor Laboratory Press, 1989.

Schaerer, E., Devinoy, E., Kraehenbuhl, J. P. and Houdebine, L. M. Sequence of the rabbit beta-casein cDNA: comparison with other casein cDNA sequences. Nucleic Acids Res. 16, 11814, 1988.

Stewart, A. F., Bonsing, J., Beattie, C. W., Shah, F., Willis, I. M., Mackinlay, A. G. Complete nucleotide sequences of bovine alpha S2- and beta-casein cDNAs: comparisons with related sequences in other species. Mol. Biol. Evol. 4, 231–41, 1987.

Studier, F. W., Rosenberg, A. H., Dunn, J. J. and Dubendorff, J. W. Use of T7 RNA Polymerase to direct expression of cloned genes. In Methods in Enzymology, ed. David V. Goeddel, p. 60–89. Academic Press, 1990.

Yoshimura, M. and Oka, T. Isolation and structural analysis of the mouse beta-casein gene. Gene 78, 267–275, 1989.

Yoshimura, M., Banerjee, M. R. and Oka, T. Nucleotide sequence of a cDNA encoding mouse beta casein. Nucleic Acids Res. 14, 8224, 1986.

EXAMPLES

The following examples are intended to illustrate but not to limit the present invention.

Construction of the expression systems of the invention, and the molecular biological characterization of it, employs standard methods generally known in the art of recombinant DNA. Unless otherwise stated, the methods used are those described by Sambrook et al., 1989.

DEFINITIONS

Hybridization of DNA

DNA, e.g. present on nitrocellulose filters, are wetted in 2×SSC [1×SSC: 0.15M NaCl, 0.0015M Na$_3$-citrate, pH 7.0] and placed in a heat-sealed plastic bag with pre-warmed (67° C.) prehybridization solution. Prehybridization takes place for 2 h at 67° C., the bag being gently shaken. The solution is exchanged with pre-warmed (67° C.) hybridization solution, the radioactive probe is added and hybridization is carried out at 67° C. for 18 h. The bag is gently shaken to ensure constant movement of the liquid over the nitrocellulose filters. After hybridization, a washing procedure is carried out.

The radioactive probe is prepared by use of known methods, e.g. as described by Sambrook et al., on the basis of the DNA sequence shown in SEQ ID NO: 1 or SEQ ID NO: 3 or a part thereof, especially a coding part such as the nucleotides corresponding to amino acids 1-210 or an effective subsequence of the DNA sequence as defined above.

The prehybridization and hybridization solutions used are: 10×Denhardt's, 4×SSC, 0.1% SDS, 10 µg/ml polyA, 50 µg/ml of denatured DNA to be analysed and the denatured (heat) radioactive probe. The filters are washed in pre-warmed (67° C.) solutions: 10×Denhardt, 2×SSC, 0.1% SDS for 2×15 min. and 1×SSC, 0.1% SDS for 4×15 min. The filters are air-dried and covered with Vita-Wrap, and X-ray film is exposed to the filters for 3 h to 3 weeks with and without intensifying screens.

EXAMPLE 1A

Cloning and sequencing of cDNA encoding human β-casein

A λ-gt 11 human mammary gland cDNA library prepared from lactationally competent adult human mammary gland was obtained from Clontech Lab., Palo Alto, Calif. The clones of the human β-casein were screened by plaque hybridization using *E. coli* Y 1090. A synthetic 42-mer oligonucleotide probe 5'-GAGCAAGGGAAGAGGCAAATGAAGATTTTCAAGAT(ya##sized)by
(SEQ ID NO: 6)

corresponding to amino acids 117-130 in the β-casein sequence (Greenberg et al., 1984) was synthesized. The construction of this oligonucleotide was based on a region of the bovine β-casein amino acid sequence having a large degree of homology with the human counterpart. However, the selection of the synthetic oligonucleotide included the following modifications of the bovine cDNA sequence (Jiminez-Flores et al., 1987) for the nucleotide sequence 449-490: i) nucleotide 458 (G→C exchange), ii) nucleotide 480 (C→T), iii) nucleotide 483 (T→C). The oligonucleotide probe was synthesized on a Beckman 200A DNA synthesizer using the phophoramidite technique according to the vendor's instructions. The probe was [γ-$^{32}$P] dATP-labelled using T4 polynucleotide kinase (New England Biolabs; Beverly, Mass.). Hybridization was carried out for 12-15 hours at 40° C., and the membranes were washed and autoradiographed on X-ray film (Amersham, UK). Six positive plaques were identified in the primary screening. Following secondary screening, phage DNA of purified clones were isolated from plate lysates. Restriction mapping was performed and the β-casein cDNA was localized in the cloned fragment by Southern blotting.

One of the λ-gt 11 clones carrying an insert hybridizing to the β-casein 42-mer probe was digested with the restriction endonuclease EcoRI, and the cDNA insert was separated from DNA by electrophoresis in 1% Sea Kem GTGAgarose (FMC BioProducts, Me.). The cDNA fragment was ligated to EcoRI-digested alkaline phosphatase-treated pUC19 DNA (Pharmacia) and transformed into *E. coli* TG1 (Studier et al.). Transformants were selected on plates containing 100 µg/ml of carbenicillin, 40 µg/ml of 5-bromo-4-chloro-3-indolyl-β-D-galactoside (X-gal) and 1 mM isopropyl-β-D-thiogalactoside (IPTG, Sigma, St. Louis, Mo.). A recombinant plasmid carrying the cDNA insert was identified and designated pS 21. Plasmid pS 21 DNA was subjected to restriction endonuclease analysis. The complete nucleotide sequence of both strands of the region encoding β-casein was determined, using T7 sequencing kit (Pharmacia, Uppsala, Sweden), on double stranded templates as described by the vendor. As primers for sequencing reactions, specific oligonucleotides complementary to pUC19 or β-casein sequences were used.

The nucleotide sequence contained an open reading frame sufficient to encode the entire amino acid sequence of a β-casein precursor protein consisting of 210 amino acids and a signal peptide of 15 amino acids (FIG. 1).

EXAMPLE 1B

Genetic variants of human β-casein

It is assumed that human β-casein exists in a limited number of genetic variants. These variants will have a number of amino acid substitutions as compared to the amino acid sequence deduced from the cDNA sequence shown in FIG. 1. The assumption is based on the fact that most other species investigated to date do have genetic variants, but also on the discrepancies found between the obtained cDNA sequence (FIG. 1) and the sequence determined by classical amino acid sequencing (Greenberg et al.). Genetic variants, i.e. analogues of the DNA sequence shown in FIG. 1, may be isolated and characterized by the following procedure:

DNA is isolated from fresh human milk provided by donors with varying genetic background (ethnicity). Similarly, mRNA is isolated from fresh milk and cDNA is synthesized by use of the reverse transcriptase methodology. Using specific synthetic oligonucleotides, selected from regions flanking sequences with pronounced amino acid discrepancies, DNA fragments are synthesized by the use of the PCR technique. Synthesized DNA fragments are isolated from agarose gels and sequenced by the dideoxy chain-termination method.

Using this methodology, a number of human milk samples from donors in Sweden were analyzed. The obtained results showed that these individuals produce human β-casein containing the Gln$_{19}$ residue in their milk. This residue was reported by Greenberg et al. (1984), and the codon for this glutamine is included in the mRNA sequence submitted to GenBank (accession number X 17070) by R. S. Menon. The conclusion that this is the most abundant variant is further supported by the observation that β-casein sequences obtained from mammary gland cDNA libraries prepared from Scandinavian females encode this variant. At the gene level this difference can be explained by alternative splicing. The Gln codon, CAG, is located in the 5' end of exon 5. In the Gln$_{19}$ variant, exon 5 starts with the sequence 5'-CAGAAAGTT-3', whereas in the variant lacking Gln$_{19}$, exon 5 starts with 5'-ATT GTT GAG-3'. In both variants, the exon 5 splice sites conform to the Breatnach (GT/AG) rule and to the Mount consensus sequence (Mount et al., 1982). The identification of these two β-casein sequences may reflect that the samples were isolated at different stages of lactation or that there is a genetic variation within the population. Since the ethnical background is unknown for the donor from whom the Clontech cDNA library was prepared, the exact reason for the observed difference is not known.

EXAMPLE 1C

Cloning, sequencing and organization of the human β-casein gene.

A genomic clone containing the transcribed part of the human β-casein gene was isolated from a human genomic library using the cloned and described human β-casein cDNA as probe.

A human genomic library (catalog # HL 1067J, lot 1221) was obtained from Clontech (Palo Alto, USA). The library is constructed from human placenta DNA cloned into λ EMBL-3 vector. The average insert size is 15 kb, and the number of independent clones are $2.5 \times 10^6$.

In order to isolate a recombinant phage containing the exon and intron sequence of human β-casein 58 individual bacterial plates with a diameter of 150 mm, were screened.

The methods used were as described in the Library Protocol Handbook: General Procedures for the Hybridization of Lambda Phage Libraries w/DNA Probes (Clontech) with some modifications as will be apparent from the following.

The experiment was carried out essentially as follows. The numbers will be given per plate basis. A sample of the phage library diluted in 0.1 sterile lambda diluent was prepared in order to prepare an estimated 10,000 pfu. A 0.6 ml LB-medium culture of the E. coli host strain NM 539 (obtained from Clontech) was infected with the 10000 pfu (plaque forming units) recombinant library phages and 0.3M SM buffer was added. The infected culture was incubated for 20 minutes at 37° C.

The culture was then mixed with top agarose (7.2 g of agarose in LB) and poured onto LB plates. The plates were incubated at 37° C. for approximately 7 hours. The plates were chilled at 4° C.

Plaque hybridization experiments were as follows. Membrane filters, Colony/Plaque Screen (DuPont, USA), were placed onto the top of the plates for 2–3 minutes. The filters were removed and floated in 0.5M NaOH on a plastic wrap for 2 minutes, with the plaque side up, for denaturation of DNA. This step was repeated once to ensure efficient denaturation. The membrane filters were then transferred to a neutralizing solution, 1M Tris-HCl pH 7.5, for 2 minutes for two times to ensure efficient neutralization. The filter membranes were then allowed to dry.

To obtain a probe for DNA hybridization screening of the membrane filters, pS21 was digested with EcoRI and a 1075 bp fragment was separated by agarose electrophoresis, excised and transferred to a polypropylene microcentrifuge tube. The isolated cDNA fragment was $^{32}$P-labelled using multiprime DNA labelling system (Amersham) by the following procedure. Water was added at a ratio of 3 ml per gram of gel, and placed in a boiling water bath for 7 minutes to melt the gel and denature the DNA. The tube was then transferred to a water bath at 37° C. for at least 10 minutes. A volume of DNA/agarose solution containing 25 ng of DNA was added to the labelling reaction, according to the supplier's instructions.

The hybridization method was under stringent conditions at 65° C., according to the method described below. The filter membranes were prehydridized by treating in a solution of 1% SDS, 1M NaCl, 10% dextrane sulfate in a bottle using a hybridization oven (Hybaid) at 65° C. for at least 1 hour. Following prehydridization a solution containing denatured herring sperm DNA of a final concentration of 100 ng/ml and the $^{32}$P-labelled DNA probe at a concentration <10 ng/ml (for optimal signal to background ratio) was added to the prehybridization solution and the membrane filters were incubated at 65° C. for 10–20 hours. To wash the membrane filters the hybridization solution was removed. In the first step the membrane filters were washed in a 2×SSC (0.3M NaCl, 0.03M Na-citrate), 1% SDS solution two times for 5 minutes at room temperature. In the next step the membrane filters were incubated in the same solution for two times at 65° C. for 30 minutes. Finally, the membrane filters were then placed on a sheet of filter paper with the DNA face up, and allowed to dry. The dried membrane filters were then exposed to X-ray films and autoradiographed.

Of the approximately 600000 individual plaques analyzed as described, one hybridizing plaque was detected and isolated. After several re-screening experiments, the recombinant phage DNA was purified according to Sambrook et al. 1989. The purified DNA was digested with SalI and a fragment of about 14 kb was isolated by agarose electrophoresis. This 14 kb fragment was cloned into SalI digested linearized pUC19, resulting in pS358 (FIG. 19).

The cloned 14 kb fragment was characterized by restriction enzyme mapping, using EcoRI, HindIII, XbaI, AccI, PstI, KpnI, BglII, BamHI and SacI. The resulting restriction map is shown in FIG. 13. The approximate positions of the exons and the approximate size of the introns were analyzed by PCR and electrophoresis. The results generated from the pS358 clone were compared to results obtained with the same PCR primers using human DNA as template. The generated results from the two templates were identical.

In order to facilitate nucleotide sequence analysis, 21 restriction fragments derived from pS358 were isolated and subcloned into pUC19, resulting in pS361–pS381 (FIG. 15). The orientation of the subcloned fragment was determined by PCR analysis. The following strategy was employed, by combining PCR primers located within the pUC19 sequence at each side of the cloning site, separately, and the other PCR primer with defined orientation and specific for the β-casein derived subcloned fragment allowed the determination.

The inserts in the 21 plasmids pS361–381 were subjected to nucleotide sequence analysis. The complete nucleotide sequences for all subclones were determined using a T7 sequencing kit (Pharmacia, Sweden; United States Biochemical, USA) on double stranded templates as described by the vendors. As primers for sequencing reactions specific oligonucleotides complementary to pUC19 (E20 5'-GTTGGGTAACGCCAGGGTTTTC-3' (SEQ ID NO: 7), SYM 1121 5'-CAGGAAACAGCTATGAC-3' (SEQ ID NO: 8), SYM2589 5'-TTCCGGCTCGTATGTTGTGTGG-3' (SEQ ID NO: 9)) or β-casein (see Table 1) sequences were used.

TABLE 1

Oligonucleotide primers used for sequencing of the human β-casein gene. Sequences are given in 5' to 3' direction. Direction indicates the reading direction of sequence analysis. K indicates that the sequence is complementary to SEQ ID NO: 3.

| Primer | Location | Sequence | Direction | Nucleotides in SEQ ID NO: 3 |
|---|---|---|---|---|
| SYM 1202 | Exon 6 | CTGCCTCTTGCTCAGCCTGCT | 5'-3' | 8090–8110 |
| SYM 1206 | Exon 6 | GGCAGGACCACAGGAGGCTGA | 3'-5' | K 8101–8121 |
| SYM 1207 | Exon 8 | GTTCATGAGTCAAATTTCAA | 3'-5' | K 10343–10362 |
| SYM 1268 | Exon 6 | CTATCCCCCAGCAAGTGGTGC | 5'-3' | 8379–8399 |
| SYM 1269 | Exon 6 | AGGCAGGACTTTGGGCTGAGGA | 3'-5' | K 8359–8380 |
| SYM 2045 | Exon 6 | ttagacACTAATGGGGTTATGAACTG | 3'-5' | K 8502–8527 + 9440–9445 |
| SYM 2119 | Exon 6 | GTGTAGACAGTGTCTTTAGCTTTAGGGACTTCC | 3'-5' | K 8143–8175 |
| SYM 2255 | Exon 8 | AGTATTGAACTTCTGTGGTAC | 3'-5' | K 10394–10414 |
| SYM 2269 | Exon 6 | TTCCTCAGACTCTTGCACTT | 5'-3' | 8316–8335 |
| SYM 2270 | Exon 8 | GGAAAAGGCATCATATTTCC | 3'-5' | K 10217–10236 |
| SYM 2279 | Exon 6 | GGGGTAGATTTTATCCTGGTG | 3'-5' | K 7997–8017 |
| SYM 2760 | Exon 7 | GAAGATTTCAAAGTTAATTTTCCCTCC | 5'-3' | 9446–9472 |
| SYM 2887 | Exon 4 | CTTGTATTCTGTAATAGATTC | 3'-5' | K 6726–6746 |
| SYM 2891 | Exon 5 | CTCTCCTTGCTGCTGGTC | 3'-5' | K 6869–6886 |
| SYM 2904 | Exon 2 | CTTGCAAGAGCAAGAGCCA | 3'-5' | K 4382–4850 |
| SYM 3045 | Exon 1 | CACTACCTTCACTTCTCT | 5'-3' | 87–104 |
| SYM 3046 | Exon 1 | CGTTTTTCCAAGATTGAAG | 3'-5' | K 103–121 |
| SYM 3089 | Intron 7 | GGACTTCTCTAGGAGAAT | 3'-5' | K 9545–9562 |
| SYM 3090 | Intron 7 | CTGTTCTCTCCTCTTTTTAACC | 3'-5' | K 9923–9944 |
| SYM 3091 | Intron 7 | CAAGGGCCTATATACTTAC | 5'-3' | 9719–9737 |
| SYM 3092 | Intron 2 | CAGCCTAGGGCACTGGGTC | 5'-3' | 5214–5232 |
| SYM 3093 | Exon 8 | TTGAAATTTGACTCATGAAC | 5'-3' | 10343–10362 |
| SYM 3103 | Intron 4 | CTTTACAGATGGTAACATATC | 5'-3' | 6799–6819 |
| SYM 3104 | Intron 5 | GAGAATTTACTTTTCAACACAG | 3'-5' | K 7650–7671 |
| SYM 3108 | Intron 5 | TATTTTCTAGGATATGCATGC | 5'-3' | 7044–7064 |
| SYM 3110 | Exon 2 | ATGAAGGTCCTCATCCTCG | 5'-3' | 4804–4822 |
| SYM 3111 | Intron 1 | GAAGTTATATCACATGAAG | 3'-5' | K 4617–4635 |
| SYM 3112 | Exon 3 | CTGACTGCTTGAAAGGCTTTC | 3'-5' | K 5726–5746 |
| SYM 3113 | Intron 3 | CCACCATGCTCATTCCCTGAC | 3'-5' | K 6472–6492 |
| SYM 3118 | Intron 1 | CTTAATGGGGTAGAAAAGAC | 5'-3' | 783–802 |
| SYM 3120 | Exon 3 | GAAAGCCTTTCAAGCAGTGAG | 5'-3' | 5726–5746 |
| SYM 3121 | Exon 7 | CTTTGAAATCTTCTTAGAC | 3'-5' | K 9440–9458 |
| SYM 3124 | Intron 1 | GTCCATTCAGTATGATATTG | 5'-3' | 4161–4180 |
| SYM 3125 | Intron 1 | CATGAGTGAACTCCCATTC | 3'-5' | K 3820–3838 |
| SYM 3126 | Intron 1 | GAGAACATGTGGTGTTTGG | 5'-3' | 2280–2307 |
| SYM 3127 | Intron 1 | GAATCTACAATGTAACTCAAAC | 3'-5' | K 2921–2941 |
| SYM 3142 | Intron 1 | GAGTTGATTGTAGATTCTGG | 5'-3' | 2925–2944 |
| SYM 3143 | Intron 1 | CAGCATGGTACTTGGTACC | 3'-5' | K 3422–3440 |
| SYM 3148 | Intron 1 | CGC CACTCAAATCTTCATTCTC | 3'-5' | K 1381–1402 |
| SYM 3149 | Intron 1 | GAGGGATAGCATTAGGAGAT | 3'-5' | K 2170–2198 |
| SYM 3151 | Intron 1 | CTGAGACTTTGCTGAAGTTGC | 5'-3' | 3909–3929 |

The analyzed human β-casein genomic nucleotide sequence consists of 10607 bp (SEQ ID NO: 3).

This human β-casein gene fragment contains the complete exon and intron structure of the gene. The human β-casein gene consists of 8 exons and 7 introns, see Table 2. The translational start is localized in exon 2 (bp 4804), and the translational stop is localized in exon 7 (bp 9443). The exons are relatively small, the size range is between 21–531 bp, and the introns range in size from 98–4670 bp (see Table 2).

As can be noted from Table 3, all exon/intron boundaries are in accordance with the AG/GT rule and conform well to the consensus sequence suggested by Mount et al. 1982.

When the exon derived sequence was compared to the cDNA derived sequence, only one difference was observed, the 285 nt in exon 8, a C, which in the cDNA sequence is a T. Since this position is located downstream of the translational stop codon, this difference does not influence the amino acid sequence.

TABLE 2

Exon-Intron organization of the human β-casein gene Nucleotide position 1 was assigned to the G in the Sau3A (GATC) recognition sequence that is the fusion to the λ EMBL-3 arm, and the positions are given as the number of nucleotides from that (see SEQ ID NO: 3).

| EXON | | | INTRON | | |
|---|---|---|---|---|---|
| No. | Nucleotide position | Length | No. | Nucleotide position | Length |
| 1 | 87–121 | 35 | I | 122–4791 | 4670 |
| 2 | 4792–4854 | 63 | II | 4855–5719 | 865 |
| 3 | 5720–5746 | 27 | III | 5747–6725 | 979 |
| 4 | 6726–6746 | 21 | IV | 6747–6844 | 98 |
| 5 | 6845–6886 | 42 | V | 6887–7990 | 1104 |
| 6 | 7991–8521 | 531 | VI | 8522–9439 | 918 |
| 7 | 9440–9481 | 42 | VII | 9482–10202 | 721 |
| 8 | 10203–10539 | 337 | | | |

The murine (Yoshimura and Oka 1989) and bovine (Bonsing et al. 1988) β-casein gene organization has been described. Both the murine and bovine β-casein genes have 9 exons. However, the translational start is localized in exon 2 in both the murine and bovine gene as in the human β-casein gene. A comparison of the murine, bovine and human β-casein gene sequences reveals that the most pronounced homology is located within exon 2.

TABLE 3

Exon-Intron boundaries of the β-casein gene sequences at exon-intron junctions
5' splice donor    3' splice acceptor

| | |
|---|---|
| Exon1-Exon2 | GGAAAAACG gtaaga ... tcacag GACTTAGTA |
| Exon2-Exon3 | GCAAGGGAG gtatgt ... ccacag ACCATAGAA |
| Exon3-Exon4 | AGCAGTGAG gtaagt ... ctgtag GAATCTATT |
| Exon4-Exon5 | GAATACAAG gtaaat ... tagcag AAAGTTGAG |
| Exon5-Exon6 | CAAGGAGAG gtaatt ... ttccag GATGAACAC |
| Exon6-Exon7 | CCCATTAGT gtaagt ... tttaag GTCTAAGAG |
| Exon7-Exon8 | TTATTTTTG gtaagt ... ccacag AATTGACTG |

EXAMPLE 2

Expression of recombinant human β-casein in *Escherichia coli*

The cDNA encoding the pro-polypeptide for human β-casein was isolated as described above as a 1075 bp EcoRI fragment and cloned into pUC19, generating pS 21.

The cDNA termini were modified as follows (FIG. 2), pS 21 was digested with EcoRI and AccI and a 328 bp fragment was isolated by agarose gel electrophoresis. The isolated 328 bp fragment was purified from the agarose gel by electroelution and digested with AvaII, and an AvaII and AccI 197 bp fragment was isolated.

Oligonucleotides with suitable restriction sites and altered codon usage adapted for *E. coli* expression encoding the amino terminus of mature β-casein, SYM 1328, SYM 1329, SYM 1330, SYM 1331, SYM 1332 and SYM 1333, were synthesized. The sequences are listed below:

| | |
|---|---|
| SYM 1328 | 5'-CTCGAGCGAAGAATCGATCACCGAA-3' |
| | (SEQ ID NO: 10) |
| SYM 1329 | 5'-GAATTCATATGCGTGAAA-CCATCGAATCCCTGAG-3' |
| | (SEQ ID NO: 11) |
| SYM 1330 | 5'-TACAAAAAAGTTGAAAAA-GTTAAACACGAGGACCAG-3' |
| | (SEQ ID NO: 12) |
| SYM 1331 | 5'-CTTTTTTGTATTCGGTGAT-CGATTCTTCGCTCGAGCTCAGGGATT-3' |
| | (SEQ ID NO: 13) |
| SYM 1332 | 5'-GSTCCTGGTCCTCGTGTTTAACTTTTTCAA-3' |
| | (SEQ ID NO: 14) |
| SYM 1333 | 5'-CGATGGTTTCACGCATATGAATTCTGCA-3' |
| | (SEQ ID NO: 15) |

The six oligonucleotides described above were annealed and ligated into PstI and BamHI cleaved pUC19, and the resulting plasmid was sequenced and designated pS 24. An 89 bp PstI and AvaII restriction fragment was isolated from pS 24.

For modification of the 3' end, pS 21 was digested with AccI and a 641 bp fragment was isolated; this fragment was electroeluted and re-digested with BglII, and a 303 bp fragment was isolated. The 303 bp fragment was subcloned into AccI and BglII digested pS 2 (Symbicom), generating pS 22. pS 22 was digested with EcoRI and BglII, and a fragment of approximately 2.96 kb was isolated.

In order to introduce suitable restriction sites and modify the 3' untranslated sequence, oligonucleotides were synthesized and ligated with the 2.96 kb fragment derived from pS 22.

The following oligonucleotides were used:

| | |
|---|---|
| SYM 1335 | 5'-CCAGTTCATAACCCCATTA-GTGTCTAATAAGGATCCG-3' |
| | (SEQ ID NO: 16) |
| SYM 1336 | 5'-GATCTACCCTGTGACTCAGCCACTTGCC-3' |
| | (SEQ ID NO: 17) |
| SYM 1338 | 5'-AATTCGGATCCTTATTAGACACTATGG-3' |
| | (SEQ ID NO: 18) |
| SYM 1339 | 5'-GGTTATGTGAACTGGGGCAA-GTGGCTGAGTCACAGGGTA-3' |
| | (SEQ ID NO: 19) |

The resulting plasmid was sequenced and designated pS 23.

To obtain the modified fragment encoding the mature β-casein, the following three fragments were ligated: first a PstI and AccI fragment of approximately 3.0 kb derived from pS 23, second the PstI and AvaII 89 bp fragment derived from pS 24, and third the 197 bp AvaII and AccI fragment from pS 21, resulting in pS 25.

Figure 3:
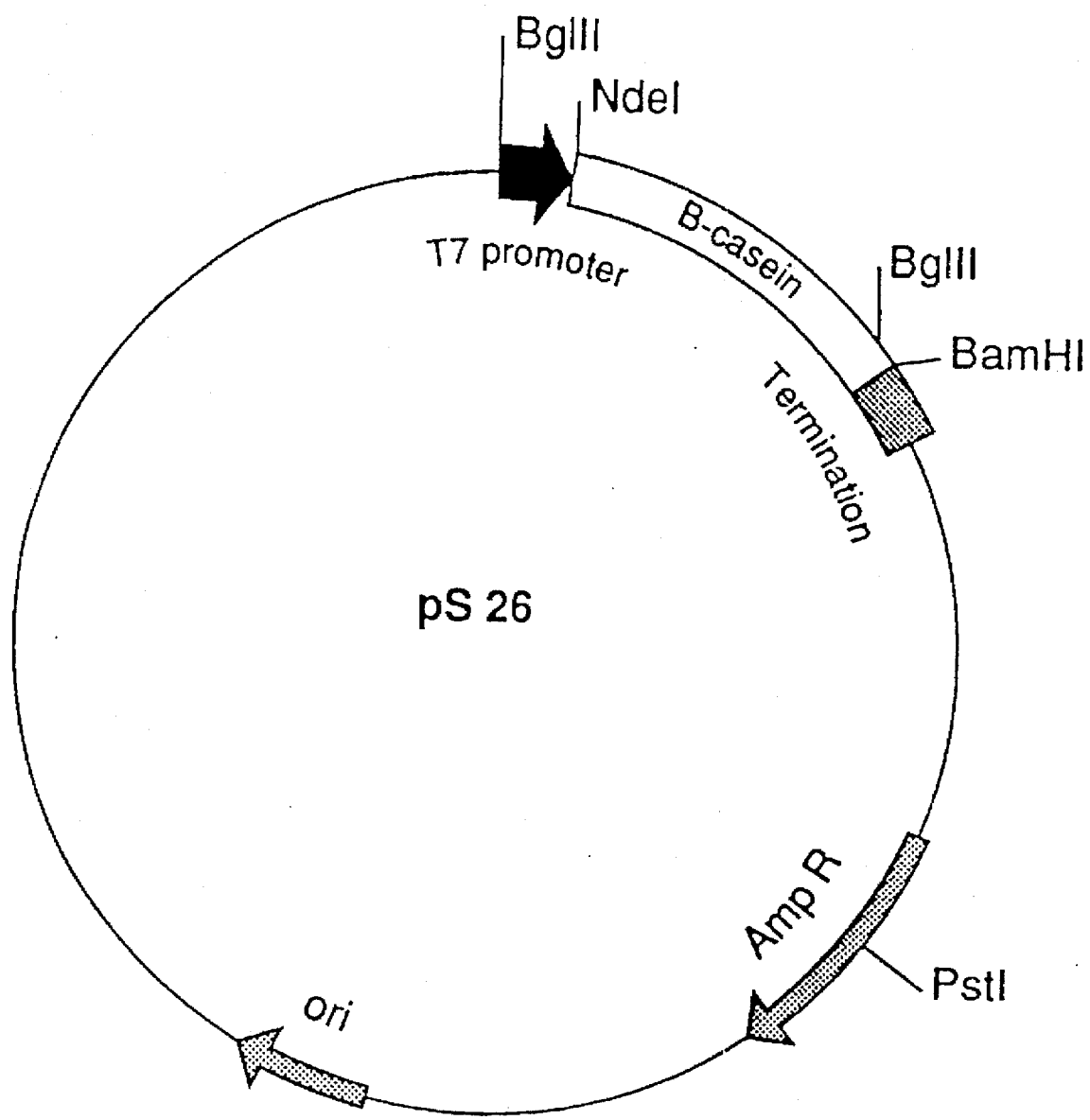

The β-casein encoding sequence without signal was isolated from pS 25 as a 641 bp NdeI and BamHI fragment and introduced into the NdeI and BamHI digested vector plasmid pS14, and the resulting β-casein expression vector was designated pS 26 (FIG. 3).

The vector pS 26 carries the bacteriophage T7 410 promoter and ø terminator (Studier, 1990) to regulate the expression of β-casein. It also contains the origin of replication and sequences encoding ampicillin and resistance of pBR322. This vector was analyzed with appropriate enzymes and relevant segments were sequenced.

In order to allow secretion of recombinant human β-casein, a sequence encoding the signal peptide of heat stable enterotoxin II, STII, of *Escherichia coli* was introduced.

pS 25 was digested with AvaI and EcoRI and a 619 bp fragment encoding the major part, except for the amino terminus, of β-casein was isolated. This fragment was cloned into NdeI and EcoRI cleaved pUC19 together with synthetic oligonucleotides. The synthetic oligonucleotides encode the very amino terminal end of mature β-casein with appropriate restriction sites allowing fusion with the STII signal sequence. The following oligonucleotides were used:

| | |
|---|---|
| SYM 1495 | 5'-TATGCACGTGAAACCATCGAATCCCTGAGC-3' |
| | (SEQ ID NO: 20) |
| SYM 1500 | 5'-TCGAGCTCAGGGATTCGATGGTTTCACGTGCA-3' |
| | (SEQ ID NO: 21) |

This three fragment ligation resulted in the plasmid pS 27. This plasmid was confirmed by sequence analysis.

Figure 4:
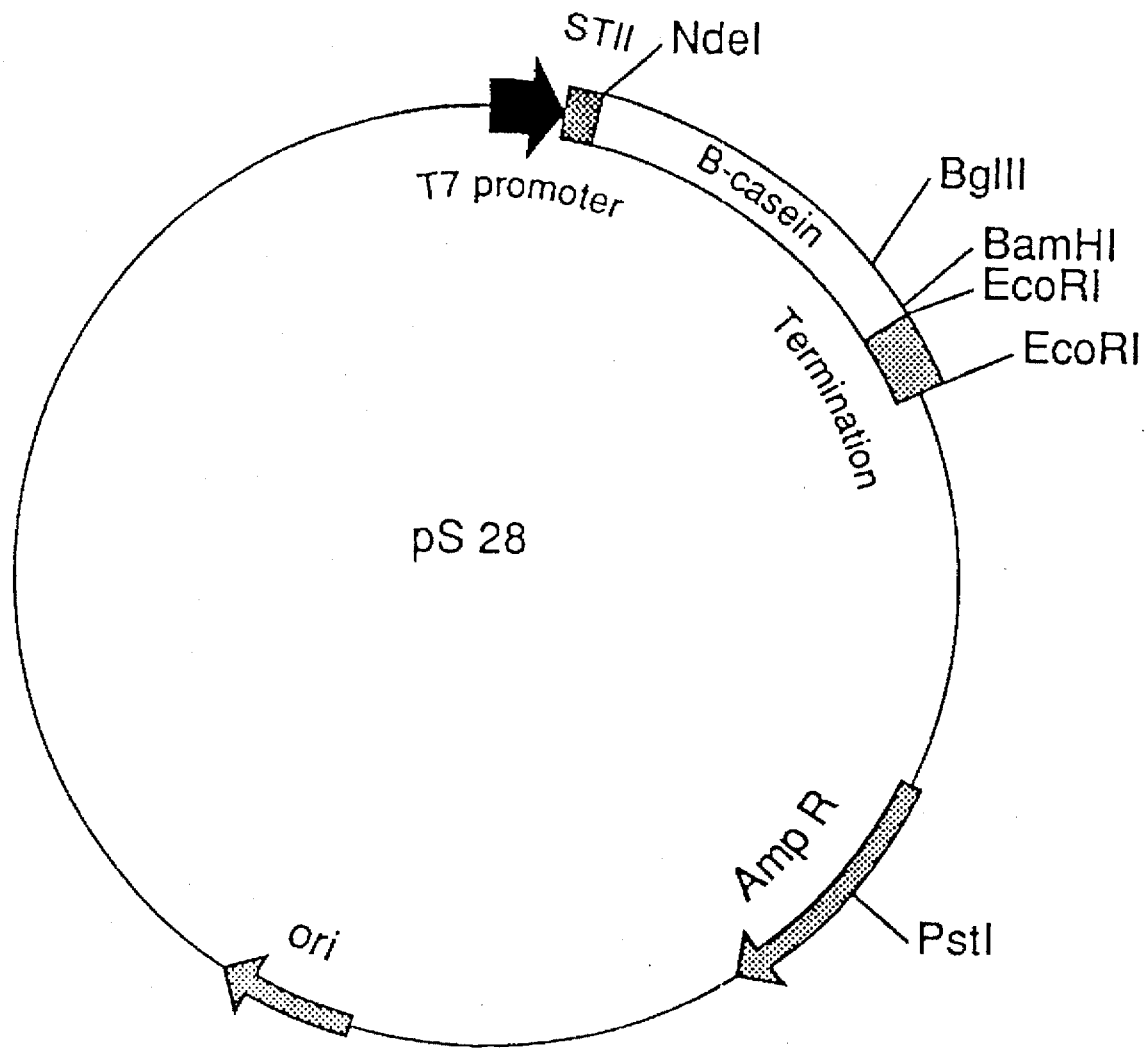

In the next step pS 27 was cleaved with NdeI and HindIII and a 700 bp fragment was isolated and sequenced. This 700 bp fragment was introduced into the STII containing expression vector pS 29 which was digested with HindIII and NdeI. The resulting expression vector for human recombinant β-casein was designated pS 28 (FIG. 4). pS 28 contains the same regulatory elements, replication signals and resistance markers as pS 26. The construction was confirmed by restriction analysis.

Figure 5A:
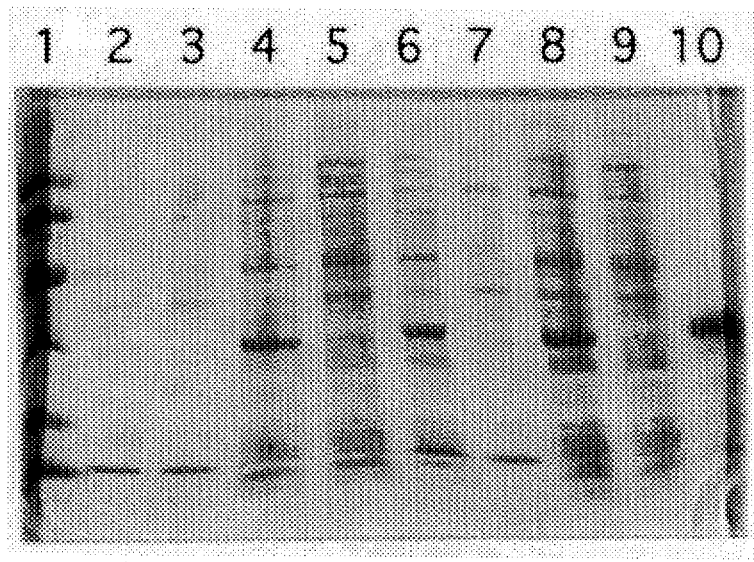
Figure 5B:
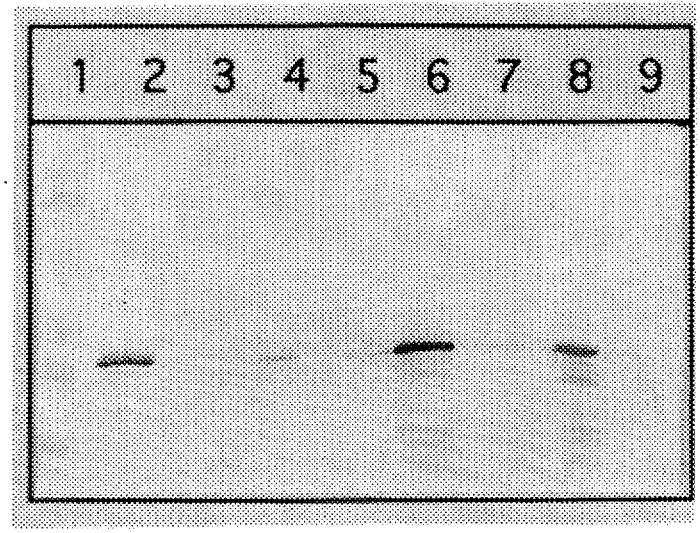

The expression vectors pS 26 and pS 28 were transformed into the following *Escherichia coli* strains: BL21(DE3), BL21(DE3) pLysE and BL21(DE3) pLysS (Studier, 1990). The expression experiments were carried out essentially as described by Studier et al., 1990. The obtained results demonstrated that recombinant human β-casein was efficiently expressed as a soluble protein with the two different expression vectors pS 26 and pS 28 (FIG. 5). However, the *E. coli* produced human β-casein shows a somewhat lower apparent molecular weight.

EXAMPLE 3

Expression of recombinant human β-casein in *Saccharomyces cerevisiae*

A fragment encoding the entire β-casein polypeptide was isolated as a 698 bp KpnI and SalI fragment from pS133 (FIG. 8, and further described in Example 4) by using agarose gel electrophoresis. The isolated fragment was ligated with KpnI and XhoI digested pYES2.0 (In Vitrogen Corporation, USA). The resulting β-casein expression vector, designated pS 232 (FIG. 6), was analyzed by restriction enzyme mapping.

The expression vector contains a polylinker and is designed for high level expression in *S. cerevisiae*. The vector is designed for maintenance in both *E. coli* and yeast.

The vector contains the Gal 1 portion of the Gal 1/Gal 10 promoter region from *S. cerevisiae* for inducible expression of genes inserted into the polylinker. It also contains the CYC1 transcription termination signal, the 2μ origin of replication and partitioning element and the URA 3 gene for selection in yeast. The ampicillin resistance gene and the replication origin derived from pUC 19 as well as the T7 RNA polymerase promoter and F1 origin are present for maintenance and selection, transcription and single strand rescue, respectively, in *E. coli*.

The Gal 1 promoter contains the sequences required for the regulation of transcription initiation as well as the mRNA start site, but does not contain an ATG for translation initiation. Therefore, the translation initiation must be located at the inserted sequence.

The expression vector pS 232 was transformed into the *Saccharomyces cerevisiae* host strain UMY 519 (URA⁻, Gal⁺) (A. Byström, personal communication), and selection was performed in uracil deficient medium. Colonies growing at restrictive conditions were isolated and analyzed.

A positive colony was cultured in minimal medium lacking uracil and containing 2% glucose to a density of about 0.5 $OD_{600}$. The culture was then centrifugated and the pellet was washed with distilled water. The washed pellet was divided. One part was resuspended in the same medium as above, and the other part was resuspended in the same medium except that glucose was substituted with 2% galactose. The two pellets were resuspended to a density of about 0.1 $OD_{600}$. The two cultures were grown overnight to a density of about 3.0 $OD_{600}$, and the cultures were harvested.

After centrifugation of the cultures, the pellets were resuspended and the supernatants were mixed with SDS, urea and mercaptoethanol containing sample buffer (Laemmli et al., 1970) and boiled for 20 minutes. The samples were then loaded on a SDS-PAGE 10–17.5% gradient gel (Laemmli et al., 1970). After separation the gels were either stained with Coomassie blue (Sigma, St. Louis, USA) or treated for protein transfer to nitrocellulose membranes for antibody detection using polyclonal rabbit anti-β-casein antibodies affinity purified on highly pure native casein coupled to an affinity gel. The obtained results demonstrated efficient expression of recombinant human β-casein in yeast. The samples were co-electrophoresed with purified native human β-casein (obtained by acid precipitated human native β-casein further purified by ion exchange chromatography (Rowland, 1938, Kunz and Lönnerdal, 1990)) and the recombinant molecules migrated in an identical manner, indicating correct and intact protein (FIG. 7).

The expression levels were estimated to be more than 50 mg per liter of culture of recombinant human β-casein.

EXAMPLE 4

Expression of recombinant human β-casein in transgenic mice

A plasmid containing the murine whey acidic protein, WAP, gene as a 7.2 kb genomic fragment cloned at EcoRI sites was obtained from Dr. Lotbar Hennighausen (Campbell et al. 1984). This plasmid was digested with EcoRI and KpnI and separated on agarose gel to obtain the approximately 2.6 kb upstream regulatory element. The plasmid was also cleaved with SalI and EcoRI, separated on agarose gel, and the fragment containing the third exon, the last intron, the fourth exon and downstream positioned mRNA processing signals as an approximately 2.3 kb large DNA fragment. These two fragments were cloned into a plasmid constructed as a fusion of pUC18 and pUC9 to eliminate the restriction sites in the polylinker except for the EcoRI site, together with a human cDNA fragment, generating pS88.

In order to facilitate cloning of human β-casein to the WAP regulatory elements by addition of KpnI and SalI sites and to introduce a sequence identical to the murine 5' untranslated upstream of the start codon, the original cDNA clone, pS21, was modified by using polymerase chain reaction.

Two PCR primers were synthesized, SYM2044 and SYM2045, with the following sequences:

SYM 2044
5'-CGGGTACCCTAAAGGACTTGACAGCCATGAAGGTCCTCATCCTCGCCTGCCTGG-3'
(SEQ ID NO: 22)

SYM 2045
5'-CGGTCGACTTAGACACTAATGGGGTTATGAACTG-3'
(SEQ ID NO: 23)

The plasmid pS21 was used as template in a polymerase chain reaction with the two primers.

Figure 8A:
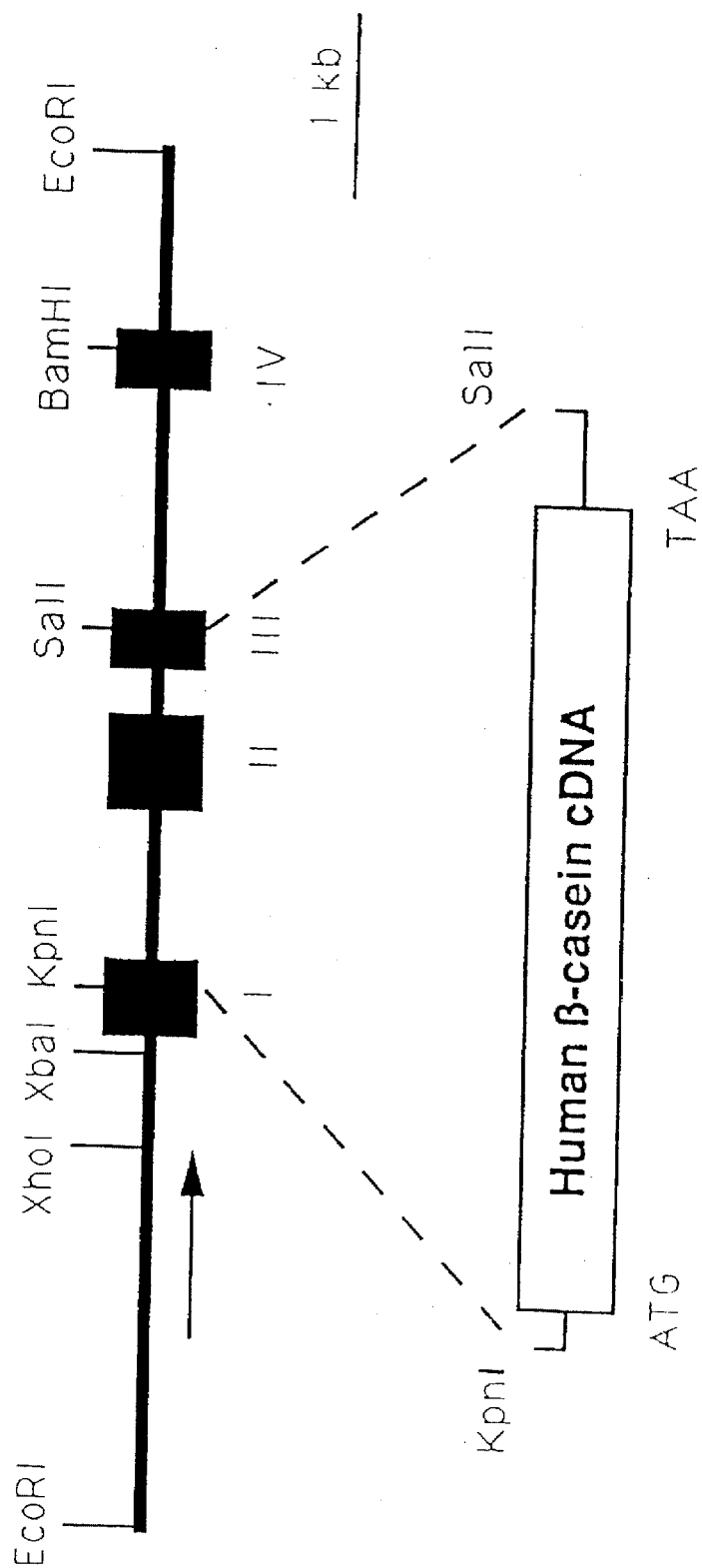
Figure 8B:
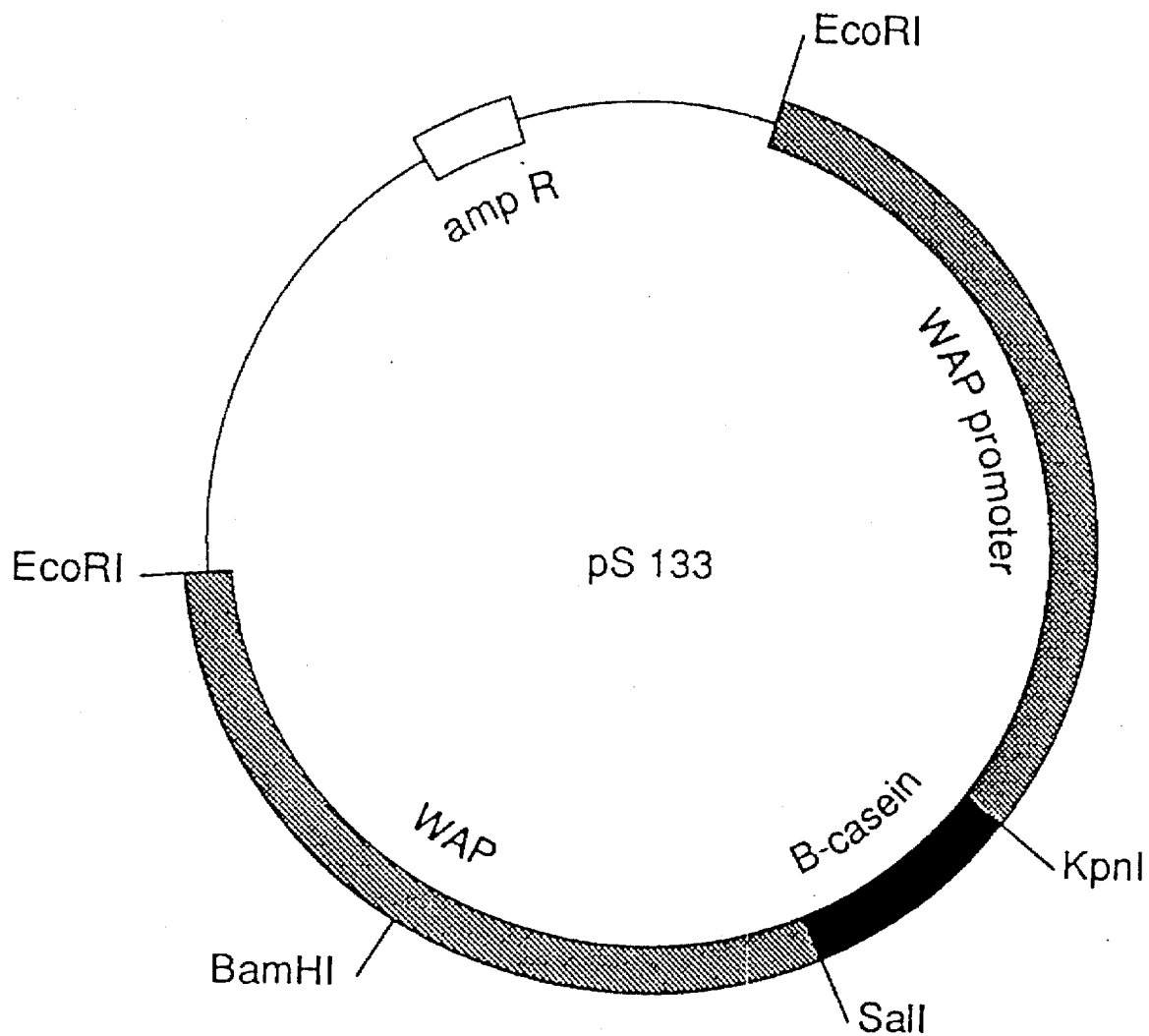

The obtained 698 bp fragment encoding human β-casein with a KpnI site in the 5' end and a SalI site in the 3' end and a modified 5' untranslated sequence was then cloned into the approximately 7.5 kb KpnI and SalI digested pS88 fragment and analyzed by DNA sequencing. The resulting expression vector was designated pS133 (FIG. 8). The sequence of the KpnI and SalI PCR generated fragment is listed in FIG. 9. One strand of the PCR fragment is listed as SEQ ID NO: 24, the other strand of the PCR fragment shown in FIG. 9 is complementary thereto.

The expression vector pS133 is capable to mediate stage and tissue specific expression of recombinant human β-casein in transgenic animals. The regulatory elements direct gene expression to the mammary gland during lactation thereby allowing isolation of the heterologous protein from milk.

Before injection of the expression vector into embryos, pS133 was digested with EcoRI and the WAP-β-casein fragment was isolated on agarose gel followed by electroelution. The eluted DNA was precipitated and redissolved in 10 mM Tris (pH 7.5) and 0.1 mM EDTA for microinjection.

Figure 16A:
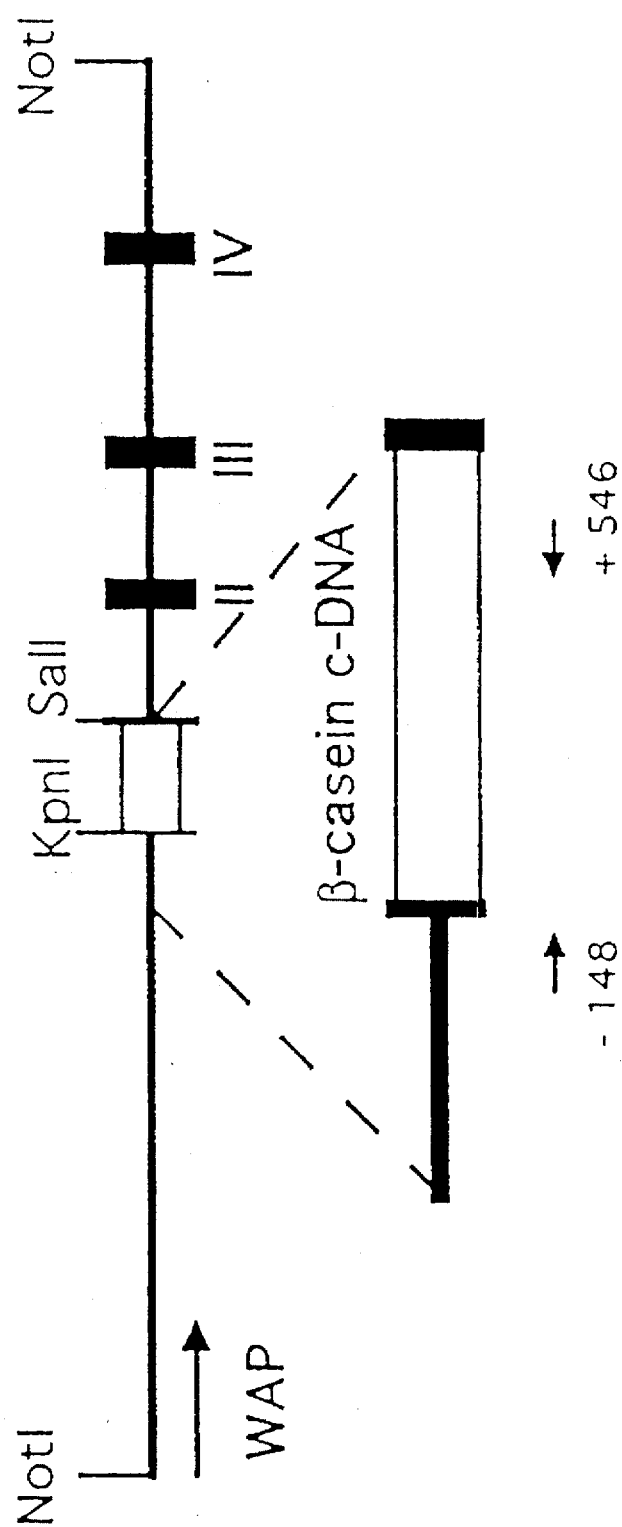
Figure 16C:
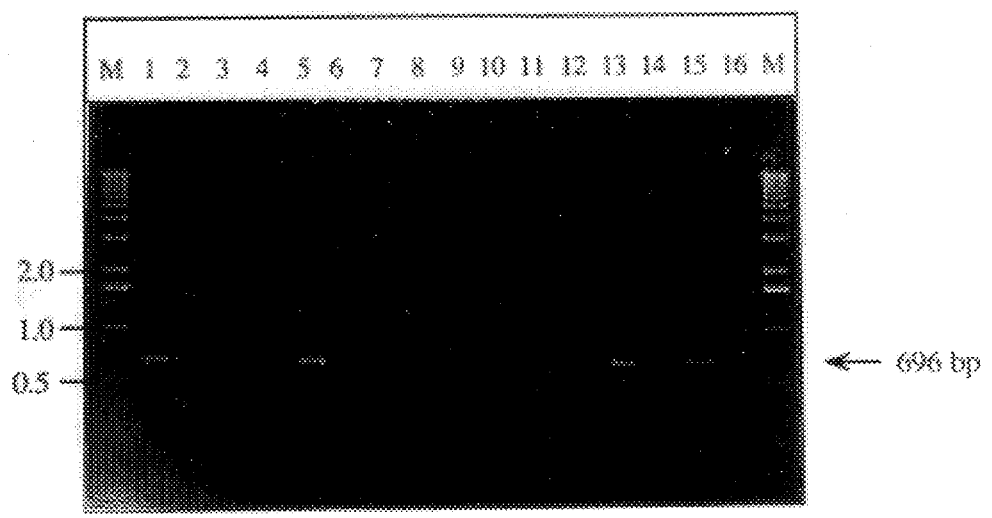

A variant of the vector element in pS133 was constructed, designated pS316 (FIG. 16). pS316 was modified with respect to three features compared to pS133. First, the WAP upstream regulatory element is longer, about 4.3 kb instead of 2.6 kb. Secondly, the β-casein cDNA fragment is inserted at the KpnI site in the first exon by introducing a cloning linker at this position, thereby leaving the rest of the WAP structure intact. Thirdly, the translational start, ATG, of human β-casein cDNA is cloned directly after the KpnI site without adding extra untranslated nucleotides.

To facilitate isolation of the WAP/β-casein fragment from plasmid pUC19 derived sequences, the flanking restriction sites were altered to NotI, since the pS316 fragment contains internal EcoRI sites.

For the production of a transgenic mouse containing genomic DNA, the plasmid pS358, containing human β-casein exon/intron genomic structure flanked by human β-casein upstream and downstream regulatory elements was digested with SalI, thereby providing a functional DNA fragment. This 14 kb fragment was isolated by agarose electrophoresis and electroeluted and precipitated and redissolved in 10 mM Tris (pH 7.5) and 0.1 mM EDTA for microinjection.

The experimental procedures employed to obtain transgenic animals is described in Hogan et al. 1986.

The isolated fragments were injected, at a concentration of 3 ng/μl, into the pronucleus of C57B1/6J×CBA/2J-$f_2$ embryos obtained from donor mice primed with 5 IU pregnant mare's serum gonadotropin and 48 hours later with 5 IU human chorion gonadotropin for superovulation. The C57B1/6J×CBA/2J-$f_2$ animals were obtained from Bomholtgaard Breeding and Research Center Ltd., Ry, Denmark. After collection of the embryos from the oviducts they were separated from the cumulus cells by treatment with hyaluronidase in the medium M2 (Hogan et al. 1986). After washing, the embryos were transferred to the medium M16 (Hogan et al. 1986) and kept in an incubator with 5% $CO_2$ atmosphere. The injections were performed in a microdrop of M2 under light paraffin oil using Narishigi hydrolic micromanipulators and a Nikon inverted microscope equipped with Nomarski optics. After injections healthy looking embryos were implanted into pseudopregnant C57B1/6J×CBA/2J-$f_1$ recipients given 0.37 ml of 2.5% avertin intraperitoneally.

Transgenic mice were identified by analysis of DNA prepared from excised tail samples. The tissue samples were incubated with proteinase K and phenol chloroform extracted. The isolated DNA was used in polymerase chain reactions with primers which amplify specific fragments if the heterologous introduced DNA representing the expression vector fragment is present. The animals were also analyzed by DNA hybridization experiments to confirm PCR data and to test for possible rearrangements, structure of the integrated vector elements and to obtain information about the copy number of integrated vector elements.

In one set of experiment 20 mice were analyzed with the two methods and the results demonstrated that 11 mice were carrying the heterologous DNA vector element derived from pS133. The result from the PCR analysis and the hybridization experiments were identical. No rearrangements were observed from the hybridization results, and the number of integrated vector copies show large variation, between 1 and 40 vector copies per cell.

Figure 17A:
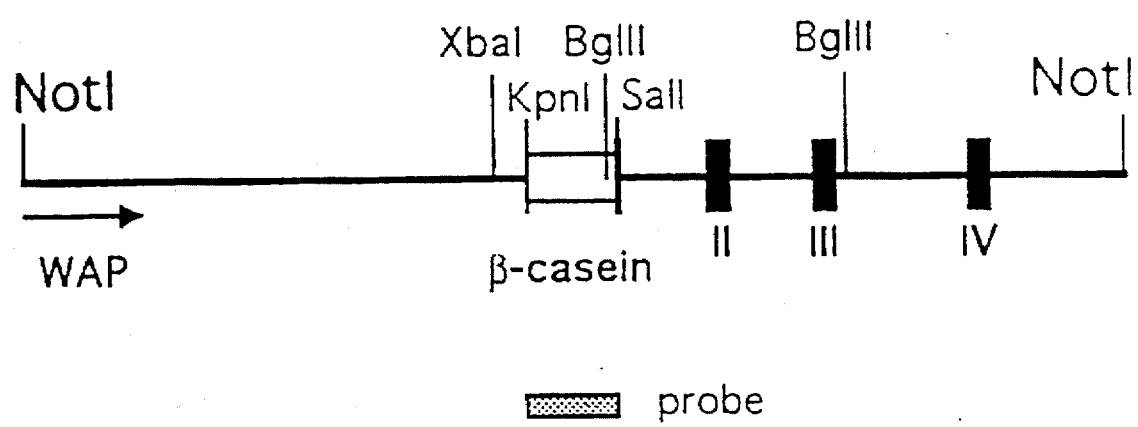
Figure 17B:
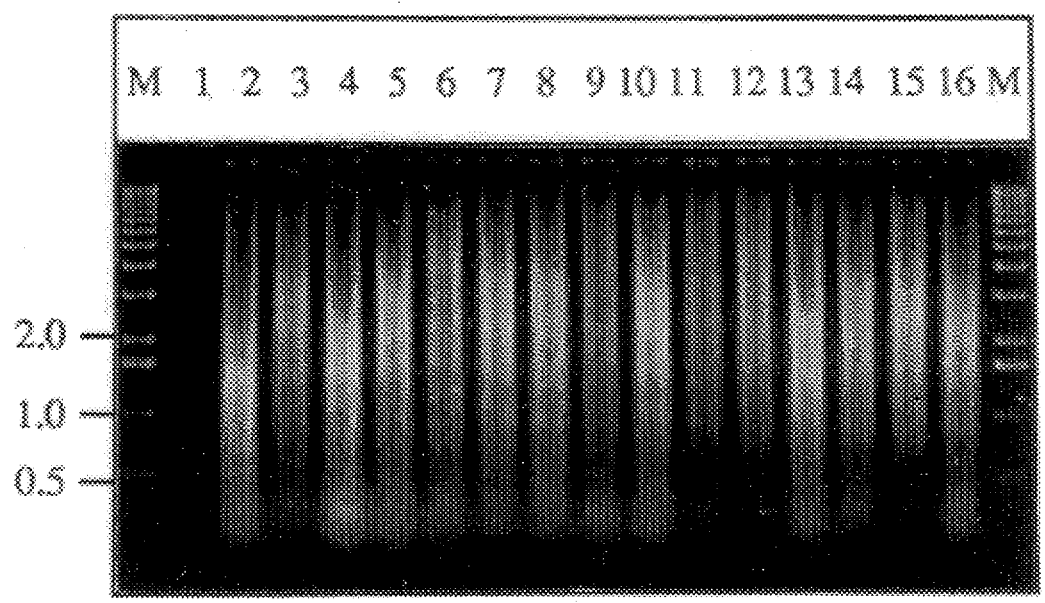
Figure 17C:
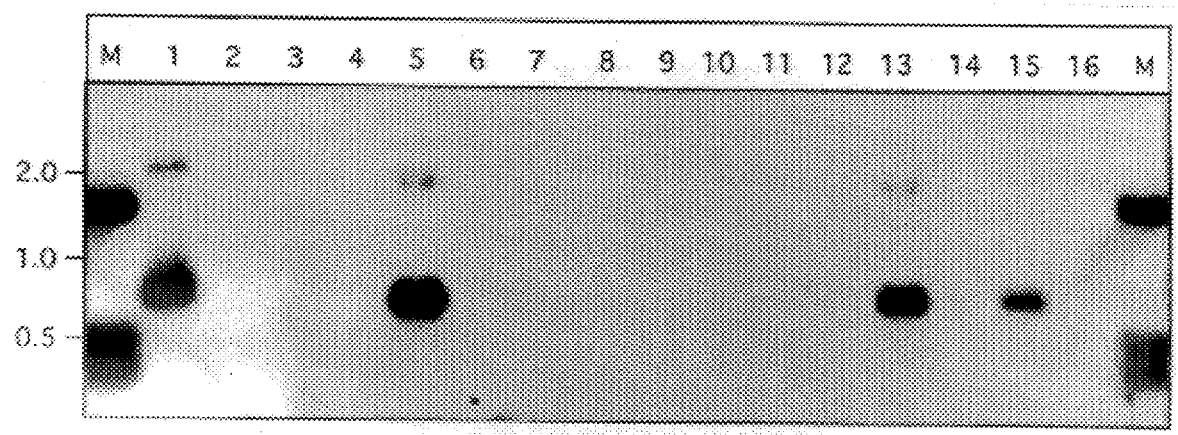

In another set of experiment the NotI fragment containing the vector element from pS316 was injected. 84 eggs were implanted into four foster mothers and 21 pups were borne. These potential founder animals were analysed by PCR (FIG. 17) and DNA hybridization (FIG. 18). Three animals were found to be transgenic, harbouring the recombinant WAP/β-casein vector element from pS316 (FIG. 17 and 18). Two animals were females and one was a male. The hybridization signal indicate variation regarding vector copy number between the founder animals (FIG. 18). No indications of rearrangement could be detected (FIG. 17 and 18).

In a third experiment 11 animals resulting from an injection experiment with the 14 kb SalI genomic human β-casein fragment, isolated from pS358, were analyzed as described above. The PCR primers used for this screening were SYM2887 and SYM 3120 (see Table 1). This resulted in identification of two transgenic founder animals carrying the human β-casein genomic fragment.

Progeny from all three experiments was established as follows.

The mice identified to carry vector DNA element, founder animals, were mated and the F1 litter were analyzed for transgene by the same procedures. Close to 50% of the progeny were found to be transgenic as is expected. Stable lines of transgenic animals have been generated. Milk samples were collected from female lactating animals injected with 2 IU oxytocin intraperitoneally, and 10 minutes later anaesthetized with 0.40 ml of 2.5% avertin intraperitoneally. A milk collecting device was attached to the nipple via a siliconized tubing and milk was collected into a 1.5 ml eppendorf tube by gentle massage of the mammary gland. The amount of milk varied, dependent of the day of lactation, between 0.1 and 0.5 ml per mouse and collection. The collected milk was analyzed for the presence of recombinant human β-casein. This was done by SDS-PAGE, transfer to nitrocellulose membranes and incubation with polyclonal antibodies generated against native human β-casein. The obtained results demonstrated expression of recombinant human β-casein in milk from transgenic mice carrying the DNA vector element derived from pS316 (FIG. 10). The expression levels are about the same in the two different transgenic animals analysis.

The recombinant β-casein produced in the transgenic animals showed identical migration on SDS-PAGE as compared to native human β-casein. Lower expression levels were obtained in animals transgenic for the DNA vector element derived from pS133.

In order to achieve high-level expression of recombinant human β-casein in milk from transgenic animals using the genomic fragment containing the human β-casein gene the following expression vectors are constructed.

The first expression vector will have the entire genomic sequence from exon 1 to exon 8 with all introns intact (nucleotide 87 to 10539 in SEQ ID NO: 3) under transcriptional control of the murine WAP upstream regulatory sequences. This is obtained by PCR mediated introduction of a KpnI site in front of β-casein exon 1 to facilitate ligation to the KpnI site located in the first exon of the murine WAP exon. The downstream regulatory elements and mRNA processing signals are provided by the human β-casein genomic fragment, the entire sequences to the 3' located SalI site (FIG. 19) is included in the vector. This vector construct is schematically illustrated in FIG. 20.

In summary, the vector are constructed by ligation of the following three fragments; first, a PCR fragment containing the 5' part of the β-casein gene with a KpnI site at the 5'-end of the first human β-casein exon to the unique ScaI site located in the first intron, second, the rest of the human β-casein gene and downstream elements isolated as a approximately 10.3 kb ScaI and SalI DNA fragment from pS358, third, the murine WAP upstream regulatory sequences and plasmid sequences for propagation of the vector in bacteria from KpnI and SalI digested pS316.

In the second expression vector the translation initiation located in exon 2 of the human β-casein gene is ligated directly to the KpnI site located in the first exon of the murine WAP gene. The natural translation initiation of murine WAP is located just downstream of the KpnI site. This vector is constructed in order to analyse if this position provides optimal translational start signals. The differences between this construct and the first vector are the lack of the first exon and intron of the human β-casein gene and the altered sequence in front of the translational start signal, ATG. This vector construct is schematically illustrated in FIG. 21.

This vector is constructed as follows. First, to introduce a KpnI site just before the translation initiation codon a synthetic oligonucleotide was synthesized. This 14 bp oligonucleotide contains the human β-casein sequence from the start codon, ATG, to the nearby positioned DraII site in exon 2. Another DNA fragment containing the human β-casein gene sequence from the DraII site in exon 2 to the unique SphI site located in intron 5 is isolated. These two fragments are introduced into KpnI and SphI digested pUC19, for sequence analysis. The resulting plasmid is then digested with KpnI and SphI and the human β-casein fragment of about 3.5 kb is isolated. The rest of the human β-casein gene is provided by digestion of pS358 with SphI and SalI and the fragment of approximately 3.5 kb is isolated. These two fragments are inserted into an expression vector under control of murine WAP upstream regulatory element. This is done by digestion of pS316 with KpnI and SalI and isolation of the approximately 12 kb fragment, and ligation of this fragment with the two fragments. The fragment generated from pS316 contains also plasmid sequences for propagation of the vector in bacteria.

EXAMPLE 5

Purification of recombinant β-casein from *E. coli*

*E. coli* cells expressing recombinant human β-casein and prepared as described in Example 2 above were separated from the culture by centrifugation and the resulting pellet was freezed and thawed several times so as to disrupt the cells. Other methods for cell disruption include osmotic shock, pressure change and sonication. After an additional centrifugation, the supernatant was collected and ammonium sulphate at varying concentration starting from 0.05M was added so as to precipitate β-casein.

SDS-polyacrylamide gels (10–17%) (FIG. 11A) as well as liquid chromatography (FIG. 12) were run to analyze purity and Western blots (FIG. 11B) to analyze identity. Antibodies used in Western blots were raised in rabbits using highly purified native human β-casein, purified from milk as described in Example 2 above, and purified by affinity chromatography on immobilized human β-casein. No cross-reactivity was seen with host proteins.

EXAMPLE 6

In vitro maturation, fertilization and culture of bovine oocytes

Immature oocytes are obtained in large quantity (400–600/day) by aspirating follicles of ovaries obtained at abattoirs. Immature oocytes are cultures for a period in vitro before they are competent to be fertilized. Once "matured", oocytes are fertilized with sperm which has also been matured, or "capacitated" in vitro. The pronuclei of the fertilized oocyte is then injected with the transgene coding for the expression and secretion of human β-casein. Zygotes resulting from this in vitro fertilization and microinjection are then cultured to the late morula or blastocyst stage (5–6 days) in medium prepared, or "conditioned" by oviductal tissue. Blastocysts are then transferred non-surgically to recipient bovine species for the balance of gestation and analyzed for integration of the transgene as described herein.

In vitro maturation (IVM)

Ovaries are obtained immediately after slaughter at local abattoirs and oocytes are recovered. Alternatively, oocytes are obtained from living bovine species by surgical, endoscopic, or transvaginal ultrasonic approaches. In all cases, oocytes are aspirated from ovarian follicles (2–10 mm diameter). After washing, oocytes are placed in a maturation medium such as a medium consisting of M199 supplemented with 10% fetal calf serum, and incubated for 24 hours at 39° C. (Sirard et al. (1988) *Biol. Reprod.* 39, 546–552).

In vitro fertilization (IVF)

Matured oocytes are fertilized with either fresh or thawed sperm. Sperm is prepared for fertilization by first obtaining a population of sperm enriched for motility by a "swim-up" separation technique (Parrish et al. (1986) *Theriogenology* 25, 591–600). Motile sperm is then added to a fertilization medium, consisting of a modified Tyrode's solution (Parrish et al. (1986) supra) supplemented with heparin to induce sperm capacitation (Parrish et al. (1988) *Biol. Reprod.* 38, 1171–1180). Capacitation constitutes the final sperm maturation process which is essential for fertilization. Sperm and oocytes are co-cultured for 18 hours. A useful feature of this IVF method is that (in the case of frozen sperm) consistent, repeatable results are obtained once optimal fertilization conditions for a particular ejaculate have been defined (Parrish et al. (1986) supra).

In vitro culture (IVC)

Conventional culture systems, which support development of murine, rabbit, or human ova, do not support development of bovine embryos past the 8–16 cell stage. This problem has been overcome by pre-conditioning culture media with oviductal tissue. Oviduct-conditioned medium will support bovine embryos past the 8–16 cell stage to the blastocyst stage in vitro (Eyestone and First (1989) *J. Reprod. Fert.* 85, 715–720) .

Bovine embryos did not yield to attempts to culture them in vitro past the 8–16 cell "block" until Camous et al. (1984) *J. Reprod. Fert.* 72, 479–485 demonstrated cleavage to 216 cells when embryos were co-cultured with trophoblastic tissue.

The co-culture procedure was extended to oviductal tissue, based on the ability of homo- or hetero-oviducts to support development from zygote to blastocyst. Thus, bovine embryos co-cultured with oviductal tissue, or in medium conditioned by oviductal tissue, developed from zygote to blastocyst in vitro (Eyestone and First (1989) *J. Reprod. Fert.* 85, 715–720; Eyestone, W. H. (1989) "Factors affecting the development of early bovine embryos in vivo and in vitro." Ph.D. Thesis, University of Wisconsin). Blastocysts have been produced in this system after superovulation and artificial insemination, or by in vitro maturation (IVM), and fertilization (IVF) of immature oocytes. Blastocysts produced in this fashion resulted in pregnancies and live calves after transfer to recipient animals. The results obtained were as follows:

| Step | Efficiency (%) | Number (per 100) |
| --- | --- | --- |
| IVM | 90 | 90 |
| IVF | 80 | 72 |
| IVC | 30 | 22 |
| Embryo transfer (% pregnant) | 50 | 11 |

Therefore, from an initial daily harvest of 500 oocytes, it is expected that approximately 55 pregnancies will result.

Preparation of oviduct tissue

Co-culture and conditioned medium

1. Obtain oviducts after slaughter or by salpingectomy.
2. Harvest lumenal tissue by scraping intact oviduct gently with a glass slide.
3. Wash tissue 5 times in 10 ml modified tyrodes-hepes solution (Parrish et al. (1988) *Biol. Reprod.* 38, 1171–1180).
4. Resuspend final tissue pellet in M199+10% fetal calf serum at a ratio of 1 volume tissue:50 volumes of media.
5. Tissue suspension can be used for embryo co-culture.
6. Alternatively, media may be conditioned for 48 hours; after centrifuging the suspension, the supernatant may be used as embryo culture medium. Conditioned medium may be stored at −70° C., if desired. Conditioned medium should be used at full strength for embryo culture (no dilution) (Eyestone (1989) ibid).

EXAMPLE 7

Microinjection of human β-casein transgene into bovine pronuclei

The DNA fragment containing the human β-casein expression system is excised from the vector by digestion with the appropriate restriction enzyme(s) and separated on agarose gels. The fragment is purified by electroelution, phenol and chloroform extraction and ethanol precipitation (Maniatis et al.). The DNA fragment is dissolved in and dialyzed in 10 mM tris, 0.1 mM EDTA pH 7.2 at a concentration of 1 to 2 µg/ml. Microinjection needles are filled with the dialyzed DNA solution.

Before in vitro fertilization, cumulus cells are removed from the egg by either vortexing at maximum speed for 2 minutes or pipetting the eggs up and down several times in a standard micropipette. Bovine pronuclei are injected in principle as murine pronuclei (Hogan, B. et al. (1986) in: Manipulating the mouse embryo, Cold Spring Harbor Laboratory) with an additional centrifugation step in order to visualize the pronuclei. The injection takes place 18–24 hours after fertilization. The time varies depending on the bull used as a source of semen. Different batches of semen cause the nuclei to become visible at different times.

Bovine oocytes, matured and fertilized in vitro, are spun in an eppendorf tube in 1 ml of tyrodes-hepes solution (Parrish (1987)) at 14500 g for eight minutes (Wall et al. (1985) *Biol. Reprod.* 32, 645–651). The embryos are transferred to a drop of tyrodes-hepes solution on a microscope slide covered with paraffin oil. Using a hydraulic system the oocytes are fixed to the egg holder in such a way that both the pronuclei are visible (using interference-contrast or phase contrast optics). If necessary, the oocytes are rolled to change their position on the egg holder to visualize the pronuclei. The injection needle is brought into the same sharp focus of one of the pronuclei. The needle is then advanced through the zona pellucida, cytoplasm into the pronucleus. A small volume of 13 pl is injected (containing 20–100 DNA copies) into the pronucleus either by using a constant flow or a pulse flow (using a switch) of DNA solution out of the needle. Alternatively, two cell stage embryos are spun as described and the nuclei of both blastomers are injected as described. The injected embryos are then transferred to a drop of co-culture medium as described in Example 6 in order to develop to the morula or blastocyst stage.

EXAMPLE 8

Early detection of transgenesis with human β-casein transgene

Upon the microinjection of a construct as described in Example 7, the oocyte is cultured. A proper site of each embryo is cleaved and subjected to lysis (King, D. et al. (1988) *Molecular Reproduction and Development* 1, 57–62), proteolysis (Higuchi, R. (1989) "Amplifications (A forum for PCR Users." 2, 1–3) and digestion. PCR is performed as described previously in Example 4 with sets of two primers, one in exon 3 (SYM 3120) (see Table 1) and the other in exon 4 (SYM 2887).

EXAMPLE 9

Production of human β-casein in milk of bovine species

Bovine morula developed from microinjected oocytes are split according to the method of Donahue (Donahue, S. (1986) *Genetic Engineering of Animals*, ed. J. Warren Evans et al., Plenum). One half of the morula is kept in culture to develop into blastocysts. The other half is subjected to the DNA analysis as described in Example 8. When the result of this analysis is known, the morula kept in culture are developed into a blastocyst or as a source for nuclear transfer into enucleated zygotes. Blastocyst transfer into synchronized cows is performed according to the method of Betteridge (Betteridge, K. J. (1977) in: Embryo transfer in farm animals: a review of techniques and applications).

Human β-casein is detected in the milk of lactating transgenic offspring using the methods described in Example 4.

DEPOSITION

Plasmid DNA, designated pS 21, pS 26, pS 28, pS 133 and pS 232, has been deposited in the collection of Deutsche Sammlung von Mikroorganismen und Zellkulturen GmbH, Mascheroder Weg 1b, D-3300 Braunschweig, Germany, on Aug. 19, 1991 in accordance with the provision of the Budapest Treaty and identified there by accession numbers DSM 6653, DSM 6654, DSM 6655, DSM 6656, and DSM 6657, respectively.

Plasmid DNA, designated pS316 and pS358, was deposited at DSM on 9 Jul., 1992 and received accession numbers DSM 7163 and DSM 7164, respectively.

We claim:

1. An expression system comprising a DNA sequence which encodes a polypeptide having at least 85% sequence identity with SEQ ID NO: 2 or which hybridizes under stringent conditions with SEQ ID NO: 1, the DNA sequence comprising at least one human beta casein intron sequence, and the system comprising a 5'-flanking sequence of a milk protein gene other than a casein gene, capable of mediating expression of said DNA sequence.

2. A method for producing a polypeptide having the amino acid sequence SEQ ID NO: 2 or an analogue or variant thereof which has the calcium binding activity of human beta casein, or opioid activity, or angiotensin converting enzyme (ACE) inhibitory activity, or a combination of any two or three of these activities, the method comprising introducing an expression system as claimed in claim 1 into the genome of a mouse in such a way that the DNA encoding the polypeptide is expressed in a mammary gland of the mouse, and collecting the polypeptide secreted from the mammary gland.

3. A method for producing a transgenic mouse capable of expressing a polypeptide having at least 85% sequence identity with SEQ ID NO: 2 or which hybridizes under stringent conditions with SEQ ID NO: 1, said method comprising chromosomally incorporating a DNA sequence comprising a polypeptide coding sequence encoding the polypeptide, at least one human beta casein intron sequence, and a promoter of a milk protein gene other than a casein gene, operatively associated with said coding sequence, into the genome of a mouse, whereby the polypeptide is expressed.

4. A transgenic mouse whose germ cells and somatic cells contain a DNA construct which comprises at least one human beta casein intron sequence and a promoter of a milk protein gene other than a casein gene, and a sequence which encodes a polypeptide having at least 85% sequence identity with SEQ ID NO: 2 or which hybridizes under stringent conditions with SEQ ID NO: 1, as a result of chromosomal incorporation of the construct into the mouse genome, or into the genome of an ancestor of said mouse, so that the DNA construct is expressed in a mammary gland of the transgenic mouse.

5. A transgenic mouse as claimed in claim 4 wherein the DNA construct is present within a mouse milk protein gene.

6. A method for supplementing a human infant formula comprising adding to said infant formula a polypeptide having the amino acid sequence of SEQ ID NO: 2 or an analogue or variant thereof which has the calcium binding activity of human beta casein, or opioid activity, or angiotensin converting enzyme (ACE) inhibitory activity, or a combination of any two or three of these activities, prepared by introducing an expression system according to claim 1 into the genome of a mouse in such a way that the DNA sequence which encodes a polypeptide having at least 85% sequence identity with SEQ ID NO: 2 or which hybridizes under stringent conditions with SEQ ID NO: 1, and comprises at least one human beta casein intron sequence, is capable of being expressed in a mammary gland of the mouse, obtaining expression of the polypeptide by said mouse, harvesting and optionally purifying the polypeptide expressed by said mouse.

7. An expression system according to claim 1 wherein the milk protein gene is a whey acidic protein gene.

* * * * *